United States Patent [19]

Shiokawa et al.

[11] Patent Number: 5,155,114
[45] Date of Patent: * Oct. 13, 1992

[54] METHOD OF TREATMENT USING PYRAZOLOPYRIDINE COMPOUND

[75] Inventors: Youichi Shiokawa, Ibaraki; Atsushi Akahane, Kawabe; Hirohito Katayama, Nishinomiya; Takafumi Mitsunaga, Ashiya, all of Japan

[73] Assignee: Fujisawa Pharmaceutical Company, Ltd., Osaka, Japan

[*] Notice: The portion of the term of this patent subsequent to Jan. 15, 2008 has been disclaimed.

[21] Appl. No.: 715,460

[22] Filed: Jun. 14, 1991

Related U.S. Application Data

[63] Continuation-in-part of Ser. No. 626,009, Jan. 18, 1990, abandoned, which is a continuation-in-part of Ser. No. 466,929, Dec. 12, 1990, Pat. No. 4,985,444.

[30] Foreign Application Priority Data

Jan. 23, 1989 [GB] United Kingdom ............. 8901423

[51] Int. Cl.$^5$ ............................................. A61K 31/435
[52] U.S. Cl. ................... 514/300; 514/254; 514/256
[58] Field of Search ........................................ 514/300

[56] References Cited

U.S. PATENT DOCUMENTS 4,985,444 1/1991 Shiokawa et al. ............. 546/121

Primary Examiner—Bernard Dentz
Attorney, Agent, or Firm—Oblon, Spivak, McClelland, Maier & Neustadt

[57] ABSTRACT

The invention relates to a method for the prevention and/or treatment of renal toxicity, nephrosis or nephritis, which comprises administering a pyrazolopyridine compound of the formula:

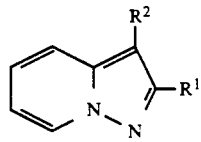

wherein
$R^1$ is aryl, and
$R^2$ is unsaturated heterocyclic group which contains at least one heteroatom selected from the group consisting of N, O and S, which may have one or more suitable substituent(s), or a pharmaceutically acceptable salt thereof to a human being or an animal.

1 Claim, No Drawings

METHOD OF TREATMENT USING PYRAZOLOPYRIDINE COMPOUND

This application is a continuation-in-part of parent application Ser. No. 626,009, filed Jan. 18, 1990, now abandoned, which in turn is a continuation of parent application Ser. No. 466,929, filed Dec. 12, 1990, now U.S. Pat. No. 4,985,444.

The present invention relates to novel pyrazolopyridine compound and a pharmaceutically acceptable salt thereof.

More particularly, it relates to novel pyrazolopyridine compound and a pharmaceutically acceptable salt thereof, which are adenosine antagonists and possess various pharmaceutical actions such as cognitive enhancing action, analgesic action, locomotor action, antidepressant action, cerebral vasodilating action, diuretic action, cardiotonic action, vasodilating action, the action of increasing the renal blood flow, renal prophylactic effect, improvemental effect of renal function, enhanced lipolysis action, inhibited anaphylactic bronchoconstrictive action, accelerating action of the release of insulin, antiulcerative action, protective effect against pancreatitis, or the like, and so are useful as psychostimulant, analgesic, antidepressant, ameliorants of cerebral circulation, drug for heart failure, cardiotonic agent, antihypertensive agent, drug for renal insufficiency (renal failure), drug for renal toxicity, renal prophylactic agent, improvemental agent of renal function, diuretic, drug for edema, antiobesity, antiasthmatic, bronchodilater, drug for apnea, drug for gout, drug for hyperuricemia, drug for sudden infant death syndrome (SIDS), ameliorants of immunosuppresion action of adenosine, antidiabetic agent, antiulcerative agent, drug for pancreatitis, or the like, and further which are inhibitors of platelet aggregation, so are useful as drug for thrombosis, drug for myocardiac infarction, drug for thrombophlebitis, drug for arteriosclerosis obliterans, drug for thrombophlebitis, drug for cerebral infarction, drug for transient ischemic attack, drug for angina pectoris, or the like; to a process for preparation thereof, to a pharmaceutical composition comprising the same, and to a method for using the same therapeutically in human being and animals for the prevention and/or treatment of melancholia, heart failure, hypertension (e.g. essential hypertension, nephrogenous hypertension, etc.), renal insufficiency (renal failure) (e.g. acute renal failure, etc.), renal toxicity [e.g. renal toxicity (damage of kidney) induced by a drug such as cisplatin, gentamicin, FR-900506 (disclosed in EP-0184162), cyclosporins (e.g. cyclosporin A) or the like; glycerol; etc.], nephrosis, nephritis, edema (e.g. cardiac edema, nephrotic edema, hepatic edema, idiopathic edema, drug edema, acute angioneurotic edema, hereditary angioneurotic edema, carcinomatous ascites, gestational edema, etc.), obesity, bronchial asthma, gout, hyperuricemia, sudden infant death syndrome, immunosuppresion, diabetes, ulcer such as peptic ulcer (e.g. gastic ulcer, duodenal ulcer, etc.), pancreatitis, myocardiac infarction, thrombosis (e.g. arterial thrombosis, cerebral thrombosis, etc.), obstruction, arteriosclerosis obliterans, thrombophlebitis, cerebral infarction, transient ischemic attack, angina pectoris or the like.

Accordingly, one object of the present invention is to provide the novel pyrazolopyridine compound and a pharmaceutically acceptable salt thereof, which are useful as stated above.

Another object of the present invention is to provide processes for the preparation of the novel pyrazolopyridine compound or a salt thereof.

A further object of the present invention is to provide a pharmaceutical composition comprising, as an active ingredient, said pyrazolopyridine compound or a pharmaceutically acceptable salt thereof.

Still further object of the present invention is to provide a method for using said pyrazolopyridine compound as aforesaid therapeutic use, which comprises administering said pyrazolopyridine compound to human being or animals.

The novel pyrazolopyridine compound of the present invention can be shown by the following formula (I).

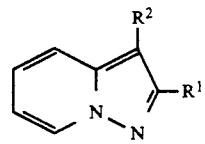

wherein
$R^1$ is aryl, and
$R^2$ is unsaturated heterocyclic group which may have one or more suitable substituent(s).

The object compound (I) or a salt thereof can be prepared, for example, according to the following reaction schemes.

Process 1

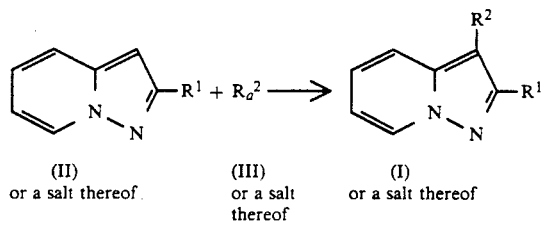

(II)
or a salt thereof (III)
or a salt thereof (I)
or a salt thereof

Process 2

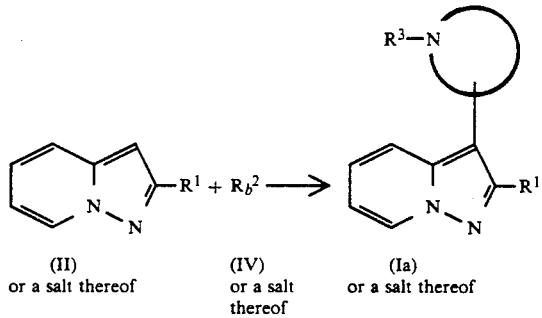

(II)
or a salt thereof (IV)
or a salt thereof (Ia)
or a salt thereof

Process 3

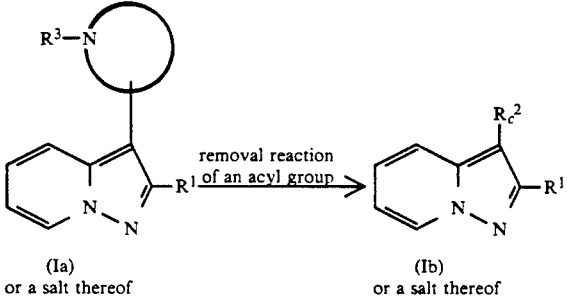

(Ia)
or a salt thereof (Ib)
or a salt thereof

3

-continued
Process 4

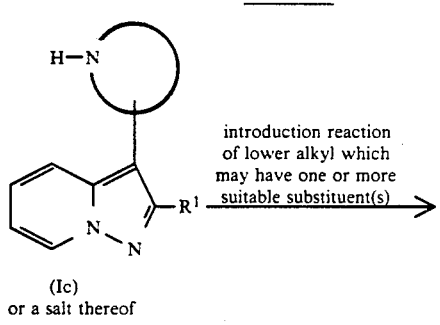
(Ic)
or a salt thereof introduction reaction of lower alkyl which may have one or more suitable substituent(s) →

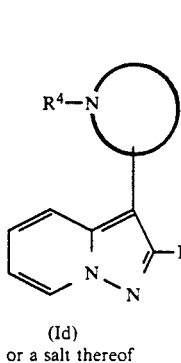
(Id)
or a salt thereof

Process 5

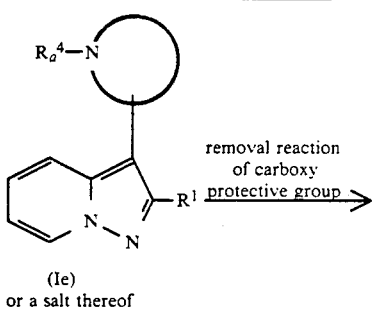
(Ie)
or a salt thereof removal reaction of carboxy protective group →

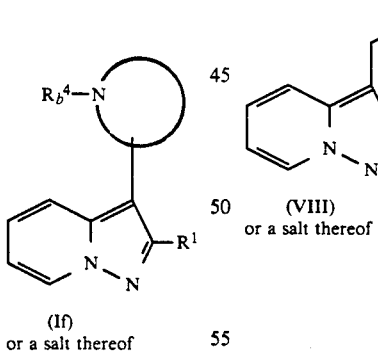
(If)
or a salt thereof

Process 6

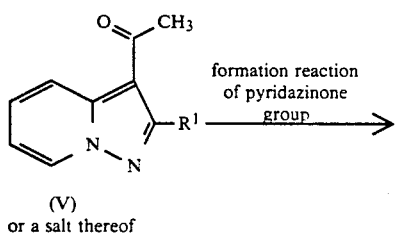
(V)
or a salt thereof formation reaction of pyridazinone group →

4

-continued

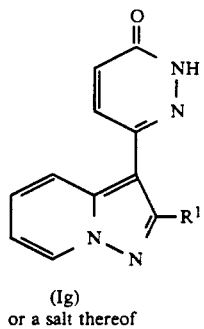
(Ig)
or a salt thereof

Process 7

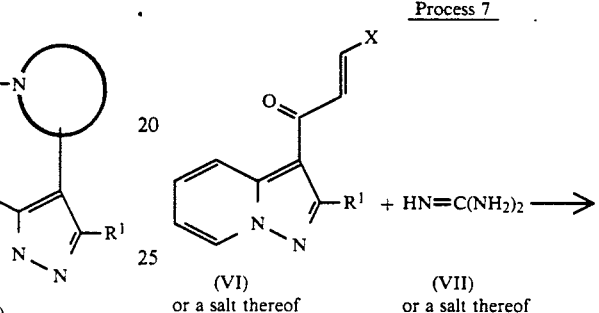
(VI)
or a salt thereof (VII)
or a salt thereof

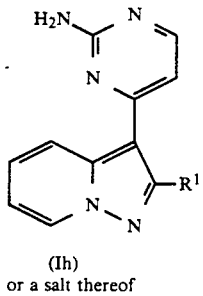
(Ih)
or a salt thereof

Process 8

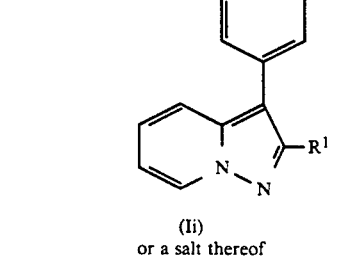
(VIII)
or a salt thereof

+ CH₃CONH₂ →

(IX)
or its reactive derivative at methyl group or a salt thereof

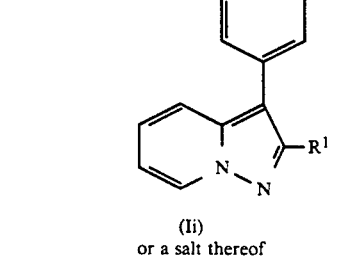
(Ii)
or a salt thereof

Process 9

-continued

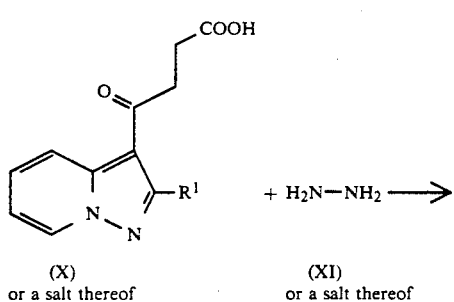

(X) or a salt thereof  +  H$_2$N—NH$_2$ → (XI) or a salt thereof

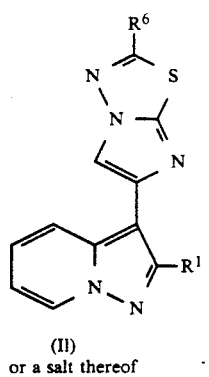

(II) or a salt thereof

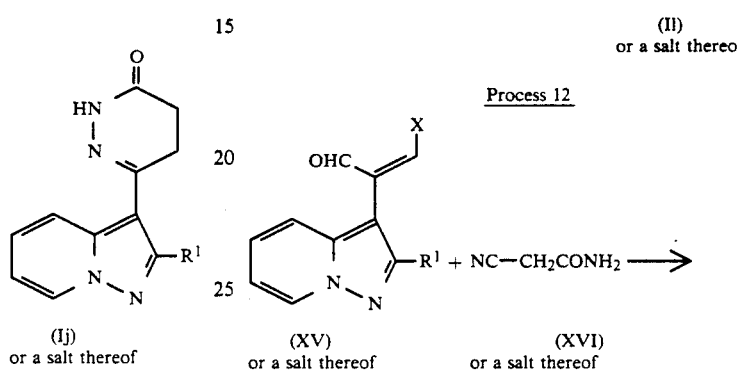

(Ij) or a salt thereof

Process 10

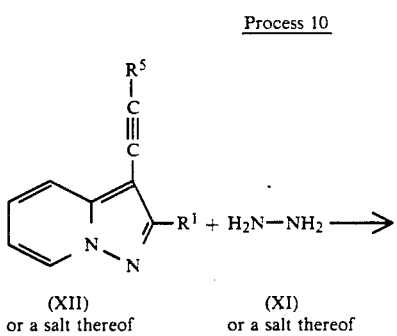

(XII) or a salt thereof  +  H$_2$N—NH$_2$ (XI) or a salt thereof →

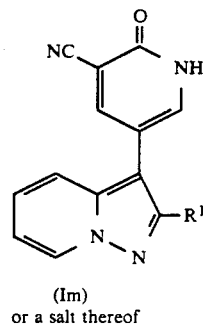

(Ik) or a salt thereof

Process 11

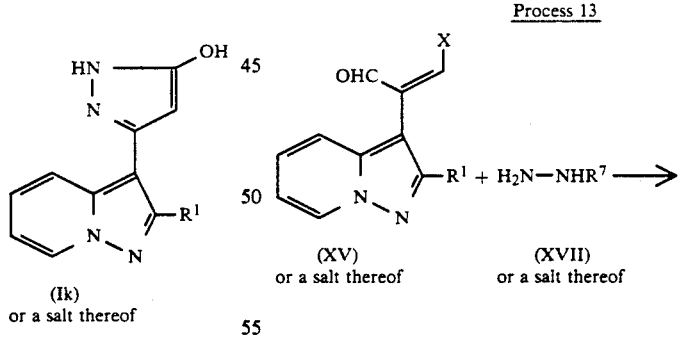

(XIII) or a salt thereof  +  (XIV) or a salt thereof →

Process 12

(XV) or a salt thereof  +  NC—CH$_2$CONH$_2$ (XVI) or a salt thereof →

(Im) or a salt thereof

Process 13

(XV) or a salt thereof  +  H$_2$N—NHR$^7$ (XVII) or a salt thereof →

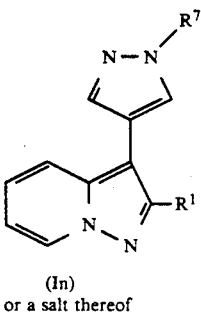

(In) or a salt thereof

Process 14

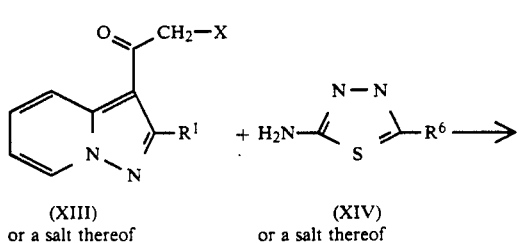

-continued

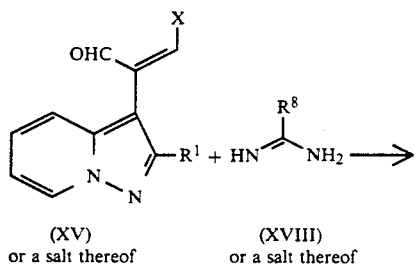

(XV)
or a salt thereof (XVIII)
or a salt thereof

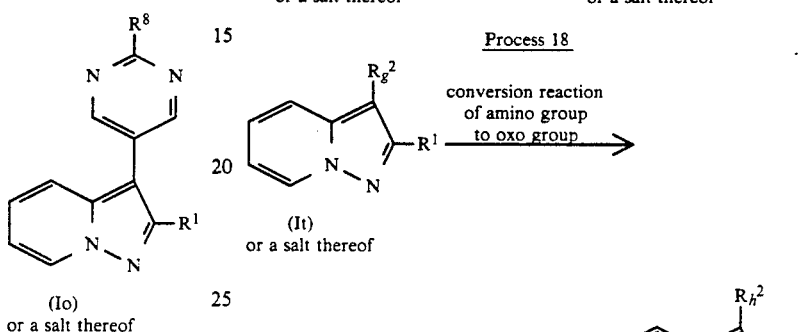

(Io)
or a salt thereof

Process 15

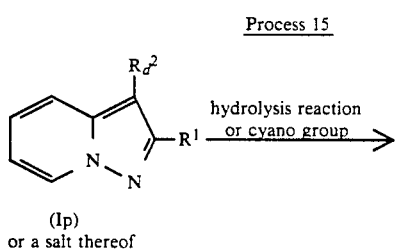

(Ip)
or a salt thereof hydrolysis reaction
or cyano group →

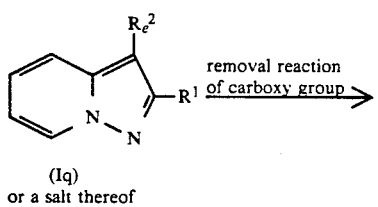

(Iq)
or a salt thereof

Process 16

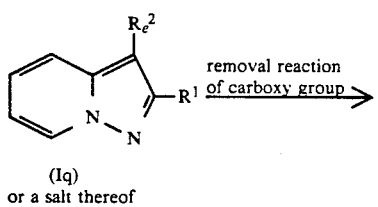

(Iq)
or a salt thereof removal reaction
of carboxy group →

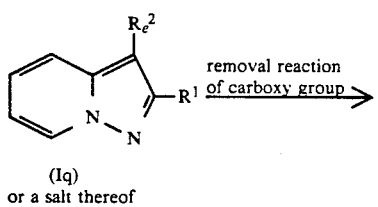

(Ir)
or a salt thereof

Process 17

-continued

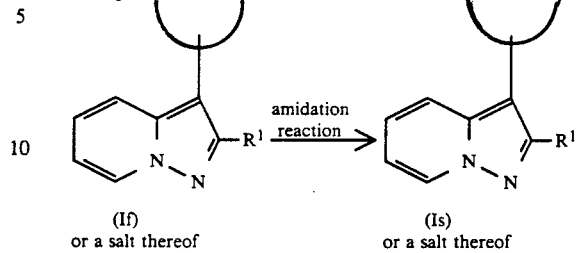

(If)
or a salt thereof amidation
reaction (Is)
or a salt thereof

Process 18

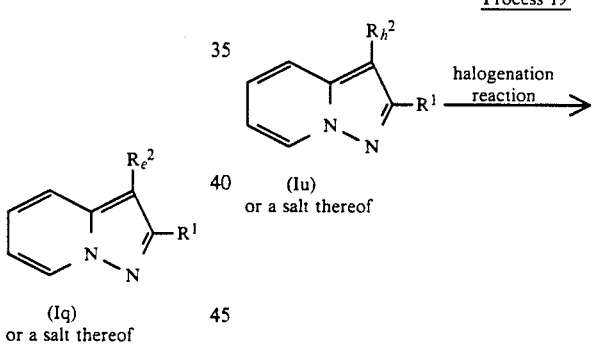

(It)
or a salt thereof conversion reaction
of amino group
to oxo group →

(Iu)
or a salt thereof

Process 19

(Iu)
or a salt thereof halogenation
reaction →

(Iv)
or a salt thereof

Process 20

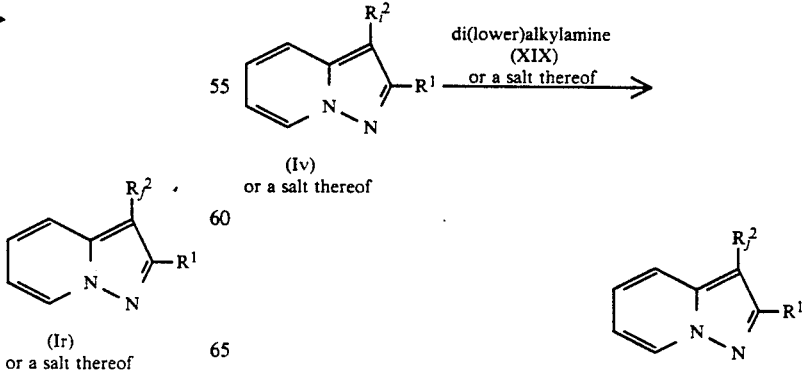

(Iv)
or a salt thereof di(lower)alkylamine
(XIX)
or a salt thereof →

(Iw)
or a salt thereof

Process 21

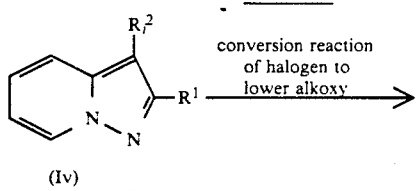
(Iv)
or a salt thereof conversion reaction
of halogen to
lower alkoxy
⟶

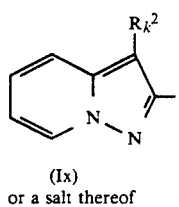
(Ix)
or a salt thereof

Process 22

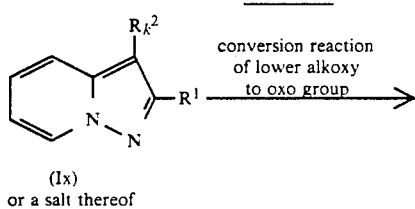
(Ix)
or a salt thereof conversion reaction
of lower alkoxy
to oxo group
⟶

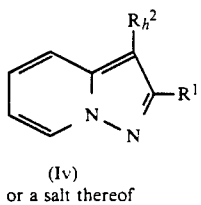
(Iv)
or a salt thereof

Process 23

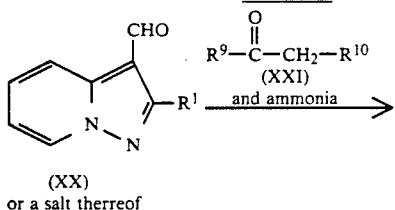
(XX)
or a salt therreof $R^9-\overset{O}{\underset{\|}{C}}-CH_2-R^{10}$
(XXI)
and ammonia
⟶

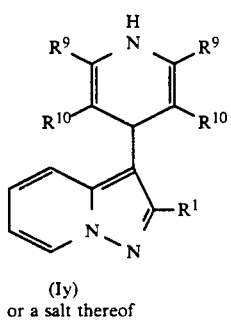
(Iy)
or a salt thereof wherein
R$^1$ and R$^2$ are each as defined above,
R$_a{}^2$ is heterocyclic compound having

moiety in its ring, which may have one or more suitable substituent(s),

R$_b{}^2$ is N-containing unsaturated heterocyclic compound having =N— moiety in its ring, which may have one or more suitable substituent(s), R$_c{}^2$ is N-containing unsaturated heterocyclic group, which may have one or more suitable substituent(s), R$_d{}^2$ is unsaturated heterocyclic group having cyano, which may have one or more suitable substituent(s), R$_e{}^2$ is unsaturated heterocyclic group having carboxy, which may have one or more suitable substituent(s), R$_f{}^2$ is unsaturated heterocyclic group which may have one or more suitable substituent(s) except carboxy, R$_g{}^2$ is unsaturated heterocyclic group having amino, which may have one or more suitable substituent(s), R$_h{}^2$ is unsaturated heterocyclic group having oxo, which may have one or more suitable substituent(s), R$_i{}^2$ is unsaturated heterocyclic group having halogen, which may have one or more suitable substituent(s), R$_j{}^2$ is unsaturated heterocyclic group having di(-lower)alkylamino, which may have one or more suitable substituent(s), R$_k{}^2$ is unsaturated heterocyclic group having lower alkoxy, which may have one or more suitable substituent(s), a group of the formula:

is unsaturated cyclic amino group, which may have one or more suitable substituent(s), R$^3$ is an acyl group, R$^4$ is lower alkyl which may have one or more suitable substituent(s), R$_a{}^4$ is protected carboxy(lower)alkyl, R$_b{}^4$ is carboxy(lower)alkyl, R$_c{}^4$ is amidated carboxy(lower)alkyl, R$^5$ is protected carboxy, R$^6$ is lower alkyl, R$^7$ is hydrogen or lower alkyl, R$^8$ is hydrogen, lower alkyl or amino, R$^9$ is lower alkyl, R$^{10}$ is protected carboxy, X is a leaving group.

Among the starting compounds, the compounds (VI), (X), (XII) and (XV) are novel, and they can be prepared according to the methods described in Preparations disclosed later in the present specifications or similar manners thereto.

Suitable pharmaceutically acceptable salts of the object compound (I) are conventional ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumalate, methanesulfonate, benzenesulfonate, formate, toluenesulfonate, etc.), an inorganic acid salt (e.g. hydrochloride, hydrobromide, hydroiodide, sulfate, phosphate, etc.), a salt with an amino acid (e.g. arginine, aspartic acid, glutamic acid, etc.), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

Suitable "aryl" may include phenyl, tolyl, xylyl, naphthyl and the like, in which the preferred one may be phenyl.

Suitable "unsaturated heterocyclic group" may include unsaturated, monocyclic or polycyclic heterocyclic group containing at least one hetero atom such as nitrogen, oxygen, sulfur or the like.

Suitable examples of said "unsaturated heterocyclic group" may include:

unsaturated 3 to 8-membered (more preferably 5 to 7-membered) heteromonocyclic group containing 1 to 4 nitrogen atom(s), for example, azepinyl (e.g. 1H-azepinyl, etc.) pyrrolyl, pyrrolinyl, imidazolyl, pyrazolyl, pyridyl, dihydropyridyl (e.g. 1,2-dihydropyridyl, 1,4-dihydropyridyl, etc.), tetrahydropyridyl (e.g. 1,2,3,6-tetrahydropyridyl, etc.) pyrimidinyl, dihydropyrimidinyl (e.g. 1,2-dihydropyrimidinyl, etc.), pyrazinyl, pyridazinyl, dihydropyridazinyl (e.g. 2,3-dihydropyridazinyl, 1,4-dihydropyridazinyl, etc.), tetrahydropyridazinyl (e.g. 2,3,4,5-tetrahydropyridazinyl, etc.) triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

unsaturated condensed heterocyclic group containing 1 to 4 nitrogen atom(s), for example, indolyl, isoindolyl, indolizinyl, benzimidazolyl, quinolyl, dihydroquinolyl (e.g. 2,3-dihydroquinolyl, etc.) isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, dihydroisoxazolyl (e.g. 2,5-dihydroisoxazolyl, etc.) oxadiazolyl (e.g. 1,2,4-oxadiazolyl, 1,3,4-oxadiazolyl, 1,2,5-oxadiazolyl, etc.), etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, dihydrothiazolyl (e.g. 2,3-dihydrothiazolyl, etc.) isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

unsaturated condensed heterocyclic group containing 1 to 2 sulfur atom(s) and 1 to 3 nitrogen atom(s), for example, benzothiazolyl, benzothiadiazolyl, (e.g. benzo[d][1,2,3]thiadiazolyl, etc.), imidazothiadiazolyl (e.g. 5H-imidazo[2,1-b][1,3,4]thiadiazolyl, etc.), etc.;

unsaturated 3 to 8-membered (more preferably 5 or 6-membered) heteromonocyclic group containing 1 to 2 sulfur atom(s), for example, thienyl, dihydrodithiinyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s) for example, benzoxathiinyl, etc. and the like, in which the preferred one may be unsaturated heterocyclic group containing at least one nitrogen atom as hetero atom, the more preferred one may be unsaturated 3 to 8-membered heteromonocyclic group containing 1 to 4 nitrogen atom(s) and unsaturated condensed heterocyclic group containing 1 to 2 sulfur atom(s) and 1 to 3 nitrogen atom(s), the much more preferred one may be pyridazinyl, dihydropyridazinyl, tetrahydropyridazinyl, pyrimidinyl, dihydropyrimidinyl, pyridyl, dihydropyridyl, tetrahydropyridyl, pyrazolyl and imidazothiadiazolyl, and the most preferred one may be pyridazinyl, 2,3-dihydropyridazinyl, 1,4-dihydropyridazinyl, 2,3,4,5-tetrahydropyridazinyl, pyrimidinyl, 1,2-dihydropyrimidinyl, pyridyl, 1,2-dihydropyridyl, 1,4-dihydropyridyl, 1,2,3,6-tetrahydropyridyl, pyrazolyl, and imidazo[2,1-b][1,3,4]thiadiazolyl.

Aforesaid "unsaturated heterocyclic group" may have one or more (preferably 1 to 4) suitable substituent(s) such as lower alkyl (e.g. methyl, ethyl, propyl, isopropyl, butyl, t-butyl, pentyl, hexyl, etc.) which may have one or more (preferably 1 to 4) suitable substituent(s) as explained below; carboxy(lower)alkenyl (e.g. 1-carboxyvinyl, 2-carboxyvinyl, 1-carboxy-2-propenyl, 3-carboxy-2-propenyl, 3-carboxy-2-butenyl, 4-carboxy-2-methyl-2-butenyl, 3-carboxy-1-hexenyl, etc.); amino; di(lower)alkylamino (e.g. dimethylamino, N-methylethylamino, dipropylamino, N-butyl-(2-methylbutyl)amino, N-pentylhexylamino, etc.); halogen (e.g. fluoro, chloro, bromo, iodo, etc.); lower alkoxy (e.g. methoxy, ethoxy, propoxy, isopropoxy, butoxy, t-butoxy, pentyloxy, hexyloxy, etc.); oxo; hydroxy; cyano; an acyl group as explained below; or the like.

Suitable "an acyl group" may include lower alkanoyl (e.g. formyl, acetyl, propionyl, butyryl, isobutyryl, pivaloyl, hexanoyl, etc.), carboxy, protected carboxy, and the like.

Suitable examples of aforesaid "protected carboxy" may be esterified carboxy, in which suitable esterified carboxy may include lower alkoxycarbonyl (e.g. methoxycarbonyl, ethoxycarbonyl, propoxycarbonyl, t-butoxycarbonyl, pentyloxycarbonyl, hexyloxycarbonyl, etc.) and the like;

amidated carboxy, in which suitable amidated carboxy may include carbamoyl, N,N-di(lower)alkylcarbamoyl wherein two lower alkyl groups may bond to each other to form 3 to 6-membered ring (e.g. N,N-dimethylcarbamoyl, N-methyl-N-ethylcarbamoyl, N,N-diethylcarbamoyl, N,N-dipropylcarbamoyl, N-butyl-N-t-butylcarbamoyl, N,N-dipentylcarbamoyl, N-pentyl-N-hexylcarbamoyl, 1-aziridinylcarbonyl, 1-azetidinylcarbonyl, 1-pyrrolidinylcarbonyl, piperidinocarbonyl, etc.) and the like; or the like.

Suitable examples of "suitable substituent(s)" of aforesaid "lower alkyl which may have one or more suitable substituent(s)" may include hydroxy, aforesaid halogen, aforesaid lower alkoxy, aforesaid an acyl group, and the like.

Suitable examples of said "lower alkyl having one or more suitable substituent(s)" may include lower alkyl having hydroxy and halogen (e.g. 1-hydroxy-1-chloromethyl, 1-hydroxy-2-chloroethyl, 2-hydroxy-3-fluoropropyl, 2-hydroxy-3,3,3-trichloropropyl, 3- bromo-4-hydroxy-4-iodobutyl, 1-chloro-2-hydroxy-4-fluoropentyl, 3,4-dihydroxy-6-chlorohexyl, etc.);

hydroxy(lower)alkyl (e.g. hydroxymethyl, 2-hydroxyethyl, 2-hydroxypropyl, 3-hydroxypropyl, 1-hydroxy-1-methylethyl, 1-hydroxybutyl, 1-hydroxymethyl-1-methylethyl, 3-hydroxypentyl, 2-hydroxyhexyl, etc.);

lower alkoxy(lower)alkyl (e.g. methoxymethyl, ethoxymethyl, 2-ethoxyethyl, 1-propoxyethyl, 3-isopropoxypropyl, 2-butoxybutyl, 1-t-butoxymethyl-1-methylethyl, 5-pentyloxypentyl, hexyloxymethyl, 3-hexyloxyhexyl, etc.);

acyl(lower)alkyl, in which the preferred one may be carboxy(lower)alkyl (e.g. carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl, 2-carboxyhexyl, etc.), and protected carboxy(lower)alkyl, in which the preferred one may be esterified carboxy(lower)alkyl and amidated carboxy(lower)alkyl, the more preferred one may be lower alkoxycarbonyl(lower)alkyl (e.g. methoxycarbonylmethyl, ethoxycarbonylmethyl, 2-methoxycarbonylethyl, 2-ethoxycarbonylethyl, 1-propoxycarbonylethyl, 3-ethoxycarbonylpropyl, 2-butoxycarbonylbutyl, 4-ethoxycarbonylbutyl, 1-t-butoxycarbonylmethyl-1-methylethyl, 5-pentyloxycarbonylpentyl, hexyloxycarbonylmethyl, 3-hexyloxycarbonylhexyl, etc.), carbamoyl(lower)alkyl (e.g. carbamoylmethyl, 2-carbamoylethyl, 3-carbamoylpropyl, 2-carbamoyl-1-methylethyl, 4-carbamoylbutyl, 1-carbamoylmethyl-1-methylethyl, 5-carbamoylpentyl, 3-carbamoylhexyl, etc.), N,N-di(lower)alkylcarbamoyl(lower)alkyl in which two lower alkyl groups on nitrogen atom may bond to each other to from 3 to 6-membered ring [e.g. N,N-dimethylcarbamoylmethyl, 2-(N,N-dimethylcarbamoyl)ethyl, 2-(N-methyl-N-ethylcarbamoyl)ethyl, 3-(N-methyl-N-ethylcarbamoyl)propyl, 2-(N,N-dipropylcarbamoyl)-1-methylethyl, 4-(N,N-dipropylcarbamoyl)butyl, 1-(N,N-dimethylcarbamoyl)-methyl-1-methylethyl, 5-(N-pentyl-N-hexylcarbamoyl)pentyl, 3-(N-pentyl-N-hexyl)hexyl, (1-aziridinylcarbonyl)methyl, 2-(1-azetidinylcarbonyl)ethyl, 2-(piperidinocarbonyl)ethyl, 3-(1-pyrrolidinylcarbonyl)propyl, 2-(1-piperidinocarbonyl)-1-methylethyl, 4-(1-azetidinylcarbonyl)butyl, 1-(1-aziridinylcarbonyl)methyl-1-methylethyl, 3-(1-pyrrolidinylcarbonyl)pentyl, 6-(piperidinocarbonyl)hexyl, etc.]; and the like.

The preferred substituent of "unsaturated heterocyclic group" may be lower alkyl, lower alkyl having hydroxy and halogen, hydroxy(lower)alkyl, lower alkoxy(lower)alkyl, carboxy(lower)alkyl, lower alkoxycarbonyl(lower)alkyl, carbamoyl(lower)alkyl, N,N-di(lower)alkylcarbamoyl(lower)alkyl wherein two lower alkyl groups on nitrogen atom may bond to each other to form 3 to 6-membered ring, carboxy(lower)alkenyl, di(lower)alkylamino, halogen, lower alkoxy, oxo, carboxy, lower alkoxycarbonyl, lower alkanoyl, amino, cyano and hydroxy, in which the more preferred one may be (C$_1$-C$_4$)alkyl, (C$_1$-C$_4$)alkyl having hydroxy and halogen, hydroxy(C$_1$-C$_4$)alkyl, (C$_1$-C$_4$)alkoxy(C$_1$-C$_4$)alkyl, carboxy(C$_1$-C$_4$)alkyl, (C$_1$-C$_4$)alkoxycarbonyl(C$_1$-C$_4$)alkyl, carbamoyl(C$_1$-C$_4$)alkyl, N,N-di(C$_1$-C$_4$)alkylcarbamoyl(C$_1$-C$_4$)alkyl, piperidinocarbonyl(C$_1$-C$_4$)alkyl, carboxy(C$_2$-C$_4$)alkenyl, di(C$_1$-C$_4$)alkylamino, halogen, (C$_1$-C$_4$)alkoxy, oxo, carboxy, (C$_1$-C$_4$)alkoxycarbonyl, (C$_1$-C$_4$)alkanoyl, amino, cyano and hydroxy, and the most preferred one may be methyl, propyl, 2-hydroxy-3,3,3-trichloropropyl, 2-hydroxyethyl, 3-hydroxypropyl, 2-ethoxyethyl, 2-carboxyethyl, 3-carboxypropyl, 4-carboxybutyl, methoxycarbonylmethyl, 2-methoxycarbonylethyl, 3-ethoxycarbonylpropyl, 4-ethoxycarbonylbutyl, 2-carbamoylethyl, 2-(N,N-dimethylcarbamoyl)ethyl, 2-(piperidinocarbonyl)ethyl, 2-carboxyvinyl, dimethylamino, chloro, methoxy, oxo, carboxy, ethoxycarbonyl, methoxycarbonyl, acetyl, amino, cyano and hydroxy.

Suitable "heterocyclic compound having

moiety in its ring" may include saturated or unsaturated, monocyclic or polycyclic heterocyclic compound containing at least one hetero atom such as nitrogen, oxygen, sulfur or the like, which has

moiety in its ring, and suitable examples thereof may include:

saturated or unsaturated 3 to 8-membered (more preferably 5 to 7-membered) heteromonocyclic compound containing 1 to 4 nitrogen atom(s) which has

moiety in its ring, for example, azepine having oxo (e.g. 2-oxo-2H-azepine, etc.), pyrrole having oxo (e.g. 5-oxopyrroline, etc.), pyrroline having oxo (e.g. 2-oxopyrrolidine, etc.), imidazole having oxo (e.g. 4-oxoimidazoline, etc.), pyrazole having oxo (e.g. 5-oxopyrazoline, etc.), pyridine having oxo (e.g. 4-oxo-1,4-dihydropyridine, etc.), dihydropyridine having oxo (e.g. 2-oxo-1,2,3,4-tetrahydropyridine, 4-oxo-1,2,3,4-tetrahydropyridine, etc.), tetrahydropyridine having oxo (e.g. 2-oxopiperidine, 4-oxopiperidine, etc.), pyrimidine having oxo (e.g. 2-oxo-1,2-dihydropyrimidine, etc.), dihydropyrimidine having oxo (e.g. 4-oxo-1,2,3,4-tetrahydropyrimidine, etc.), pyrazine having oxo (e.g. 2-oxo-1,2-dihydropyrazine, etc.), pyridazone having oxo (e.g. 3-oxo-3,4-dihydropyridazine, etc.), dihydropyridazine having oxo (e.g. 4-oxo-2,3,4,5-tetrahydropyridazine, 3-oxo-2,3,4,5-tetrahydropyridazine, etc.), dihydropyridazine having oxo (e.g. 3-oxo-perhydropyridazine, etc.), triazole having oxo (e.g. 3-oxo-2,3-dihydro-4H-1,2,4-triazole, 4-oxo-4,5-dihydro-1H-1,2,3-triazole, 5-oxo-1,5-dihydro-2H-1,2,3-triazole, etc.), tetrazole having oxo (e.g. 5-oxo-4,5-dihydro-1H-tetrazole, 5-oxo-1,5-dihydro-2H-tetrazole, etc.), etc.;

saturated or unsaturated condensed heterocyclic compound containing 1 to 4 nitrogen atom(s) which has

moiety in its ring, for example, indole having oxo (e.g. 2-oxo-2,3-dihydroindole, etc.), isoindole having oxo (e.g. 7-oxo-6,7-dihydroisoindole, etc.), indolizine having oxo (e.g. 3-oxo-2,3-dihydroindolizine, etc.), benzimidazole having oxo (e.g. 2-oxo-2,3-dihydro-1H-benzimidazole, etc.), quinoline having oxo (e.g. 4-oxo-3,4-dihydroquinoline, etc.), dihydroquinoline having oxo (e.g. 5-oxo-1,4,5,6-tetrahydroquinoline, etc.), isoquinoline having oxo (e.g. 4-oxo-3,4-dihydroisoquinoline, etc.), indazole having oxo (e.g. 3-oxo-2,3-dihydro-1H-indazole, etc.), benzotriazole having oxo (e.g. 4-oxo-4,5-dihydro-1H-benzotriazole, etc.), etc.;

saturated or unsaturated 3 to 8-membered (more preferably 5 to 6-membered) heteromonocyclic compound containing 1 to 2 oxygen atom(s) and 1 to 3 nitrogen atom(s) which has

moiety in its ring, for example, oxazole having oxo (e.g. 4-oxo-4,5-dihydroxazole, etc.), isoxazole having oxo (e.g. 3-oxo-2,3-dihydroisoxazole, etc.), dihydroisoxazole having oxo (e.g. 4-oxo-isoxazolidine, etc.), oxadiazole having oxo (e.g. 3-oxo-2,3-dihydro-1,2,4-oxadiazole, 3-oxo-2,3-dihydro-1,2,5-oxadiazole, etc.), etc.;

saturated or unsaturated condensed heterocyclic compound containing 1 to 2 oxygen atom(s) and 1 to 3 nitrogen atom(s) which has

moiety in its ring, for example, benzoxazole having oxo (e.g. 2-oxo-2,3-dihydrobenzoxazole, etc.), benzoxadiazole having oxo (e.g. 5-oxo-4,5-dihydrobenzoxadiazole, etc.), etc.;

saturated or unsaturated 3 to 8-membered (more preferably 5 or 6-membered) heteromonocyclic compound containing 1 to 2 sulfur atom(s) and 1 to 3 nitrogen atom(s) which has

moiety in its ring, for example, thiazole having oxo (e.g. 4-oxo-4,5-dihydrothiazole, etc.), dihydrothiazole having oxo (e.g. 4-oxo-thiazolidine, etc.), isothiazole having oxo (e.g. 3-oxo-2,3-dihydroisothiazole, etc.), thiadiazole having oxo (e.g. 4-oxo-4,5-dihydro-1,2,3-thiadiazole, 3-oxo-2,3-dihydro-1,2,4-thiadiazole, 2-oxo-2,3-dihydro-1,3,4-thiadiazole, 3-oxo-2,3-dihydro-1,2,5-thiadiazole, etc.), dihydrothiazine having oxo (e.g. 4-oxo-perhydro-1,3-thiazine, etc.), etc.;

saturated or unsaturated condensed heterocyclic compound containing 1 to 2 sulfur atom(s) and 1 to 3 nitrogen atom(s) which has

moiety in its ring, for example, benzothiazole having oxo (e.g. 2-oxo-2,3-dihydrobenzothiazole, etc.), benzothiadiazole having oxo (e.g. 6-oxo-6,7-dihydrobenzothiadiazole, etc.), imidazothiadiazole having oxo (e.g. 5-oxo-5H-imidazo[2,1-b][1,3,4]thiadiazole, etc.), etc.;

saturated or unsaturated 3 to 8-membered (more preferably 5 or 6-membered) heteromonocyclic compound containing 1 to 2 sulfur atom(s) which has

moiety in its ring, for example, thiophene having oxo (e.g. 3-oxo-2,3-dihydrothiophene, etc.), dihydrothiin having oxo (e.g. 5-oxo-thiane, etc.), etc.;

saturated or unsaturated 3 to 8-membered (more preferably 5 to 6-membered) heteromonocyclic compound containing an oxygen atom which has

moiety in its ring, for example, furan having oxo (e.g. 3-oxo-2,3-dihydrofuran, etc.), dihydrofuran having oxo (e.g. 3-oxo-furrolane, etc.), etc.;

saturated or unsaturated 3 to 8-membered (more preferably 5 to 6-membered) heteromonocyclic compound containing an oxygen atom and 1 to 2 sulfur atom(s) which has

moiety in its ring, for example, dihydroxathiin having oxo (e.g. 3-oxo-1,4-oxathiane, etc.), oxathiin having oxo (e.g. 3-oxo-2,3-dihydroxathiin, etc.), etc.;

saturated or unsaturated condensed heterocyclic compound containing 1 to 2 sulfur atom(s) which has

moiety in its ring, for example, benzothiophene having oxo (e.g. 3-oxo-2,3-dihydrobenzo[b]thiophene, etc.), benzodithiin having oxo (e.g. 2-oxo-2,3-dihydrobenzo[b][1,4]dithiin, etc.), etc.;

saturated or unsaturated condensed heterocyclic compound containing an oxygen atom and 1 to 2 sulfur atom(s) which has

moiety in its ring, for example, benzoxathiin having oxo (e.g. 6-oxo-5,6-dihydrobenz[b][1,4]oxathiin, etc.), etc.; and the like.

Aforesaid "heterocyclic compound having

moiety in its ring" may have one or more (preferably 1 to 4) suitable substituent(s) as exemplified above for "suitable substituent(s)" of "unsaturated heterocyclic group".

Suitable "N-containing unsaturated heterocyclic compound having =N— moiety in its ring" may be heterocyclic compound containing at least one nitrogen atom and also containing at least one =N— moiety in its ring.

Suitable example of said "N-containing unsaturated heterocyclic compound having =N— moiety in its ring" may include:

unsaturated 3 to 8-membered (more preferably 5 to 7-membered) heteromonocyclic compound containing 1 to 4 nitrogen atom(s) having =N— moiety in its ring, for example, azepine (e.g. 1H-azepine, etc.) imidazole, pyrazole, pyridine, dihydropyridine (e.g. 3,4-dihydropyridine, 5,6-dihydropyridine, etc.), tetrahydropyridine (e.g. 3,4,5,6-tetrahydropyridine, etc.) pyrimidine, dihydropyrimidine (e.g. 1,2-dihydropyrimidine, etc.), pyrazine, pyridazine, dihydropyridazine (e.g. 2,3-dihydropyridazine, 1,4-dihydropyridazine, etc.), tetrahydropyridazine (e.g. 2,3,4,5-tetrahydropyridazine, etc.), triazole (e.g. 4H-1,2,4-triazole, 1H-1,2,3-triazole, 2H-1,2,3-triazole, etc.), tetrazole (e.g. 1H-tetrazole, 2H-tetrazole, etc.), etc.;

unsaturated condensed heterocyclic compound containing 1 to 4 nitrogen atom(s) having =N— moiety in its ring, for example, indole, benzimidazole, quinoline dihydroquinoline (e.g. 3,4-dihydroquinoline, etc.) isoquinoline, indazole, benzotriazole, etc.;

unsaturated 3 to 8-membered (more preferably 5 or 6-membered) heteromonocyclic compound containing 1 to 2 oxygen atom(s) and 1 to 3 nitrogen atom(s) having =N— moiety in its ring, for example, oxazole, isoxazole, dihydroisoxazole (e.g. 4,5-dihydroisoxazole, etc.) oxadiazole (e.g. 1,2,4-oxadiazole, 1,3,4-oxadiazole, 1,2,5-oxadiazole, etc.), etc.;

unsaturated condensed heterocyclic compound containing 1 to 2 oxygen atom(s) and 1 to 3 nitrogen atom(s), having =N— moiety in its ring, for example, benzoxazole, benzoxadiazole, etc.;

unsaturated 3 to 8-membered (more preferably 5 or 6-membered) heteromonocyclic compound containing 1 to 2 sulfur atom(s) and 1 to 3 nitrogen atom(s) having =N— moiety in its ring, for example, thiazole, dihydrothiazole (e.g. 4,5-dihydrothiazole, etc.) isothiazole, thiadiazole (e.g. 1,2,3-thiadiazole, 1,2,4-thiadiazole, 1,3,4-thiadiazole, 1,2,5-thiadiazole, etc.), dihydrothiazine, etc.;

unsaturated condensed heterocyclic compound containing 1 to 2 sulfur atom(s) and 1 to 3 nitrogen atom(s) having =N— moiety in its ring, for example, benzothiazole, benzothiadiazole, imidazothiadiazole, etc.

Aforesaid "N-containing unsaturated heterocyclic compound having =N— moiety in its ring" may have one or more (preferably 1 to 4) suitable substituent(s) as exemplified above for "suitable substituent(s)" of "unsaturated heterocyclic group".

Suitable "N-containing unsaturated heterocyclic group" may be unsaturated heterocyclic group containing at least one nitrogen atom as hetero atom and suitable examples thereof can be referred to unsaturated heterocyclic group containing at least one nitrogen atom as exemplified for "unsaturated heterocyclic group" before.

Aforesaid "N-containing unsaturated heterocyclic group" may have one or more (preferably 1 to 4) suitable substituent(s) as exemplified above for "suitable substituent(s)" of "unsaturated heterocyclic group".

Suitable "unsaturated heterocyclic group having cyano" may be "unsaturated heterocyclic group" as explained above which has cyano as its substituent, and said "unsaturated heterocyclic group having cyano" may have additionally one or more (preferably 1 to 4) suitable substituent(s) as exemplified above for "suitable substituent(s)" of "unsaturated heterocyclic group".

Suitable "unsaturated heterocyclic group having carboxy" may be "unsaturated heterocyclic group" as explained above which has carboxy as its substituent, and said "unsaturated heterocyclic group having carboxy" may have additionally one or more (preferably 1 to 4) suitable substituent(s) as exemplified above for "suitable substituent(s)" of "unsaturated heterocyclic group".

Suitable "unsaturated heterocyclic group having amino" may be "unsaturated heterocyclic group" as explained above which has amino as its substituent, and said "unsaturated heterocyclic group having amino" may have additionally one or more (preferably 1 to 4) suitable substituent(s) as exemplified above for "suitable substituent(s)" of "unsaturated heterocyclic group".

Suitable "unsaturated heterocyclic group having oxo" may be "unsaturated heterocyclic group" as explained above which has oxo as its substituent, and said "unsaturated heterocyclic group having oxo" may have additionally one or more (preferably 1 to 4) suitable substituent(s) as exemplified above for "suitable substituent(s)" of "unsaturated heterocyclic group".

Suitable "unsaturated heterocyclic group having halogen" may be "unsaturated heterocyclic group" as explained above which has carboxy as its substituent, and said "unsaturated heterocyclic group having halogen" may have additionally one or more (preferably 1 to 4) suitable substituent(s) as exemplified above for "suitable substituent(s)" of "unsaturated heterocyclic group".

Suitable "unsaturated heterocyclic group having di(lower)alkylamino" may be "unsaturated heterocyclic group" as explained above which has di(lower)alkylamino as its substituent, and said "unsaturated heterocyclic group having di(lower)alkylamino" may have additionally one or more (preferably 1 to 4) suitable substituent(s) as exemplified above for "suitable substituent(s)" of "unsaturated heterocyclic group".

Suitable "unsaturated heterocyclic group having lower alkoxy" may be "unsaturated heterocyclic group" as explained above which has carboxy as its substituent, and said "unsaturated heterocyclic group having lower alkoxy" may have additionally one or more (preferably 1 to 4) suitable substituent(s) as exemplified above for "suitable substituent(s)" of "unsaturated heterocyclic group".

Suitable "unsaturated heterocyclic group which may have one or more suitable substituent(s) except carboxy" may be "unsaturated heterocyclic group" as explained above which may have one or more (preferably 1 to 4) suitable substituent(s), as exemplified for "suitable substituent(s)" of "unsaturated heterocyclic group", except carboxy.

Suitable "unsaturated cyclic amino group" may include unsaturated, monocyclic or polycyclic amino group which may contain additional hetero atom such as nitrogen, oxygen, sulfur or the like.

Suitable examples of said "unsaturated cyclic amino group" may include:

unsaturated 3 to 8-membered (more preferably 5 to 7-membered) heteromonocyclic amino group containing 1 to 4 nitrogen atom(s), for example, azepin-1-yl (e.g. 1H-azepin-1-yl, etc.) 1-pyrrolyl, 1-pyrrolinyl, 1-imidazolyl, 1-pyrazolyl, dihydropyridin-1-yl (e.g. 1,2-dihydropyridin-1-yl, 1,4-dihydropyridin-1-yl, etc.), tetrahydropyridyl (e.g. 1,2,3,6-tetrahydropyridin-1-yl, etc.) dihydropyrimidinyl (e.g. 1,2-dihydropyrimidin-1-yl, etc.), dihydropyridazinyl (e.g. 2,3-dihydropyridazin-2-yl, 1,4-dihydropyridazin-1-yl, etc.), tetrahydropyridazinyl (e.g. 2,3,4,5-tetrahydropyridazin-2-yl, etc.) triazolyl (e.g. 4H-1,2,4-triazol-4-yl, 1H-1,2,3-triazol-1-yl, 2H-1,2,3-triazol-2-yl, etc.), tetrazol (e.g. 1H-tetrazol-1-yl, 2H-tetrazol-2-yl, etc.), etc.;

unsaturated condensed heterocyclic amino group containing 1 to 4 nitrogen atom(s), for example, 1-indolyl, 2-isoindolyl, benzimidazol-1-yl, dihydroquinolyl, (e.g. 1,2-dihydroquinolin-1-yl, etc.) indazolyl, (e.g. 1H-indazol-1-yl, etc.), benzotriazolyl (e.g. 1H-benzotriazol-1-yl, etc.), etc.;

unsaturated 3 to 8-membered (more preferably 5 or 6-membered) heteromonocyclic group containing 1 to 2 oxygen atom(s) and 1 to 3 nitrogen atom(s), for example, dihydroxazolyl (e.g. 2,3-dihydroxazol-3-yl, etc.) dihydroisoxazolyl (e.g. 2,5-dihydroisoxazol-2-yl, etc.), etc.;

unsaturated condensed heterocyclic amino group containing 1 to 2 oxygen atom(s) and 1 to 3 nitrogen atom(s), for example, 2,3-dihydrobenzoxazol-3-yl, 2,3-dihydrobenz[d][1,2,3]oxadiazol-2-yl, etc.;

unsaturated 3 to 8-membered (more preferably 5 or 6-membered) heteromonocyclic amino group containing 1 to 2 sulfur atom(s) and 1 to 3 nitrogen atom(s), for example, dihydrothiazolyl (e.g. 2,3-dihydrothiazol-3-yl, etc.) dihydrothiadiazolyl (e.g. 2,3-dihydro-1,2,3-thiadiazol-2-yl, 4,5-dihydro-1,2,4-thiadiazol-4-yl, 3,4-dihydro-1,3,4-thiadiazol-3-yl, 2,3-dihydro-1,2,5-thiadiazol-2-yl, etc.), dihydrothiazinyl (e.g. 2,3-dihydro-4H-1,4-thiazin-4-yl, etc.), etc.;

unsaturated condensed heterocyclic amino group containing 1 to 2 sulur atom(s) and 1 to 3 nitrogen atom(s), for example, dihydrobenzothiazolyl (e.g. 2,3-dihydrobenzothiazol-3-yl, etc.), tetrahydrobenzothiadiazolyl (e.g. 2,3,4,5-tetrahydrobenzo[d][1,2,3]-thiadiazol-2-yl, etc.), dihydroimidazothiadiazolyl (e.g. 3,4-dihydro-2H-imidazo[2,1-b][1,3,4]thiadiazol-3-yl, etc.), etc.; in which the preferred one may be unsaturated 3 to 8-membered heteromonocyclic amino group containing 1 to 4 nitrogen atom(s) and unsaturated condensed heterocyclic amino group containing 1 to 2 sulfur atom(s) and 1 to 3 nitrogen atom(s), the more preferred one may be dihydropyridazinyl, tetrahydropyridazinyl, dihydropyrimidinyl, dihydropyridyl, tetrahydropyridyl and pyrazolyl, and the most preferred one may be 2,3-dihydropyridazin-2-yl, 1,4-dihydropyridazin-1-yl, 2,3,4,5-tetrahydropyridazin-2-yl, 1,2-dihydropyrimidin-1-yl, 1,2-dihydropyridin-1-yl, 1,4-dihydropyridin-1-yl, 1,2,3,6-tetrahydropyridin-1-yl, and pyrazol-1-yl.

Aforesaid "unsaturated cyclic amino group" may have one or more (preferably 1 to 4) suitable substituent(s) as exemplified above for "suitable substituent(s) of "unsaturated heterocyclic group".

Suitable "a leaving group" may include di(lower)alkylamino (e.g. dimethylamino, diethylamino, N-ethylpropylamino, dibutylamino, N-pentylhexylamino, etc.), lower alkoxy as mentioned above, halogen as mentioned above, lower alkylthio (e.g. methylthio, ethylthio, propylthio, butylthio, pentylthio, hexylthio, etc.), acyloxy such as lower alkanoyloxy (e.g. acetoxy, etc.), sulfonyloxy (e.g. mesyloxy, tosyloxy, etc.) or the like, and the like.

The processes for preparing the object compound (I) of the present invention are explained in detail in the following.

PROCESS 1

The object compound (I) of a salt thereof can be prepared by reacting the compound (II) or a salt thereof with the compound (III) or a salt thereof.

Suitable salt of the compound (II) can be referred to acid addition salt as exemplified for the compound (I).

Suitable salt of the compound (III) can be referred to the ones as exemplified for the compound (I).

This reaction is preferably carried out in a solvent such as acetic acid, benzene, pyridine or any other solvent which does not adversely effect the reaction.

This reaction may be carried out in the presence of an acid such as sulfuric acid, hydrochloric acid, p-toluenesulfonic acid or the like.

The reaction temperature is not critical and the reaction is usually carried out under warming to heating.

PROCESS 2

The object compound (Ia) or a salt thereof can be prepared by reacting the compound (II) of a salt thereof with the compound (IV) or a salt thereof.

Suitable salt of the compound (Ia) can be referred to the ones as exemplified for the compound (I).

Suitable salt of the compound (II) can be referred to an acid addition salt as exemplified for the compound (I).

Suitable salt of the compound (IV) can be referred to the ones as exemplified for the compound (I).

In this reaction, the group $R^3$ (i.e. an acyl group) may be introduced into the compound (IV) during this reaction by carrying out this reaction in the presence of an acylating agent such as lower alkyl haloformate (e.g. methyl chloroformate, ethyl chloroformate, etc.), acid halide (e.g. acetyl chloride, propionyl bromide, etc.).

This reaction is usually carried out in a solvent such as methylene chloride, chloroform, tetrahydrofuran, N,N-dimethylformamide or any other solvent which does not adversely influence the reaction.

The reaction temperature is not critical and the reaction is usually carried out at room temperature, under warming to heating.

There is a case where the group $R^3$ is removed during the reaction, isolation step or purification step, and this case is also included within the scope of the present invention.

PROCESS 3

The object compound (Ib) or a salt thereof can be prepared by subjecting the compound (Ia) or a salt thereof to removal reaction of an acyl group.

Suitable salt of the compound (Ib) can be referred to the ones as exemplified for the compound (I).

The removal reaction of this process can be carried out in the dehydrogenation condition (e.g. potassium t-butoxide in t-butanol, manganese oxide in chloroform, etc.), conventional hydrolysis condition [e.g. alkali metal hydroxide (e.g. sodium hydroxide, potassium hydroxide, etc.) in alcohol (e.g. methanol, ethanol, etc.) and water; or the like.

The reaction condition can be selected according to the kind of the compound (Ia) to be used.

The reaction temperature is not critical and the reaction is usually carried out at room temperature, under warming to heating.

PROCESS 4

The object compound (Id) or a salt thereof can be prepared by subjecting the compound (Ic) or a salt thereof to introduction reaction of lower alkyl which may have one or more suitable substituent(s).

Suitable salt of the compound (Id) can be referred to the ones as exemplified for the compound (I).

The introduction reaction of this process can be carried out by reacting the compound (Ic) or a salt thereof with a reagent for introduction of lower alkyl which may have one or more suitable substituent(s).

Suitable reagent for introduction of lower alkyl which may have one or more suitable substituent(s) can include a compound of the formula:

$$R^4-X$$

[wherein $R^4$ is as defined above and X is a leaving group such as an acyloxy [e.g. lower alkanoyloxy (e.g. formyloxy, acetoxy, propionyloxy, butyryloxy, pivaloyloxy, hexanoyloxy, etc.), sulfonyloxy (e.g. mesyloxy, tosyloxy, etc.), etc.], halogen (e.g. fluoro, chloro, bromo, iodo) or the like]; acyl(lower)alkene in which the double bond is adjacent to acyl group such as acrylic acid and its derivative (e.g. methyl acrylate, ethyl acrylate, etc.), crotonic acid and its derivative (e.g. methyl crotonate, ethyl crotonate, etc.); and the like.

This reaction is usually carried out in a solvent such as diethyl ether, chloroform, methylene chloride, N,N-dimethylformamide, alcohol (e.g. methanol, ethanol, etc.) or any other solvent which does not adversely influence the reaction.

The reaction temperature is not critical and the reaction is usually carried out under cooling, at room temperature, under warming to heating.

The reaction can be carried out in the presence of condensation catalyst (e.g. trimethylbenzylammonium hydroxide, etc.).

PROCESS 5

The object compound (If) of a salt thereof can be prepared by subjecting the compound (Ie) or a salt thereof to removal reaction of carboxy protective group.

Suitable salts of the compounds (Ie) and (If) can be referred to the ones as exemplified for the compound (I).

This reaction is carried out in accordance with a conventional method such as hydrolysis or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

PROCESS 6

The object compound (Ig) or a salt thereof can be prepared by subjecting the compound (V) or a salt thereof to formation reaction of pyridazinone ring.

Suitable salts of the compounds (Ig) and (V) can be referred to acid addition salts as exemplified for the compound (I).

The formation reaction of this process can be carried out, for example, by reacting the compound (V) or a salt thereof with glyoxalic acid or its reactive derivative or a salt thereof and hydrazine or a salt thereof.

Suitable salt of glyoxalic acid can be referred to a salt with a base as exemplified for the compound (I).

Suitable salt of hydrazine can be referred to an acid addition salt as exemplified for the compound (I).

Suitable reactive derivative of glyoxalic acid may be the ones conventionally used in this field of the art such as an activated ester thereof.

The reaction can be carried out in the presence or absence of a solvent.

The reaction temperature is not critical and the reaction is usually carried out under warming to heating.

PROCESS 7

The object compound (Ih) or a salt thereof can be prepared by reacting the compound (VI) or a salt thereof with the compound (VII) or a salt thereof.

Suitable salts of the compounds (Ih), (VI) and (VII) can be referred to acid addition salt as exemplified for the compound (I).

This reaction can be carried out, for example, according to the procedure as disclosed in Example 15.

PROCESS 8

The object compound (Ii) or a salt thereof can be prepared by reacting the compound (VIII) or a salt thereof with the compound (IX) or its reactive derivative at methyl group or a salt thereof.

Suitable salts of the compounds (Ii), (VIII) and (IX) can be referred to acid addition salt as exemplified for the compound (I).

This reaction can be carried out, for example, according to the procedure as disclosed in Example 16.

Suitable reactive derivative at methyl group of the compound (IX) may be its pyridinium derivative of the like.

PROCESS 9

The object compound (Ij) or a salt thereof can be prepared by reacting the compound (X) or a salt thereof with the compound (XI) or a salt thereof.

Suitable salt of the compound (Ij), (X) and (XI) can be referred to acid addition salt as exemplified for the compound (I).

This reaction can be carried out, for example, according to the procedure as disclosed in Example 17.

PROCESS 10

The object compound (Ik) or a salt thereof can be prepared by reacting the compound (XII) or a salt thereof with the compound (XI) or a salt thereof.

Suitable salt of the compound (Ik), (XII) and (XI) can be referred to acid addition salt as exemplified for the compound (I).

This reaction can be carried out, for example, according to the procedure as disclosed in Example 18.

PROCESS 11

The object compound (Il) or a salt thereof can be prepared by reacting the compound (XIII) or a salt thereof with the compound (XIV) or a salt thereof.

Suitable salt of the compounds (Il), (XIII) and (XIV) can be referred to acid addition salt as exemplified for the compound (I).

This reaction can be carried out, for example, according to the procedure as disclosed in Example 19.

PROCESS 12

The object compound (Im) or a salt thereof can be prepared by reacting the compound (XV) or a salt thereof with the compound (XVI) or a salt thereof.

Suitable salt of the compounds (Im), (XV) and (XVI) can be referred to acid addition salt as exemplified for the compound (I).

This reaction can be carried out, for example, according to the procedure as disclosed in Example 20.

PROCESS 13

The object compound (In) or a salt thereof can be prepared by reacting the compound (XV) or a salt thereof with the compound (XVII) or a salt thereof.

Suitable salt of the compounds (In), (XV) and (XVII) can be referred to acid addition salt as exemplified for the compound (I).

This reaction can be carried out, for example, according to the procedure as disclosed in Example 21.

PROCESS 14

The object compound (Io) of a salt thereof can be prepared by reacting the compound (XV) or a salt thereof with the compound (XVIII) or a salt thereof.

Suitable salt of the compounds (Io), (XV) and (XVIII) can be referred to acid addition salt as exemplified for the compound (I).

This reaction can be carried out, for example, according to the procedure as disclosed in Example 23.

PROCESS 15

The object compound (Iq) or a salt thereof can be prepared by subjecting the compound (Ip) or a salt thereof to hydrolysis reaction of cyano group.

Suitable salts of the compounds (Ip) and (Iq) can be referred to the ones as exemplified for the compound (I).

This hydrolysis reaction can be carried out according to a similar manner to that disclosed in the explanation of Process 5.

PROCESS 16

The object compound (Ir) or a salt thereof can be prepared by subjecting the compound (Iq) or a salt thereof to removal reaction of carboxy group.

Suitable salts of the compounds (Iq) and (Ir) can be referred to the ones as exemplified for the compound (I).

This reaction can be carried out, for example, according to the procedure as disclosed in Example 45.

PROCESS 17

The object compound (Is) or a salt thereof can be prepared by subjecting the compound (If) or a salt thereof to amidation reaction.

Suitable salts of the compounds (If) and (Is) can be referred to the ones as exemplified for the compound (I).

This reaction can be carried out by reacting the compound (If) or a salt thereof with an amidation reagent such as ammonia, di(lower)alklamine wherein two lower alkyl groups may bond to each other to form 3 to 6-membered ring (e.g. dimethylamine, N-methylethylamine, diethylamine, dipropylamine, N-butyl-t-butylamine, dipentylamine, N-pentylhexylamine, aziridine, azetidine, pyrrolidine, piperidine, etc.) or the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (If) is used in a free acid form or its salt form, the reaction is preferably carried out in the presence of a conventional condensing agent such as N,N'-dicyclohexylcarbodiimide; or the like.

The reaction may also be carried out in the presence of an inorganic or organic base such as an alkali metal carbonate, alkali metal bicarbonate, tri(lower)alkylamine (e.g. triethylamine, etc.), pyridine N-(lower)alkylmorpholine, N,N-di(lower)alkylbenzylamine, or the like.

The reaction temperature is not critical, and the reaction is usually carried out under cooling to warming.

PROCESS 18

The object compound (Iu) or a salt thereof can be prepared by subjecting the compound (It) or a salt thereof to conversion reaction of amino group to oxo group.

Suitable salts of the compounds (It) and (Iu) can be referred to the ones as exemplified for the compound (I).

This reaction can be carried out, for example, according to the procedure as disclosed in Example 52.

PROCESS 19

The object compound (Iv) or a salt thereof can be prepared by subjecting the compound (Iu) or a salt thereof to removal reaction of carboxy group.

Suitable salt of the compounds (Iu) and (Iv) can be referred to the ones as exemplified for the compound (I).

This reaction can be carried out, for example, according to the procedure as disclosed in Example 54.

PROCESS 20

The object compound (Iw) or a salt thereof can be prepared by reacting the compound (Iv) or a salt thereof with the compound (XIX) or a salt thereof.

Suitable salts of the compounds (Iv) and (Iw) can be referred to the ones as exemplified for the compound (I).

Suitable salt of the compound (XIX) can be referred to acid addition salt as exemplified for the compound (I).

This reaction can be carried out, for example, according to the procedure as disclosed in Example 57.

PROCESS 21

The object compound (Ix) or a salt thereof can be prepared by subjecting the compound (Iv) or a salt thereof to conversion reaction of halogen to lower alkoxy.

Suitable salt of the compounds (Iv) and (Ix) can be referred to the ones as exemplified for the compound (I).

This reaction can be carried out, for example, according to the procedure as disclosed in Example 58.

PROCESS 22

The object compound (Iu) or a salt thereof can be prepared by subjecting the compound (Ix) or a salt thereof to conversion reaction of lower alkoxy to oxo group.

Suitable salt of the compounds (Iu) and (Ix) can be referred to the ones as exemplified for the compound (I).

This reaction can be carried out, for example, according to the procedure as disclosed in Example 62.

PROCESS 23

The object compound (Iy) or a salt thereof can be prepared by reacting the compound (XX) or a salt thereof with the compound (XXI) and ammonia.

Suitable salts of the compounds (Iy) and (XX) can be referred to acid addition salt as exemplified for the compound (I).

This reaction can be carried out, for example, according to the procedure as disclosed in Example 99.

The object compound (I) and a salt thereof possess various actions as stated above and useful as stated before.

The object compound (I) and a salt thereof have high solubility into water and are advantageous in preparing a pharmaceutical preparation.

In order to illustrate the usefulness of the object compound (I), the test results on diuretic activity of the representative compounds of the present invention are shown in the following.

Test on Diuretic Activity (1)

1. Test compound
3-[2-(2-Carboxyethyl)-3-oxo-2,3-dihydropyridazin-6-yl]-2-phenylpyrazolo[1,5-a]pyridine 2. Test Method
Male JCL:SD strain rats aged 6 weeks and weighing about 200 g were used after starving for 18 hours. Immediately after oral dosing with the test compound suspended in 0.5% methylcellulose (0.5% MC), the animals were given 20 ml/kg physiological saline orally. The rats were housed by threes in a metabolism cage. The urine was collected for 3 hours. Urinary electrolyte ($Na^+$) was measured with a Stat/Ion® System (Technichon). The tests were conducted in 3 groups of 3 animals each.

3. Test Result
The urinary electrolyte ($Na^+$) (%, control=100%) was shown in the following table.

| Dose (mg/kg) | $Na^+$ |
|---|---|
| 10.0 | 244 |

Test on Diuretic Activity (2)

1. Test Compound
Sodium salt of 3-[2-(3-carboxypropyl)-3-oxo-2,3-dihydropyridazin-6-yl]-2-phenylpyrazolo[1,5-a]pyridine 2. Test Method
Male JCL:SD strain rats aged 6 weeks and weighing about 200 g were used after starving for 18 hours. Immediately after oral dosing with the test compound suspended in 0.5% methylcellulose (0.5% MC), the animals were given 20 ml/kg physiological saline orally. The rats were housed by threes in a metabolism cage. The urine was collected for 6 hours. Urinary electrolyte ($Na^+$) was measured with a Stat/Ion® System (Technichon). The tests were conducted in 3 groups of 3 animals each.

3. Test Result
$ED_{100}$ value (mg/kg) was as follows.
$ED_{100}=0.31$

Test on Adenosine Antagonism (1)

1. Test compound
Sodium salt of 3-[2-(3-carboxypropyl)-3-oxo-2,3-dihydropyridazin-6-yl]-2-phenylpyrazolo[1,5-a]pyridine 2. Test Method
Male Hartley strain guinea-pigs, weighing 500–650 g, were killed by bleeding and the hearts were removed. An atrial strip was removed and suspended in an organ bath containing 50 ml of Tyrode's solution maintained at 27°–30° C. and aerated with a gas mixture of 95% $O_2$–5% $CO_2$. The atrium was connected to a strain gauge under an initial tension of 0.4–0.6 g. After constant motility had been obtained, the test compound and the adenosine ($1 \times 10^{-5}$M) were added. The negative inotropic activity of the adenosine was compared in the absence or presence of the test compound and then the adenosine antagonistic activities were measured. Adenosine antagonistic activities were expressed as $IC_{50}$ values.

3. Test Results
$IC_{50}=2.4 \times 10^{-9}$

Test on Adenosine Antagonism (2)

1. Test Compound
Sodium salt of 3-[2-(3-carboxypropyl)-3-oxo-2,3-dihydropyridazin-6-yl]-2-phenylpyrazolo[1,5-a]pyridine 2. Test Method
(1) A1 binding
Preparation of brain tissue homogenates
Rat brain homogenates were used to measure A1-receptor binding activity. Brain obtained from male Sprague-Dawley rats, weighing 200–300 g, were homogenized in 20 volumes (w/v) of 50 mM Tris-HCl buffer (pH 7.4 at 25° C.) using a Polytron homogenizer (KINEMATICA GmbH). The homogenate was centrifuged at $41000 \times g$ at 4° C. for 30 minutes and resultant pellets resuspended in 20 volumes buffer (50 mM, pH 7.4). Adenosine deaminase was added (2 I.U./ml) and then incubated at 37° C. for 30 minutes to remove endogenous adenosine. The treated homogenate was then recentrifuged and the resultant pellets were frozen at −70° C. until the time of assay.

[$^3$H]-N$^6$-cyclohexyladenosine ($^3$H-CHA) A1 Binding

The activity of each compound was assessed in three separate experiments. All assays were run in duplicate in a final volume of 1 ml containing 1 nM $^3$H-CHA with a specific activity of 25 Ci/mmol. Nonspecific binding was determined in the presence of 10 μM CHA. Reactions were initiated by the addition of the adenosine deaminase treated homogenates at a final protein concentration of 200 to 300 μg/ml, and this mixture was incubated at 23° C. for 3 hours. After incubation the bound radioactivity was isolated by filtration under vacuum over Whatman GF/B glass fiber filter strips and unbound radioactivity was removed with 2×5 ml washes of ice-cold buffer. Filters were removed from the strip and placed in glass vials to which 10 ml of Aquasol II (NEN Research Products) were added. After equilibration for at least 12 hours, radioactivity was determined by conventional liquid scintillation spectroscopy.

(2) A2 Binding

Preparation of striatal homogenates

Striata obtained from male Sprague-Dawley rats were homogenized in 20 volumes (W/V) of 50 mM Tris-HCl buffer (pH 7.4 at 25° C.) containing 10 mM MgCl$_2$, using Polytron homogenizer. The homogenate was centrifuged at 41000×g at 4° C. for 30 minutes and the resultant pellet resuspended in 20 volumes buffer (50 mM, pH 7.4). Adenosine deaminase was added (2 I.U./ml) and then incubated at 37° C. for 30 minutes to remove endogenous adenosine. The treated homogenate was then recentrifuged and the resultant pellets were frozen at −70° C. until the time of assay.

[$^3$H]-5'-(N-ethylcarboxamido)adenosine ($^3$H-NECA) A2 Binding

The activity of each compound was assessed in at least three separate experiments. All assays were run in duplicate in a final volume of 1 ml containing 5 nM $^3$H-NECA with a specific activity of 20.8 Ci/mmol. CPA (50 nM) was added to eliminate the A1 component. Non-specific binding was determined in the presence of 20 μM NECA. Reactions were initiated by the addition of the adenosine deaminase treated homogenate at a final protein concentration of 200 to 300 μg/ml, and this mixture was incubated at 23° C. for 120 minutes. Then, bound radioactivity was isolated and measured by the same procedure as described in $^3$H-CHA binding.

3. Test Results

| IC$_{50}$ (nM) | |
|---|---|
| A1 ($^3$H-CHA) | A2 ($^3$H-NECA) |
| 120 | 5910 |

Test on Protective effect in glycerol-induced renal toxicity in rats

1. Test Compound

Sodium salt of 3-[2-(3-carboxypropyl)-3-oxo-2,3-dihydropyridazin-6-yl]-2-phenylpyrazolo[1,5-a]pyridine 2. Test Method Male Sprague-Dawley rats (weighing 290-310 g) were fasted and dehydrated for 24 hours, acute renal failure was produced by intramuscular injection of 25% V/V glycerol in sterile saline (0.9% W/V NaCl), 10 ml/kg body weight. One hour before the injection of glycerol, rats were given a single oral dose of either test compound (1 mg/kg) or vehicle (5 ml/kg of saline). Twenty-four hours after glycerol injection, each rat was anesthetized with ether and blood sample was taken from abdominal aorta for the determination of plasma creatinine and BUN (blood urine nitrogen).

3. Test Results

| Group | BUN (mg/dl) (mean ± S.E.) | Plasma creatinine (mg/dl) (mean ± S.E.) |
|---|---|---|
| vehicle (saline) | 35.6 ±3.3 | 1.62 ±0.07 |
| Test Compound (1 mg/kg) | 27.6* ±1.6 | 1.38* ±0.15 |

*: 0 < 0.05

The pharmaceutical composition of this invention can be used in the form of a pharmaceutical preparation, for example, in solid, semisolid or liquid form, which contains the pyrazolopyridine compound (I) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used. The pyrazolopyridine compound (I) or a pharmaceutical acceptable salt thereof is/are included in the pharmaceutical composition in an amount sufficient to produce the desired aforesaid pharmaceutical effect upon the process or condition of diseases.

For applying the composition to human being or animals, it is preferable to apply it by intravenous, intramuscular, pulmonary, or oral administration, or insufflation. While the dosage of therapeutically effective amount of the pyrazolopyridine compound (I) varies from and also depends upon the age and condition of each individual patient to be treated, in the case of intravenous administration, a daily dose of 0.01–20 mg of the pyrazolopyridine compound (I) per kg weight of human being or animals, in the case of intramuscular administration, a daily dose of 0.1–20 mg of the pyrazolopyridine compound (I) per kg weight of human being or animals, in case of oral administration, a daily dose of 0.5–50 mg of the pyrazolopyridine compound (I) per kg weight of human being or animals is generally given for the prevention and/or treatment of aforesaid diseases.

The following Preparations and Examples are given for the purpose of illustrating the present invention in more detail.

EXAMPLE 1

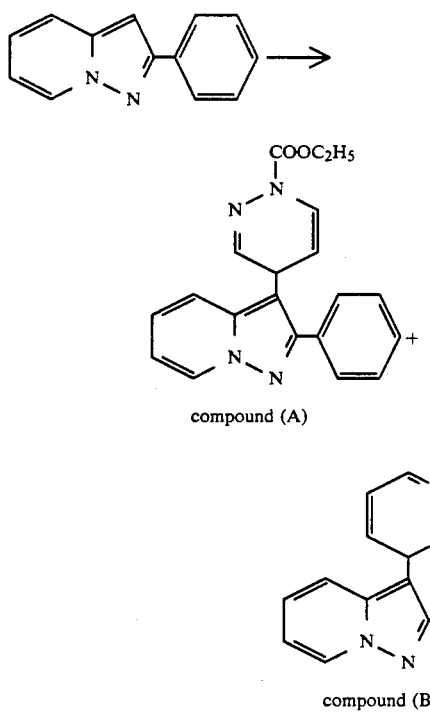

compound (A)

compound (B)

Ethyl chloroformate (3.38 g) was added dropwise with stirring to a solution of 2-phenylpyrazolo[1,5-a]pyridine (2.54 g) and pyridazine (5.00 g) in methylene chloride (5.0 ml) at 10° C. After being stirred at 10° C. for 1 hour and then at room temperature for 2 hours, the reaction mixture was poured onto ice-water (100 ml), and extracted with ethyl acetate. The combined extracts were washed with saturated sodium chloride aqueous solution (100 ml), dried over magnesium sulfate and evaporated in vacuo. The residue was chromatographed on silica gel (150 g) with a mixture of chloroform and n-hexane (1:1) as an eluant. The fractions containing main-product [compound (A)] were combined and evaporated in vacuo to give 3-(1-ethoxycarbonyl-1,4-dihydropyridazin-4-yl)-2-phenylpyrazolo[1,5-a]pyridine (2.42 g).

mp: 173°-174° C.

IR (Nujol): 1740, 1700, 1670, 1635, 1615 cm$^{-1}$

NMR (CDCl$_3$, δ): 1.40 (3H, t, J=7.0 Hz), 4.43 (2H, q, J=7.0 Hz), 4.48-4.70 (1H, m), 5.03 (1H, dt, J=8.5 Hz and 3.0 Hz), 6.67-7.82 (10H, m), 8.50 (1H, dd, J=7.0 Hz and 1.0 Hz)

The fractions containing by-product [compound (B)] were combined and evaporated in vacuo to give 3-(2-ethoxycarbonyl-2,3-dihydropyridazin-3-yl)-2-phenylpyrazolo[1,5-a]pyridine (0.39 q).

mp: 150°-152° C.

IR (Nujol): 1720, 1635 cm$^{-1}$

NMR (CDCl$_3$, δ): 1.16 (3H, t, J=7.0 Hz), 4.18 (2H, q, J=7.0 Hz), 5.67-7.95 (12H, m), 8.48 (1H, dd, J=7.0 Hz and 1.0 Hz)

EXAMPLE 2

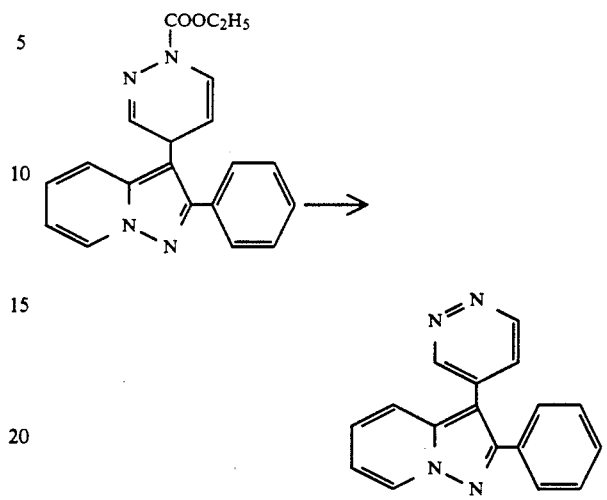

Air was bubbled into a mixture of 3-(1-ethoxycarbonyl-1,4-dihydropyridazin-4-yl)-2-phenylpyrazolo[1,5-a]pyridine (1.12 g) and potassium tert-butoxide (1.81 g) in tert-butanol (25 ml) at 50° C. for 10 minutes.

tert-Butanol was evaporated in vacuo and ice-water (50 ml) was added to the residue. The mixture was extracted with chloroform (30 ml, 3 times). The combined extracts were washed with saturated sodium chloride aqueous solution (50 ml), dried over magnesium sulfate and evaporated in vacuo. The residue was chromatographed on silica gel (20 g) with chloroform as an eluant. The fractions containing the object compound were combined and evaporated in vacuo to give 3-(pyridazin-4-yl)-2-phenylpyrazolo[1,5-a]pyridine (0.35 g).

mp: 204°-205° C.

IR (Nujol): 1630, 1580, 1515 cm$^{-1}$

NMR (DMSO-d$_6$, δ): 6.97-8.00 (9H, m), 8.85 (1H, d, J=7.0 Hz), 9.03-9.27 (2H, m)

Analysis Calcd. for C$_{17}$H$_{12}$N$_4$: C 74.98, H 4.44, N 20.58; Found: C 75.27, H 4.63, N 20.38

EXAMPLE 3

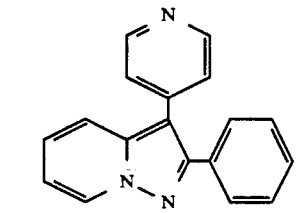

3-(Pyridin-4-yl)-2-phenylpyrazolo[1,5-a]pyridine was prepared according to the similar manners to those of Example 1 and 2.

mp: 166°-167° C.

IR (Nujol): 1630, 1600, 1530 cm$^{-1}$

NMR (CDCl$_3$, δ): 6.83 (1H, dt, J=1.5 Hz and 7.0 Hz), 7.20-7.83 (9H, m), 8.45-8.83 (3H, m)

Analysis Calcd. for C$_{18}$H$_{13}$N$_3$: C 79.68, H 4.83, N 15.49; Found: C 80.20, H4.86, N 15.56

EXAMPLE 4

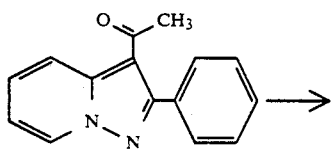

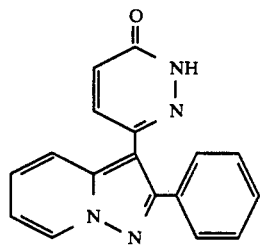

A mixture of 3-acetyl-2-phenylpyrazolo[1,5-a]pyridine (40.00 g) and glyoxalic acid monohydrate (20.27 g) were stirred and heated at 100° C. for 2.5 hours. The reaction mixture was dissolved in a mixture of ethyl acetate (220 ml) and aqueous sodium hydroxide (12%; 220 ml). The aqueous layer was washed with 100 ml of chloroform, then acidified by 10% aqueous hydrochloric acid. That was extracted with chloroform (150 ml×2). The extracts were combined, washed with saturated aqueous solution of sodium chloride. The solvent was evaporated and the residue (39.8 g) was dissolved in aqueous solution of ammonia (120 ml) and to the solution hydrazine monohydrate (42 g) was added. That mixture was refluxed for 2 hours. The precipitates were collected by filtration to give 3-(3-oxo-2,3-dihydropyridazin-6-yl)-2-phenylpyrazolo[1,5-a]pyridine (14.45 g).

mp: 212°–214° C.

IR (Nujol): 1660, 1625, 1580, 1510 cm$^{-1}$

NMR (CDCl$_3$, δ): 6.87 (1H, d, J=11 Hz), 7.00 (1H, td, J=7 Hz and 1 Hz ), 7.08 (1H, d, J=11 Hz), 7.23–7.73 (6H, m), 7.83 (1H, d, J=8 Hz), 7.77 (1H, d, J=7 Hz)

Analysis Calcd. for C$_{17}$H$_{12}$N$_4$O: C 70.82, H 4.20, N 19.43; Found: C 70.75, H 4.83, N 19.24

EXAMPLE 5

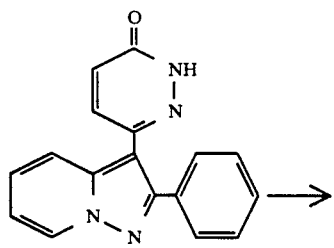

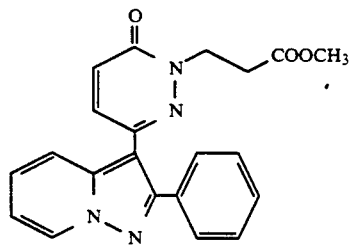

A mixture of 3-(3-oxo-2,3-dihydropyridazin-6-yl)-2-phenylpyrazolo[1,5-a]pyridine (0.43 g), methyl acrylate (1.29 g), 40% methanolic trimethylbenzylammonium hydroxide (0.4 ml) and methanol (2 ml) in chloroform (8 ml) was refluxed for 40 minutes and then evaporated in vacuo. To the residue were added methylene chloride (30 ml) and water (30 ml), and the organic layer was separated, dried over magnesium sulfate and evaporated in vacuo. The crystalline residue was recrystallized from a mixture of ethyl acetate and diethyl ether to give 3-[2-(2-methoxycarbonylethyl)-3-oxo-2,3-dihydropyridazin-6-yl]-2-phenylpyrazolo[1,5-a]pyridine (0.37 g).

mp: 133° to 133.5° C.

IR (Nujol): 1730, 1660, 1585 cm$^{-1}$

NMR (CDCl$_3$, δ): 2.90 (2H, t, J=6 Hz), 3.67 (3H, s), 4.57 (2H, t, J=6 Hz), 6.70 (1H, d, J=9 Hz), 6.87 (1H, t, J=7 Hz), 7.00 (1H, d, J=9 Hz), 7.17–7.73 (6H, m), 8.00 (1H, d, J=9 Hz), 8.50 (1H, d, J=7 Hz)

MS (M$^+$): 374

Analysis Calcd. for C$_{21}$H$_{18}$N$_4$O$_2$: C 67.37, H 4.85, N 14.96; Found: C 67.31, H 5.35, N 14.94

EXAMPLE 6

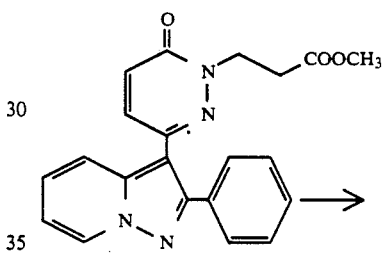

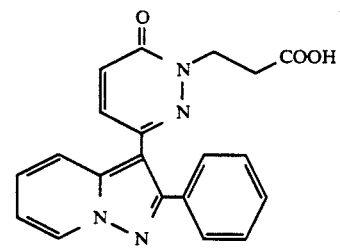

A mixture of 3-[2-(2-methoxycarbonylethyl)-3-oxo-2,3-dihydropyridazin-6-yl]2-phenylpyrazolo[1,5-a]pyridine (1.94 g) and 24% aqueous sodium hydroxide (2 ml) in methanol (8 ml) was refluxed for 30 minutes and then evaporated in vacuo. The residue was dissolved in water (30 ml) and the aqueous solution was acidified with hydrochloric acid, and extracted with chloroform (25 ml). The extract was dried over magnesium sulfate and evaporated in vacuo. The residue was recrystallized from a mixture of ethanol and n-hexane to give 3-[2-(2-carboxyethyl)-3-oxo-2,3-dihydropyridazin-6-yl]-2-phenylpyrazolo[1,5-a]pyridine (1.24 g).

mp: 155.5° to 156° C.

IR (Nujol): 1835, 1640, 1570, 1520, 1490 cm$^{-1}$

NMR (CDCl$_3$, δ): 2.97 (2H, t, J=7 Hz), 4.60 (2H, t, J=7 Hz), 6.15–7.00 (1H, broad d), 6.75–7.70 (9H, m), 8.00 (1H, d, J=9 Hz), 8.53 (1H, d, J=7 Hz)

MS (M$^+$): 360

Analysis Calcd. for C$_{20}$H$_{16}$N$_4$O$_3$: C 66.66, H 4.47, N 15.55; Found: C 66.61, H 4.61, N 15.50

EXAMPLE 7

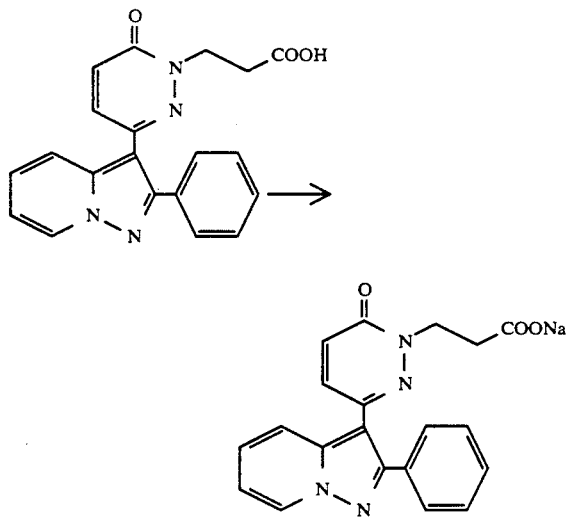

To a mixture of 3-[2-(2-carboxyethyl)-3-oxo-2,3-dihydropyridazin-6-yl]-2-phenylpyrazolo[1,5-a]pyridine (10.0 g), ethanol (100 ml) and water (10 ml) was added a solution of sodium hydroxide (1.11 g) in a mixture of ethanol (40 ml) and water (15 ml). The reaction mixture was refluxed for 2 hours to give a clear solution, then this solution was cooled. The resultant solid was collected by filtration and washed with 85% ethanol (8 ml) and recrystallized twice from 83% ethanol (48 ml) to give crystals of sodium salt of 3-[2-(2-carboxyethyl)-3-oxo-2,3-dihydropyridazin-6-yl]-2-phenylpyrazolo[1,5-a]pyridine (5.13 g).

mp: 271°-272° C.

IR (Nujol): 3400, 1670, 1610, 1580, 1530 cm$^{-1}$

NMR (DMSO-$d_6$, δ): 2.45 (2H, t, J=8 Hz), 4.29 (2H, t, J=8 Hz), 6.81 (1d, J=9 Hz), 7.02 (1H, d, J=9 Hz), 7.07 (1H, d, J=7 Hz and 1 Hz), 7.40-7.63 (6H, m), 8.02 (1H, d, J=9 Hz), 8.80 (1H, d, J=7 Hz)

MS: 360 (M+)

Analysis Calcd. for $C_{20}H_{15}N_4O_3Na \cdot 3/2H_2O$ (%): C 58.67, H 4.43, N 13.69; Found: C 58.49, H 4.27, N 13.96

PREPARATION 1

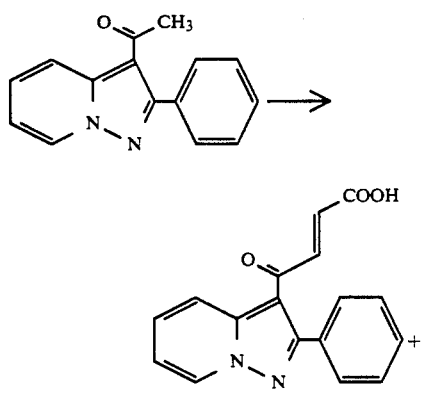

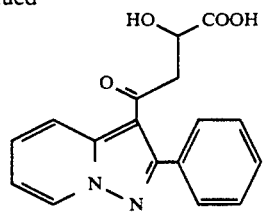

A mixture of glyoxylic acid monohydrate (3.50 g) and 3-acetyl-2-phenylpyrazolo[1,5-a]pyridine (5.00 g) was stirred and heated at 100° C. for 4 hours. The warm reaction mixture was dissolved in methylene chloride (50 ml), and then extracted with 1N aqueous solution of sodium hydroxide (50 ml). The aqueous layer was washed with methylene chloride (total 200 ml) and then with ethyl acetate (total 200 ml). The aqueous solution was adjusted to pH 4~5 with 10% hydrochloric acid. The isolated oil was extracted with chloroform. The extract was evaporated in vacuo and crystallized from methylene chloride to give 4-oxo-4-(2-phenylpyrazolo[1,5-a]pyridin-3-yl)crotonic acid (0.46 g).

mp: 205°-206° C.

IR (Nujol): 1690, 1650, 1630, 1500 cm$^{-1}$

NMR (DMSO-$d_6$, δ): 2.77-3.63 (1H, broad), 6.33 (1H, d, J=16 Hz), 6.87 (1d, J=16 Hz), 7.15 (1H, td, J=7 Hz and 1 Hz), 7.27-7.73 (6H, m), 8.18 (1H, d, J=9 Hz), and 8.80 (1H, d, J=7 Hz)

MS: 292

The aqueous layer of the last extract was acidified to pH 1 and extracted with a mixture of chloroform and methanol (10:1). The organic layer was evaporated in vacuo. The residue was purified by silica gel column chromatography using a mixture of methanol and chloroform as an eluent to give 4-oxo-4-(2-phenylpyrazolo[1,5-a]pyridin-3-yl)-2-hydroxybutyric acid (0.06 g).

mp: 225° C. (decomp)

IR (Nujol): 3350, 1635, 1600, 1495 cm$^{-1}$

NMR (DMSO-$d_6$, δ): 2.53-3.06 (3H, m), 4.06-4.30 (2H, m), 7.03 (1H, t, J=7 Hz), 7.20-7.70 (6H, m), 8.13 (1H, d, J=9 Hz), 8.70 (1H, d, J=7 Hz)

MS: 292 (M-18)

PREPARATION 2

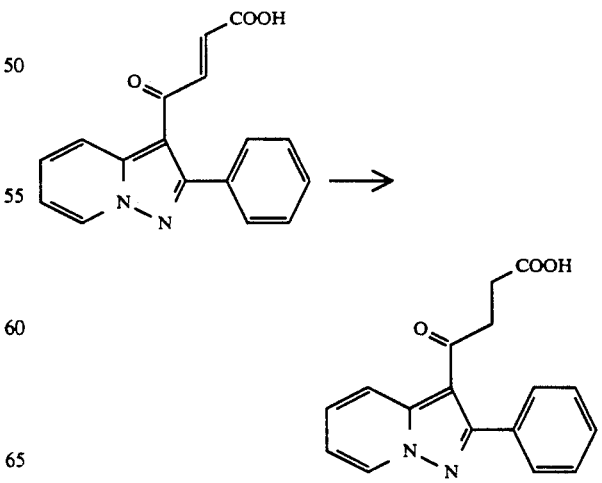

A mixture of 4-oxo-4-(2-phenylpyrazolo[1,5-a]pyridin-3-yl)crotonic acid (3.61 g), zinc powder (5.0 g) and acetic acid (50 ml) was heated at 100° C. for 1.5 hours. The zinc powder was filtered off and washed with acetic acid. The filtrate and washings were combined and evaporated in vacuo. To the residue a saturated aqueous solution of sodium hydrogen carbonate (50 ml) was added and extracted with ethyl acetate (50 ml×2). The combined extracts were washed with a saturated aqueous solution of sodium chloride (50 ml), dried over magnesium sulfate and evaporated in vacuo. The residue was recrystallized from ethanol to give crystals of 4-oxo-4-(2-phenylpyrazolo[1,5-a]pyridine-3-yl)butyric acid (1.65 g).

mp: 167°-168° C.

IR (Nujol): 1705, 1640, 1620, 1500 cm$^{-1}$

NMR (DMSO-d$_6$, δ): 3.17-3.87 (4H, m), 7.18 (1H, t, J=7 Hz), 7.43-7.80 (6H, m), 8.27 (1H, d, J=9.0 Hz), 8.85 (1H, d, J=7.0 Hz)

Analysis Calcd. for $C_{17}H_{14}N_2O_3$ (%): C 69.37, H 4.80, N 9.52; Found: C 69.63, H 4.51, N 9.63

Preparation 3

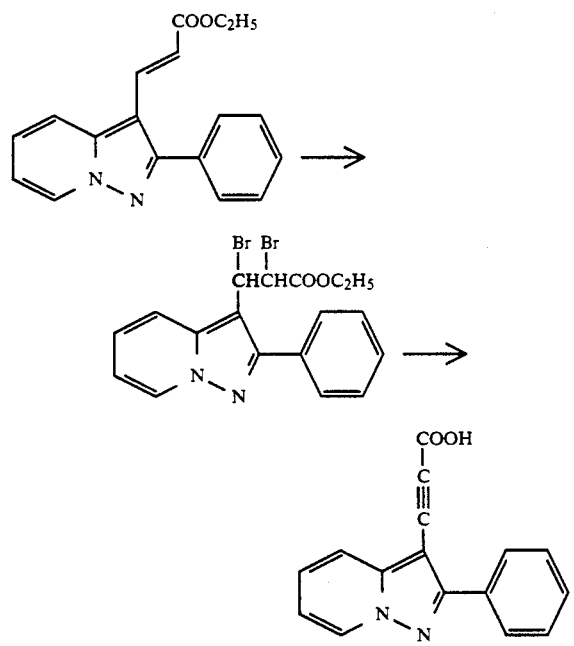

Bromine (13.86 g) was added dropwise to a solution of ethyl 3-(2-phenylpyrazolo[1,5-a]pyridin-3-yl)acrylate (trans isomer) (25.30 g) in methylene chloride (250 ml) under ice-cooling with stirring. After being stirred for 2 hours, the reaction mixture was washed with an aqueous solution of sodium thiosulfate and saturated aqueous solution of sodium sulfate, dried over magnesium sulfate and evaporated in vacuo. The residue was recrystallized from ethyl acetate to give crystals of ethyl 2,3-dibromo-3-(2-phenylpyrazolo[1,5-a]pyridin-3-yl)propionate (26.33 g). This compound (13.80 g) was added to a solution of potassium hydroxide (85%, 9.09 g) in 95% ethanol (50 ml) at 70° C. with stirring. The reaction mixture was heated under reflux for 6 hours. Ethanol was evaporated in vacuo. Water was added to the residue and the mixture was acidified with concentrated hydrochloric acid. The precipitates were collected by filtration, washed with ethanol and dried to give crystals of 3-(2-phenylpyrazolo[1,5-a]pyridin-3-yl)propiolic acid (3.35 g).

mp: <250° C.

IR (Nujol): 2200, 1685, 1630 cm$^{-1}$

NMR (DMSO-d$_6$, δ): 7.08-8.43 (8H, m), 8.93 (1H, d, J=7.5 Hz)

MS: 262 (M+)

PREPARATION 4

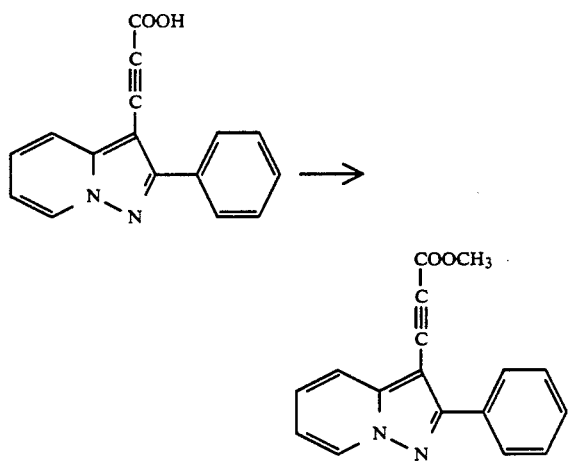

3-(2-Phenylpyrazolo[1,5-a]pyridin-3-yl)propiolic acid (10.33 g) was added to a mixture of sodium hydroxide (3.15 g) and 95% ethanol (103 g), and then dimethyl sulfate (4.97 g) was added to the mixture. The reaction mixture was heated at 60° to 80° C. for 3 hours and 20 minutes. Ethanol was evaporated in vacuo. Water was added to the residue and extracted with chloroform (50 ml×3). Combined extract was washed with a saturated aqueous solution of sodium chloride (50 ml), dried over magnesium sulfate and evaporated in vacuo. The residue was recrystallized from ethyl acetate to give crystals of methyl 3-(2-phenylpyrazolo[1,5-a]pyridin-3-yl)propiolate (5.25 g).

mp: 145°-148° C.

IR (Nujol): 2190, 1700, 1630 cm$^{-1}$

NMR (DMSO-d$_6$, δ): 3.78 (3H, s), 7.13 (1H, t, J=6.5 Hz), 7.42-8.25 (7H, m), 8.83 (1H, d, J=6.5 Hz)

Analysis Calcd. for $C_{17}H_{12}N_2O_2$ (%): C 73.90, H 4.38, N 10.14; Found: C 73.94, H 4.36, N 10.17

PREPARATION 5

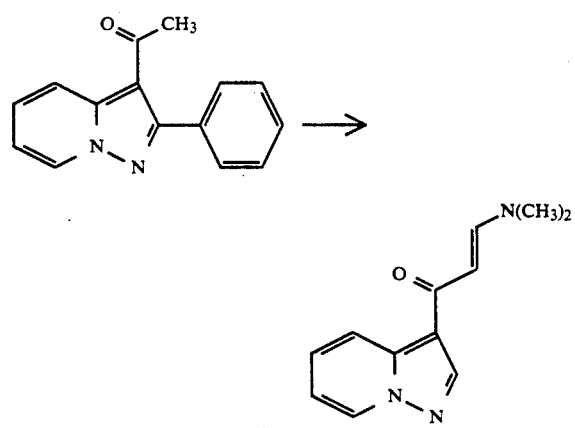

A mixture of 3-acetyl-2-phenylpyrazolo[1,5-a]pyridine (2.36 g), N,N-dimethylformamide dimethyl acetal (11.19 g) and 1,8-diazabicyclo[5.4.0]-7-undecene (1.50 g) was refluxed for 18 hours, and then the solvent was evaporated. To the residue, water (30 ml) was added. The solution thus obtained was extracted with chloroform (30 ml). The organic layer was evaporated. The residue was subjected to column chromatography on alumina (25 g) and eluted with a mixture of chloroform and n-hexane. The fractions containing the object compound were combined and concentrated in vacuo. The residue was recrystallized from chloroform and n-hexane to give 3-(3-N,N-dimethylaminoacryloyl)-2-phenylpyrazolo[1,5-a]pyridine (0.90 g).

mp: 102°-102.5° C.

IR (Nujol): 1620, 1585, 1540, 1500 cm$^{-1}$

NMR (CDCl$_3$, δ): 2.67 (6H, s), 5.02 (1H, d, J=13 Hz), 6.75 (1H, td, J=7 Hz and 1 Hz), 7.15-7.79 (6H, m), 8.33 (1H, d, J=8 Hz), 8.42 (1H, d, J=7 Hz)

MS: 291 (M$^+$)

PREPARATION 6

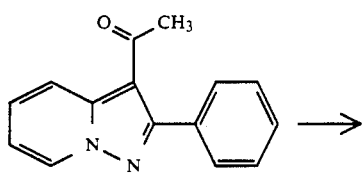 →

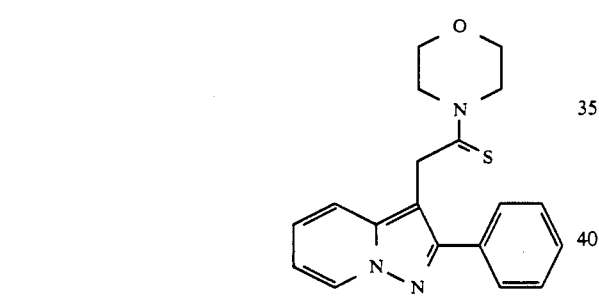

A mixture of 3-acetyl-2-phenylpyrazolo[1,5-a]pyridine (5.40 g), sulfur powder (2.20 g) and morpholine (10.8 ml) was refluxed for 24 hours. The reaction mixture was evaporated in vacuo and the residue was chromatographed on silica gel (80 g) and n-hexane-ethyl acetate (2:1) as an eluent. The fractions containing the object compound were combined and evaporated in vacuo to give 3-(2-morpholino-2-thioxoethyl)-2-phenylpyrazolo[1,5-a]pyridine. One recrystallization from a mixture of ethyl acetate and 2-propanol gave the crystals (5.50 g).

mp: 120°-122° C.

IR (Nujol): 1630, 1530 cm$^{-1}$

NMR (CDCl$_3$, δ): 3.05 (2H, t, J=5 Hz), 3.28 (2H, t, J=5.0 Hz), 3.58 (2H, t, J=5.0 Hz), 4.25 (2H, t, J=5.0 Hz), 4.53 (2H, s), 6.74 (1H, t, J=7.0 Hz), 7.10 (1H, t, J=7.0 Hz), 7.35-7.70 (5H, m), 8.05 (1H, d, J=9.0 Hz), 8.42 (1H, d, J=7.0 Hz)

MS: 334 (M$^+$), 203

Analysis Calcd. for C$_{19}$H$_{17}$N$_3$OS (%): C 67.63, H 5.68, N 12.45; Found: C 67.87, H 5.75, N 12.46

PREPARATION 7

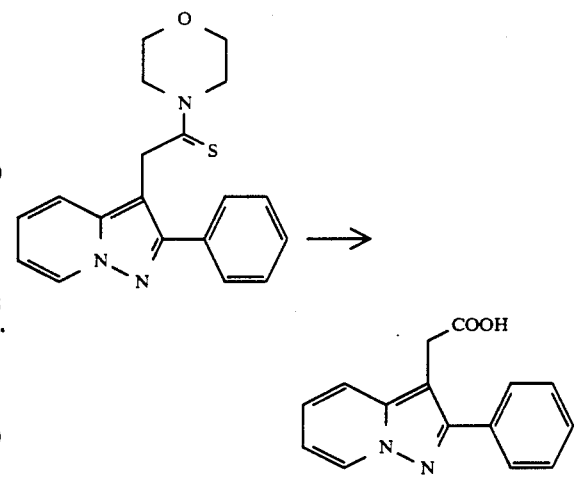

A mixture of 3-(2-morpholino-2-thioxoethyl)-2-phenylpyrazolo[1,5-a]pyridine (5.50 g), potassium hydroxide (85%, 6.45 g) and water (44 ml) was refluxed for 14 hours. After cooling, the reaction mixture was poured onto ice (110 g) and acidified with 6N-hydrochloric acid (pH≈2) and the resulting precipitates were collected to give 2-(2-phenylpyrazolo[1,5-a]pyridin-3-yl)acetic acid (4.20 g).

mp: 202°-204° C.

IR (Nujol): 1695, 1635 cm$^{-1}$

NMR (DMF-d$_7$, δ): 3.85 (2H, s), 6.90 (1H, t, J=7.5 Hz), 7.23 (1H, t, J=7.5 Hz), 7.37-8.00 (6H, m), 8.65 (1H, d, J=7.5 Hz)

MS: 252 (M$^+$), 221, 207

PREPARATION 8

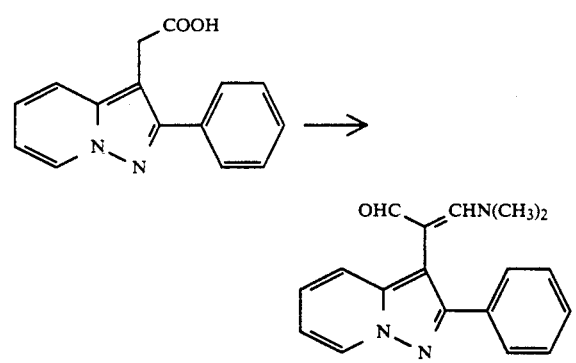

Phosphorus oxychloride (27.6 g) was added dropwise to N,N-dimethylformamide (16.6 ml) for 20 minutes under ice-cooling, 2-(2-phenylpyrazolo[1,5-a]pyridin-3-yl)acetic acid (9.08 g) was added to the solution thus obtained and the reaction mixture was stirred at 90°-100° C. for 20 hours. After cooling, the reaction mixture was poured onto ice (20 g). The mixture was made alkaline with 24% aqueous solution of sodium hydroxide (pH≈9) and stirred at 90° C. for 1 hour and 20 minutes. After cooling, the resulting mixture was extracted with ethyl acetate three times. The combined extract was washed with water and dried over magnesium sulfate. The solvent was removed and recrystallized from a mixture of ethyl acetate and isopropanol to give 3-(N,N-dimethylamino)-2-(2-phenylpyrazolo[1,5-a]pyridine-3-yl)acrylaldehyde (cis and trans mixture) (5.00 g).

mp: 154°-155° C.

IR (Nujol): 2710, 1590, 1580 cm$^{-1}$

NMR (CDCl$_3$, δ): 2.70 (6H, m), 6.70 (1H, t, J=7.5 Hz), 6.90-7.47 (6H, m), 7.70-7.95 (2H, m), 8.40 (1H, d, J=7.5 Hz), 9.19 (1H, s)

MS: 291 (M+), 274, 232, 218

PREPARATION 9

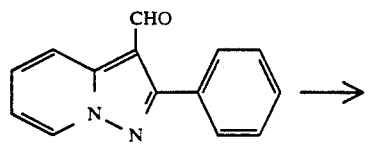

A mixture of 2-phenylpyrazolo[1,5-a]pyridine-3-carbaldehyde (15.0 g), rhodanine (9.44 g), sodium acetate (16.6 g) and glacial acetic acid (90 ml) was refluxed for 10 hours. Water (200 ml) and ethyl acetate (90 ml) were added to the reaction mixture and the resulting precipitates were collected by filtration to give 5-(2-phenylpyrazolo[1,5-a]pyridine-3-yl)methylenerhodanine (cis and trans mixture) (19.8 g).

mp: 312°-314° C.

IR (Nujol): 1685, 1590 cm$^{-1}$

NMR (DMSO-d$_6$, δ): 7.20 (1H, t, J=6.8 Hz), 7.51-7.68 (6H, m), 7.98 (1H, s), 7.95 (1H, d, J=8.9 Hz), 8.91 (1H, d, J=6.9 Hz), 13.6 (1H, broad)

MS: 337 (M+), 250, 218

Analysis Calcd. for C$_{17}$H$_{11}$N$_3$OS$_2$ (%): C 60.52, H 3.29, N 12.45; Found: C 60.58, H 3.25, N 12.38

PREPARATION 10

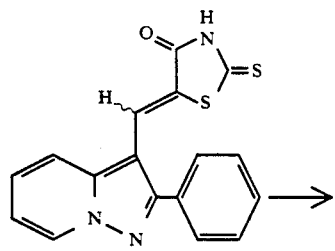

A mixture of 5-(2-phenylpyrazolo[1,5-a]pyridin-3-yl)methylenerhodanine (13.0 g) and 15% aqueous solution of sodium hydroxide (50 ml) was refluxed for 3 hours. To the reaction mixture was added 10% hydrochloric acid (50 ml) and water (50 ml) and was stirred for an hour under ice-cooling. The precipitates were collected by filtration to give 3-(2-phenylpyrazolo[1,5-a]pyridin-3-yl)-2-thioxopropionic acid (7.85 g).

mp: 199°-201° C.

IR (Nujol): 1690, 1625, 1590, 1570 cm$^{-1}$

NMR (DMF-d$_7$, δ): 7.02 (1H, t, J=7.5 Hz), 6.8-8.3 (10H, m), 8.68 (1H, d, J=7.5 Hz)

MS: 296 (M+), 250, 219, 194

PREPARATION 11

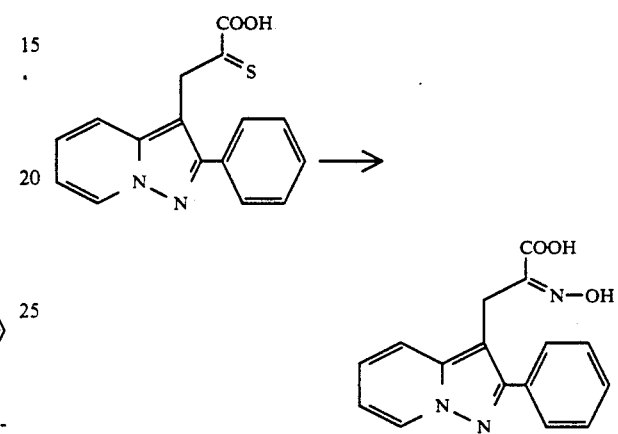

A mixture of 3-(2-phenylpyrazolo[1,5-a]pyridin-3-yl)-2-thioxopropionic acid (3.74 g), hydroxylamine hydrochloride (2.63 g), 85% potassium hydroxide (2.50 g) and 80% aqueous ethanol (22.4 ml) was refluxed for 3 hours. After cooling, to the reaction mixture was added water (40 ml) and the resulting precipitates were filtered off. The filtrate was washed with methylene chloride (20 ml) twice, acidified with 10% aqueous hydrochloric acid (pH≈2), and extracted with ethyl acetate (20 ml) twice. The organic layer was washed with water (10 ml) and a saturated aqueous solution of sodium chloride and dried over magnesium sulfate. The solvent was removed to give 3-(2-phenylpyrazolo[1,5-a]pyridin-3-yl)-2-hydroxyiminopropionic acid (2.60 g).

IR (Nujol): 3400-3000, 1680, 1635 cm$^{-1}$

NMR (DMF-d$_7$, δ): 4.00 and 4.20 (total 2H, each s), 6.70-8.03 (9H, m), 8.55 (1H, d, J=7.5 Hz)

PREPARATION 12

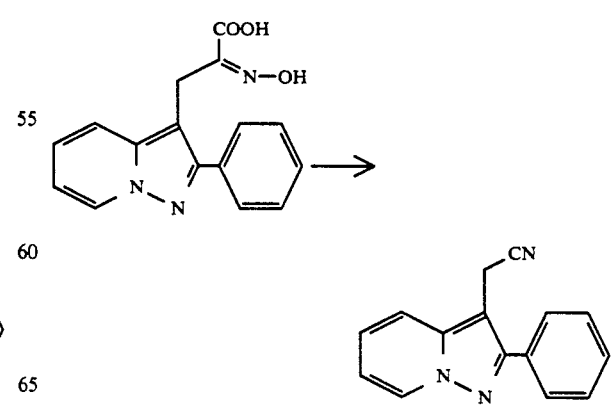

A solution of 3-(2-phenylpyrazolo[1,5-a]pyridin-3-yl)-2-hydroxyiminopropionic acid (0.20 g) in acetic anhydride (1 ml) was stirred for an hour at 80° C. After cooling to the mixture was added water (10 ml). The resulting precipitates were collected by filtration to give 2-(2-phenylpyrazolo[1,5-a]pyridin-3-yl)acetonitrile (0.10 g).

mp: 111°-114° C.

IR (Nujol): 2245, 1630, 1525 cm$^{-1}$

NMR (CDCl$_3$, δ): 3.93 (2H, s), 6.85 (1H, t, J=7.5 Hz), 7.24 (1H, t, J=7.5 Hz), 7.37-7.78 (6H, m), 8.50 (1H, d, J=7.5 Hz)

MS: 233, 207

PREPARATION 13

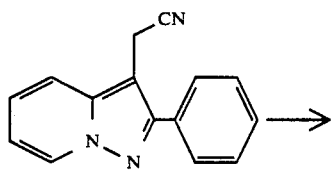

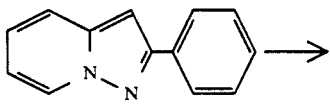

A mixture of 2-(2-phenylpyrazolo[1,5-a]pyridin-3-yl)acetonitrile (0.23 g), 85% sodium hydroxide (0.33 g) and 80% aqueous methanol was refluxed for 15 hours. The reaction mixture was acidified with 5% hydrochloric acid (pH≈1) and the precipitates were collected by filtration to give 2-(2-phenylpyrazolo[1,5-a]pyridin-3-yl)acetic acid (0.23 g).

mp: 197°-201° C.

IR (Nujol): 1700, 1630 cm$^{-1}$

NMR (DMSO-d$_6$, δ): 3.86 (2H, s), 6.88 (1H, t, J=7.5 Hz), 7.21 (1H, t, J=7.0 Hz), 7.35-7.83 (6H, m), 8.64 (1H, d, J=7.5 Hz), 11.8-12.8 (1H, broad s)

EXAMPLE 8

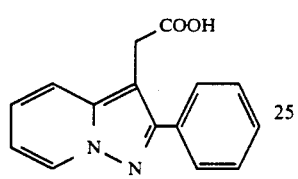

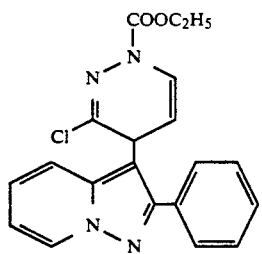

To a mixture of 3-chloropyridazine (0.66 g), 2-phenylpyrazolo[1,5-2]pyridine (1.12 g) and chloroform (6.6 ml) was added ethyl chloroformate (1.38 g) under ice-cooling and stirred for 2 hours at room temperature. To the reaction mixture was added methylene chloride (10 ml). The solution was washed with a saturated aqueous solution of sodium hydrogen carbonate (10 ml), and dried over magnesium sulfate. The organic layer was evaporated in vacuo and recrystallized from a mixture of ethyl acetate and 2-propanol to give 3-(3-chloro-1-ethoxycarbonyl-1,4-dihydropyridazin-4-yl)-2-phenylpyrazolo[1,5-a]pyridine (1.60 g).

mp: 129.5°-131.5° C.

IR (Nujol): 1715, 1675, 1630 cm$^{-1}$

NMR (CDCl$_3$, δ): 1.42 (3H, t, J=7.1 Hz), 4.42 (2H, q, J=7.1 Hz), 4.80 (1H, dd, J=1.6 Hz and 3.6 Hz), 5.00 (1H, dd, J=3.6 Hz and 8.2 Hz), 6.86 (1H, dt, J=1.4 Hz and 6.8 Hz), 7.15-7.69 (8H, m), 8.52 (1H, dd, J=1.0 Hz and 7.0 Hz)

Analysis Calcd. for C$_{20}$H$_{17}$ClN$_4$O$_2$ (%): C 63.08, H 4.50, N 14.71; Found: C 63.04, H 4.52, N 14.50

The following compounds (Examples 9 and 10) were obtained according to a similar manner to that of Example 8.

EXAMPLE 9

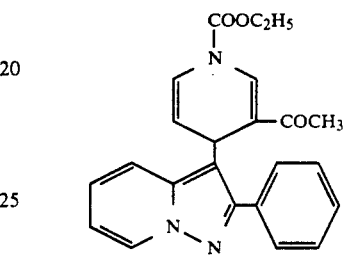

3-(3-Acetyl-1-ethoxycarbonyl-1,4-dihydropyridin-4-yl)-2-phenylpyrazolo[1,5-a]pyridine mp: 151°-153° C.

IR (Nujol): 1735, 1660, 1610 cm$^{-1}$

NMR (CDCl$_3$, δ): 1.32 (3H, t, J=7.5 Hz), 2.05 (3H, s), 4.32 (2H, q, J=7.5 Hz), 4.84 (1H, d, J=4.0 Hz), 5.15 (1H, dd, J=8.0 Hz and 4.0 Hz), 6.75 (1H, d, J=8.0 Hz), 6.80 (1H, t, J=7.5 Hz), 7.15 (1H, t, J=7.5 Hz), 7.16-7.75 (6H, m), 7.82 (1H, s), 8.58 (1H, d, J=7.5 Hz)

MS: 387 (M$^+$), 344, 314, 300, 269, 241

EXAMPLE 10

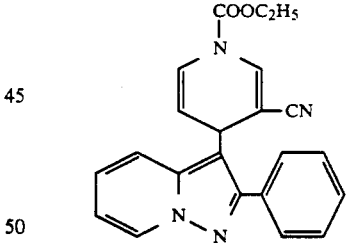

3-(3-Cyano-1-ethoxycarbonyl-1,4-dihydropyridin-4-yl)-2-phenylpyrazolo[1,5-a]pyridine mp: 182°-183° C.

IR (Nujol): 2215, 1740, 1680, 1620 cm$^{-1}$

NMR (CDCl$_3$, δ): 1.31 (3H, t, J=7.5 Hz), 4.29 (2H, q, J=7.5 Hz), 4.75 (1H, m), 5.14 (1H, dd, J=9.0 Hz and 3.0 Hz), 6.80 (1H, d, J=9.0 Hz), 6.93 (1H, t, J=7.5 Hz), 7.27 (1H, t, J=7.5 Hz), 7.36-7.70 (7H, m), 8.70 (1H, d, J=7.5 Hz)

MS: 370 (M$^+$), 342, 325, 297, 270

EXAMPLE 11

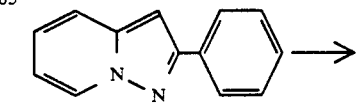

-continued

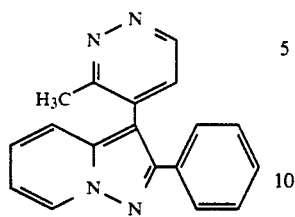

To a mixture of 2-phenylpyrazolo[1,5-a]pyridine (5.00 g), 3-methylpyridazine (2.90 g) and methylene chloride (20 ml), was added a solution of ethyl chloroformate (5.57 g) in methylene chloride for 17 minutes under ice-cooling and stirred for an hour at the same temperature and then for 6 hours and 40 minutes at room temperature. To the reaction mixture was added methylene chloride (20 ml), and washed with a solution of potassium carbonate (10 ml) and a saturated aqueous solution of sodium chloride (10 ml) and dried over magnesium sulfate. The solvent was removed and chromatographed on silica gel (70 g) with a mixture of n-hexane and ethyl acetate (2:1). The fractions containing the object compound were combined and evaporated in vacuo and recrystallized from a mixture of ethyl acetate and n-hexane to give 3-(3-methylpyridazin-4-yl)-2-phenylpyrazolo[1,5-a]pyridine (2.36 g).

mp: 209°–214° C.

IR (Nujol): 1630, 1610 cm$^{-1}$

NMR (CDCl$_3$, δ): 246 (3H, s), 6.98 (1H, t, J=7.5 Hz), 7.19–7.58 (7H, m), 7.91 (1H, d, J=6.0 Hz), 8.58 (1H, d, J=7.5 Hz), 9.32 (1H, d, J=6.0 Hz)

MS: 286 (M+), 257, 231, 218

The following compounds (Examples 12 and 13) were obtained according to a similar manner to that of Example 11.

EXAMPLE 12

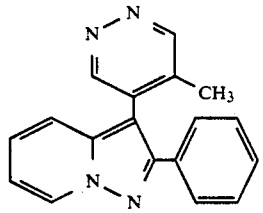

3-(5-Methylpyridazin-4-yl)-2-phenylpyrazolo[1,5-a]pyridine mp: 158°–159.5° C.

IR (Nujol): 3080, 1630 cm$^{-1}$

NMR (CDCl$_3$, δ): 1.90 (3H, s), 6.80 (1H, t, J=7.5 Hz), 7.12–7.50 (7H, m), 8.51 (1H, d, J=7.5 Hz), 8.99 (2H, s)

MS: 286 (M+), 257, 243, 218

Analysis Calcd. for C$_{18}$H$_{14}$N$_4$ (%): C 75.50, H 4.93, N 19.57; Found: C 75.22, H 5.09, N 19.26

EXAMPLE 13

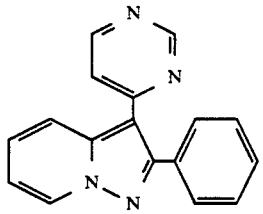

3-(Pyrimidin-4-yl)-2-phenylpyrazolo[1,5-a]pyridine mp: 130°–131° C.

IR (Nujol): 1625, 1580 cm$^{-1}$

NMR (CDCl$_3$, δ): 696–7.06 (2H, m), 7.35–7.64 (6H, m), 8.40 (1H, d, J=5.4 Hz), 8.22–8.61 (2H, m), 9.22 (1H, d, J=1.3 Hz)

MS: 271 (M+), 244, 217

Analysis Calcd. for C$_{17}$H$_{12}$N$_4$ (%): C 74.98, H 4.44, N 20.57; Found: C 74.87, H 4.62, N 20.33

EXAMPLE 14

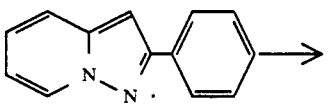

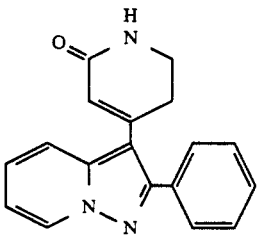

A mixture of 2-phenylpyrazolo[1,5-a]pyridine (0.50 g, 2,4-piperidinedione (0.292 g), concentrated sulfuric acid (1 drop) and acetic acid (0.5 ml) was heated at 135° C. for 13.5 hours. A saturated aqueous solution of sodium hydrogen carbonate (20 ml) was added to the reaction mixture and the mixture was extracted with chloroform (20 ml×2). The combined extract was washed with a saturated aqueous solution of sodium chloride (20 ml) and dried over magnesium sulfate. The solvent was evaporated in vacuo. The residue was purified by column chromatography on silica gel using a mixture of chloroform and ethyl acetate (9:1) and recrystallized from ethyl acetate to give crystals of 3-(2-oxo-1,2,5,6-tetrahydropyridin-4-yl)-2-phenylpyrazolo[1,5-a]pyridine.

mp: 188° to 189° C.

IR (Nujol): 1655, 1630, 1605 cm$^{-1}$

NMR (CDCl$_3$, δ): 2.44 (2H, t, J=6.5 Hz), 3.44 (2H, t, J=6.5 Hz), 6.20 (2H, s), 6.86 (1H, td, J=7.0 Hz and 1.0 Hz), 7.20–7.75 (7H, m), 8.50 (1H, dt, J=7.0 Hz and 1.0 Hz)

Analysis Calcd. for C$_{18}$H$_{15}$N$_3$O (%): C 74.72, H 5.23, N 14.53; Found: C 75.13, H 5.33, N 14.69

EXAMPLE 15

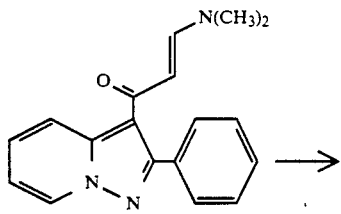

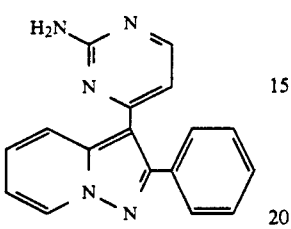

A solution of 3-(3-N,N-dimethylaminoacryloyl)-2-phenylpyrazolo[1,5-a]pyridine (0.63 g), guanidine hydrochloride (0.31 g), sodium ethoxide (0.54 g) and ethanol (9 ml) was refluxed for 2 hours. To the reaction mixture water (30 ml) was added and the mixture was extracted with ethyl acetate (60 ml). The organic layer was evaporated, then that residue was recrystallized from ethanol to give 3-(2-aminopyrimidin-4-yl)-2-phenylpyrazolo[1,5-a]pyridine (0.40 g).

mp: 222.5°-223° C.

IR (Nujol): 3370, 3320, 3180, 1640, 1560 cm$^{-1}$

NMR (CDCl$_3$, δ): 6.14 (1H, d, J=4.8 Hz), 6.52 (2H, s), 7.05 (1H, td, J=7 Hz and 1 Hz), 8.53 (1H, d, J=8 Hz), 8.76 (1H, d, J=7 Hz)

MS: 286

Analysis Calcd. for C$_{17}$H$_{13}$N$_5$ (%): C 71.07, H 4.56, N 24.37; Found: C 70.93, H 4.59, N 23.74

EXAMPLE 16

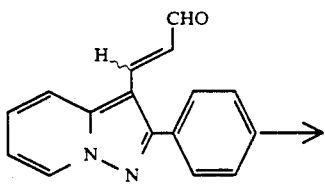

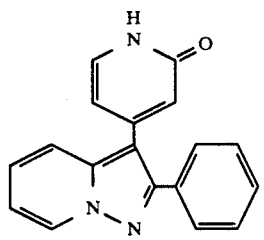

A mixture of 3-(2-phenylpyrazolo[1,5-a]pyridin-3-yl)acrylaldehyde (cis and trans mixture) (1.15 g) and 1-carbamoylmethylpyridinium chloride (0.80 g), 50% aqueous dimethylamine (0.44 g) and methanol (10 ml) was refluxed for 3 hours. The reaction mixture was evaporated in vacuo and the residue was heated for 10 minutes at 200° C. The resulting mixture was chromatographed on silica gel (80 g) with a mixture of chloroform and methanol (100:1). The fractions containing the object compound were combined and evaporated in vacuo and recrystallized from ethanol to give 3-(2-oxo-1,2-dihydropyridin-4-yl)-2-phenylpyrazolo[1,5-a]pyridine (0.33 g).

IR (Nujol): 1655, 1580 cm$^{-1}$

NMR (DMSO-d$_6$, δ): 5.72 (1H, dd, J=1.8 Hz and 6.8 Hz), 6.30 (1H, d, J=1.2 Hz), 7.04 (1H, dt, J=1.3 Hz and 6.8 Hz), 7.33-7.62 (7H, m), 7.73 (1H, d, J=9.0 Hz), 8.80 (1H, d, J=7.0 Hz), 11.52 (1H, broad s)

MS: 286 (M$^+$-1), 268

Analysis Calcd. for C$_{18}$H$_{13}$N$_3$O.$\frac{1}{3}$H$_2$O (%): C 73.60, H 4.69, N14.30; Found: C 73.70, H 4.82, N 14.28

EXAMPLE 17

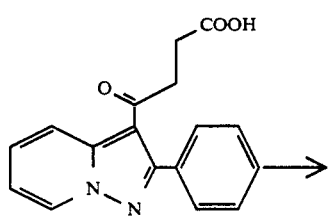

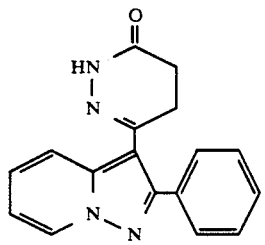

A mixture of 4-oxo-4-(2-phenylpyrazolo[1,5-a]pyridin-3-yl)butyric acid (1.71 g), hydrazine monohydrate (1.46 g) and ethanol (17 ml) was heated under reflux for 1 hour. Ethanol was evaporated in vacuo. Water (20 ml) was added to the residue, acidified with 5% hydrochloric acid and extracted with chloroform (25 ml×3). The combined extract was washed with a saturated aqueous solution of sodium chloride, dried over magnesium sulfate and evaporated in vacuo. The residue was recrystallized from ethanol to give crystals of 3-(3-oxo-2,3,4,5-tetrahydropyridazin-6-yl)-2-phenylpyrazolo[1,5-a]pyridine (1.19 g).

mp: 187° to 189° C.

IR (Nujol): 3325, 1675, 1630 cm$^{-1}$

NMR (DMSO-d$_6$, δ): 2.29-2.51 (4H, m), 7.05 (1H, td, J=7.0 Hz and 1.0 Hz), 7.37-7.68 (6H, m), 7.96 (1H, d, J=9.0 Hz), 8.78 (1H, d, J=7.0 Hz)

Analysis Calcd. for C$_{17}$H$_{14}$N$_4$O (%): C 70.33, H 4.86, N 19.30; Found: C 70.27, H 4.72, N 19.17

EXAMPLE 18

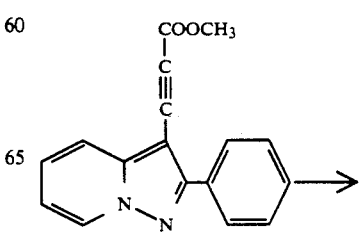

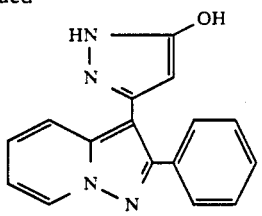

A mixture of methyl 3-(2-phenylpyrazolo[1,5-a]pyridin-3-yl)propiolate (1.50 g), hydrazine monohydrate (0.544 g) and ethanol (15 ml) was heated under reflux for 2 hours. Ethanol was evaporated in vacuo. Water (50 ml) was added to the residue and the mixture was acidified with 1N hydrochloric acid. The resultant precipitates were collected by filtration and washed with water. Recrystallization from a mixture of N,N-dimethylformamide and water gave crystals of 3-(5-hydroxypyrazol-3-yl)-2-phenylpyrazolo[1,5-a]pyridine (0.64 g).

mp: >300° C.

IR (Nujol): 2670, 2570, 1640, 1610 cm$^{-1}$

NMR (DMSO-d$_6$, δ): 5.43 (1H, s), 6.97 (1H, td, J=7.0 Hz and 1.0 Hz), 7.21–7.80 (7H, m), 8.73 (1H, d, J=7.0 Hz)

Analysis Calcd. for C$_{16}$H$_{12}$N$_4$O (%): C 69.55, H 4.38, N 20.28; Found: C 69.46, H 4.35, N 19.99

EXAMPLE 19

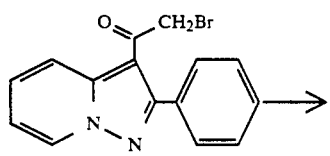

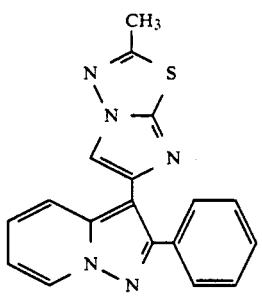

A mixture of 3-(2-bromoacetyl)-2-phenylpyrazolo[1,5-a]pyridine (1.87 g), 2-amino-5-methyl-1,3,4-thiadiazole (0.68 g) and 1-butanol (19 ml) was refluxed for 5 hours and 20 minutes. The reaction mixture was evaporated in vacuo and the residue was taken up methylene chloride (40 ml). The methylene chloride solution was washed with an aqueous solution of potassium carbonate and dried over magnesium sulfate. The solvent was removed and the residue was subjected to chromatography on silica gel (25 g) with chloroform as an eluent. The fractions containing the objective compound were combined and evaporated in vacuo to give 3-(2-methylimidazo[2,1-b][1,3,4]thiadiazol-6-yl)-2-phenylpyrazolo[1,5-a]pyridine (1.06 g), which was recrystallized from acetone gave crystals (0.69 g).

mp: 204° C.

IR (Nujol): 3130, 3100, 1635, 1590 cm$^{-1}$

NMR (CDCl$_3$, δ): 2.65 (3H, s), 6.75 (1H, t, J=7.5 Hz), 7.13 (1H, t, J=7.5 Hz), 7.25–7.50 (4H, m), 7.55–7.80 (2H, m), 8.14 (1H, d, J=9.0 Hz), 8.40 (1H, d, J=7.5 Hz)

MS: 302 (M+), 261, 221, 193

Analysis Calcd. for C$_{18}$H$_{13}$N$_3$S (%): C 62.24, H 3.95, N 21.13; Found: C 65.58, H 3.98, N 21.25

EXAMPLE 20

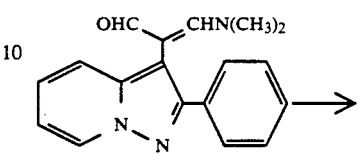

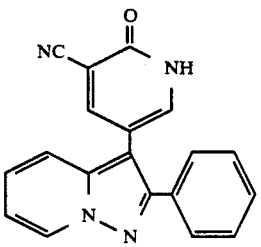

A mixture of 3-(N,N-dimethylamino)-2-(2-phenylpyrazolo[1,5-a]pyridin-3-yl)acrylaldehyde (cis and trans mixture) (4.00 g), 2-cyanoacetamide (2.31 g), sodium ethoxide (4.67 g) and ethanol (40 ml) was refluxed for 2 hours. After cooling the reaction mixture was added acetic anhydride (24 ml) and water (120 ml) and stirred at room temperature. The resultant precipitates were collected and recrystallized from a mixture of N,N-dimethylformamide and water to give 3-(3-cyano-2-oxo-1,2-dihydropyridin-5-yl)-2-phenylpyrazolo[1,5-a]pyridine (2.08 g).

mp: 312°–314° C.

IR (Nujol): 2240, 1670, 1540 cm$^{-1}$

NMR (DMSO-d$_6$, δ): 6.93 (1H, t, J=7.5 Hz), 7.27 (1H, t, J=7.5 Hz), 7.33–7.72 (8H, m), 8.03 (1H, d, J=7.5 Hz), 8.71 (1H, d, J=7.5 Hz)

MS: 312 (M+), 283

Analysis Calcd. for C$_{19}$H$_{12}$N$_4$O (%): C 73.07, H 3.87, N 17.94; Found: C 72.96, H 4.19, N 17.83

EXAMPLE 21

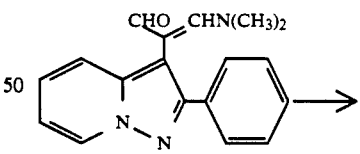

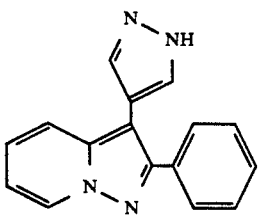

A mixture of 3-(N,N-dimethylamino)-2-(2-phenylpyrazolo[1,5-a]pyridin-3-yl)acrylaldehyde (0.70 g), hydrazine mono hydrate (0.18 g) and ethanol (7 ml) was refluxed for 4 hours. To the reaction mixture was added water (12 ml), and stirred under ice-cooling. The precipitates were collected and recrystallized from a mixture of ethanol and water to give 3-(4-pyrazolyl)-2-phenylpyrazolo[1,5-a]pyridine (0.51 g).

mp: 188°-190° C.

IR (Nujol): 3150, 1630 cm$^{-1}$

NMR (CDCl$_3$, δ): 6.75 (1H, t, J=7.5 Hz), 7.10 (1H, t, J=7.5 Hz), 7.25-7.80 (9H, m), 8.57 (1H, d, J=7.5 Hz)

MS: 260 (M$^+$), 232, 205

Analysis Calcd. for C$_{16}$H$_{12}$N$_4$(%): C 73.83, H 4.65, N 21.52; Found: C 73.49, H 5.01, N 21.18

The following compounds (Examples 22 to 25) were obtained according to a similar manner to that of Example 21.

EXAMPLE 22

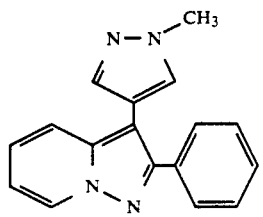

3-(1-Methylpyrazol-4-yl)-2-phenylpyrazolo[1,5-a]pyridine mp: 100°-103° C.

IR (Nujol): 1630 cm$^{-1}$

NMR (CDCl$_3$, δ): 3.90 (3H, s), 6.70 (1H, t, J=7.5 Hz), 7.07 (1H, t, J=7.5 Hz), 7.21-7.46 (5H, m), 7.48 (1H, s), 7.60-7.80 (2H, m), 8.43 (1H, d, J=7.5 Hz)

MS: 274 (M$^+$), 246

Analysis Calcd. for C$_{17}$H$_{14}$N$_4$(%): C 74.43, H 5.14, N 20.42; Found: C 74.64, H 5.46, N 20.36

EXAMPLE 23

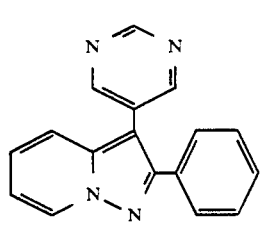

3-(5-Pyrimidinyl)-2-phenylpyrazolo[1,5-a]pyridine mp: 163°-165° C.

IR (Nujol): 1625 cm$^{-1}$

NMR (CDCl$_3$, δ): 6.83 (1H, t, J=7.5 Hz), 7.18 (1H, t, J=7.5 Hz), 7.25-7.60 (6H, m), 8.51 (1H, d, J=7.5 Hz), 8.70 (2H, s), 9.10 (1H, s)

MS: 272 (M$^+$), 244, 218

Analysis Calcd. for C$_{17}$H$_{12}$N$_4$(%): C 74.98, H 4.44, N 20.57; Found: C 75.14, H 5.04, N 20.42

EXAMPLE 24

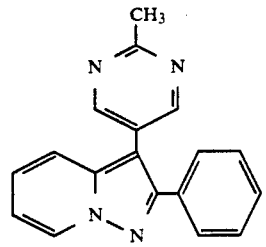

3-(2-Methylpyridimin-5-yl)-2-phenylpyrazolo[1,5-a]pyridine mp: 152°-153° C.

IR (Nujol): 3030-3100, 1635 cm$^{-1}$

NMR (CDCl$_3$, δ): 2.73 (3H, s), 6.80 (1H, t, J=7.5 Hz), 7.18 (1H, t, J=7.5 Hz), 7.20-7.65 (6H, m), 8.50 (1H, d, J=7.5 Hz), 8.60 (2H, s)

MS: 286 (M$^+$), 244, 218

Analysis Calcd. for C$_{18}$H$_{14}$N$_4$(%): C 75.51, H 4.93, N 19.57; Found: C 75.38, H 5.14, N 19.16

EXAMPLE 25

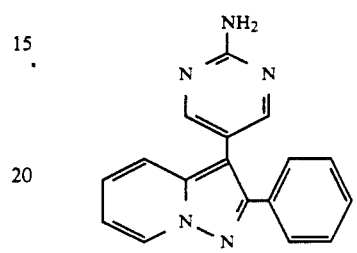

3-(2-Aminopyrimidin-5-yl)-2-phenylpyrazolo[1,5-a]pyridine mp: 304°-305° C.

IR (Nujol): 3400-3050, 1660, 1605 cm$^{-1}$

NMR (DMSO-d$_6$, δ): 6.43 (2H, s), 6.68 (1H, t, J=7.5 Hz), 7.02 (1H, t, J=7.5 Hz), 7.07-7.45 (6H, m), 7.93 (2H, s), 8.48 (1H, d, J=7.5 Hz)

MS: 287 (M$^+$), 246, 218

Analysis Calcd. for C$_{17}$H$_{13}$N$_5$(%): C 71.07, H 4.56, N 24.37; Found: C 71.23, H 4.88, N 24.04

EXAMPLE 26

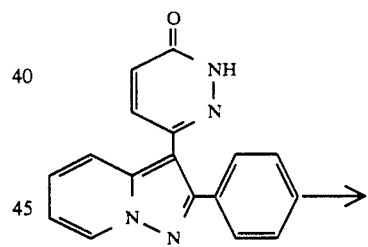

→

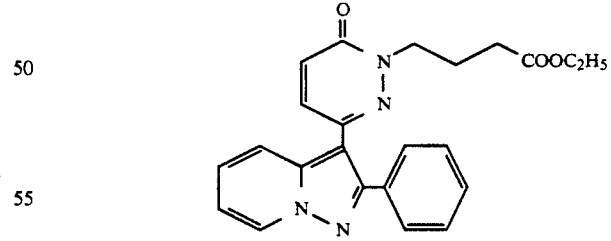

A mixture of 3-(3-oxo-2,3-dihydropyridazin-6-yl)-2-phenylpyrazolo[1,5-a]pyridine (0.47 g), ethyl 4-bromobutyrate (0.32 g), triton B (0.5 ml) and chloroform was stirred for 2 days under room temperature. The reaction mixture was evaporated and the residue was subjected to a column chromatography on silica gel (20 g) with chloroform as an eluent. The fractions containing the object compound were combined (20 ml) and concentrated under reduced pressure. The residue was dissolved in ethyl acetate and filtered off. The filtrate was evaporated to give 3-[2-(3-ethoxycarbonylpropyl)-3-oxo-2,3-dihydropyridazin-6-yl]-2-phenyl-pyrazolo[1,5-a]pyridine (0.49 g).

mp: 71°–75° C.

IR (Nujol): 1730, 1660, 1630, 1590, 1525 cm$^{-1}$

NMR (CDCl$_3$, δ): 1.25 (3H, t, J=6 Hz), 2.00–2.60 (4H, m), 4.00–4.45 (4H, Hex), 6.77 (1H, d, J=10 Hz), 6.92 (1H, td, J=7 Hz and 1 Hz), 7.03 (1H, d, J=10 Hz), 7.25–7.80 (6H, m), 8.00 (1H, d, J=9 Hz), 8.52 (1H, d, J=7 Hz)

MS: 402

Analysis Calcd. for C$_{23}$H$_{22}$N$_4$O$_3$ (%): C 68.64, H 5.51, N 13.92; Found: C 68.79, H 5.78, N 13.72

The following compounds (Examples 27 and 32) were obtained according to a similar manner to that of Example 26.

EXAMPLE 27

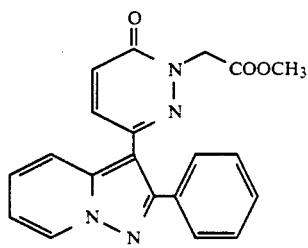

3-(2-Methoxycarbonylmethyl-3-oxo-2,3-dihydropyridazin-6-yl)-2-phenylpyrazolo[1,5-a]pyridine mp: 142.5°–143° C.

IR (Nujol): 1740, 1670, 1630, 1590 cm$^{-1}$

NMR (CDCl$_3$, δ): 3.82 (3H, s), 4.99 (2H, s), 6.75 (1H, d, J=10 Hz), 6.87 (1H, td, J=7 Hz and 1 Hz), 7.03 (1H, d, J=10 Hz), 7.18–7.75 (6H, m), 7.93 (1H, d, J=8 Hz), 8.50 (1H, d, J=7 Hz)

MS: 360 (M$^+$)

Analysis Calcd. for C$_{20}$H$_{16}$N$_4$O$_3$ (%): C 66.66, H 4.47, N 15.55; Found: C 66.69, H 4.47, N 15.75

EXAMPLE 28

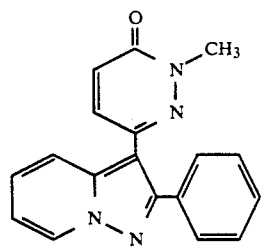

3-(2-Methyl-3-oxo-2,3-dihydropyridazin-6-yl)-2-phenylpyrazolo[1,5-a]pyridine mp: 145°–145.5° C.

IR (Nujol): 1675, 1585, cm$^{-1}$

NMR (CDCl$_3$, δ): 3.89 (3H, s), 6.72 (1H, d, J=9 Hz), 6.88 (1H, td, J=6 Hz and 1 Hz), 7.00 (1H, d, J=9 Hz), 7.15–7.70 (6H, m), 7.97 (1H, d, J=7 Hz), 8.50 (1H, d, J=8 Hz)

MS: 302

Analysis Calcd. for C$_{18}$H$_{14}$N$_4$O (%): C 71.51, H 4.67, N 18.53; Found: C 71.60, H 4.58, N 18.65

EXAMPLE 29

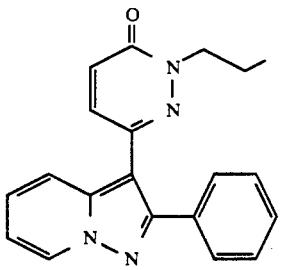

3-(2-Propyl-3-oxo-2,3-dihydropyridazin-6-yl)-2-phenylpyrazolo[1,5-a]pyridine mp: 110°–110.5° C.

IR (Nujol): 1660, 1590, 1530 cm$^{-1}$

NMR (CDCl$_3$, δ): 1.05 (3H, t, J=7 Hz), 1.95 (2H, Hex, J=7 Hz), 4.23 (2H, t, J=7 Hz), 6.72 (1H, d, J=10 Hz), 6.87 (1H, td, J=7 Hz and 1 Hz), 6.97 (1H, d, J=10 Hz), 7.17–7.70 (6H, m), 7.93 (1H, d, J=10 Hz), 8.50 (1H, d, J=7 Hz)

MS: 330

Analysis Calcd. for C$_{20}$H$_{18}$N$_4$O (%): C 72.71, H 5.49, N 16.96; Found: C 72.81, H 5.65, N 16.98

EXAMPLE 30

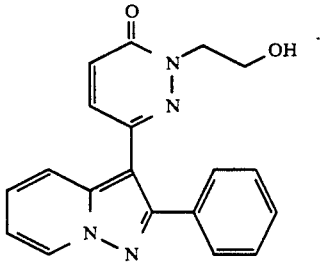

3-[2-(2-Hydroxyethyl)-3-oxo-2,3-dihydropyridazin-6-yl]-2-phenylpyrazolo[1,5-a]pyridine mp: 185.5°–187° C.

IR (Nujol): 3350, 1650, 1580, 1520, 1500 cm$^{-1}$

NMR (CDCl$_3$, δ): 4.05 (2H, m), 4.30 (2H, d, J=4 Hz), 6.70 (1H, d, J=10 Hz), 6.82 (1H, td, J=7 Hz and 1 Hz), 7.00 (1H, d, J=10 Hz), 7.15–7.60 (6H, m), 7.87 (1H, d, J=10 Hz), 8.45 (1H, d, J=7 Hz)

MS: 332 (M$^+$)

Analysis Calcd. for C$_{19}$H$_{16}$N$_4$O$_2$ (%): C 68.66, H 4.85, N 16.86; Found: C 67.29, H 5.05, N 16.42

EXAMPLE 31

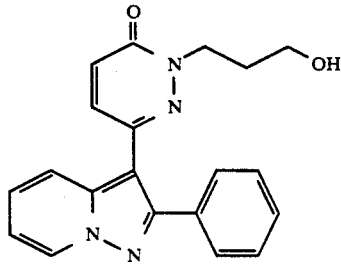

3-[2-(3-Hydroxypropyl)-3-oxo-2,3-dihydropyridazin-6-yl]-2-phenylpyrazolo[1,5-a]pyridine mp: 164.5°–165° C.

IR (Nujol): 1660, 1590, 1540 cm⁻¹

NMR (CDCl₃, δ): 2.11 (2H, q, J=6 Hz), 3.46-3.70 (3H, m), 4.46 (2H, t, J=6 Hz), 6.80 (1H, d, J=10 Hz), 6.14 (1H, td, J=7 Hz and 1 Hz), 7.01 (1H, d, J=10 Hz), 7.26-7.64 (6H, m), 7.99 (1H, d, J=8 Hz)

MS: 346 (M⁺)

Analysis Calcd. for C₂₀H₁₈N₄O₂ (%): C 69.35, H 5.24, N 16.17; Found: C 69.02, H 5.28, N 15.74

EXAMPLE 32

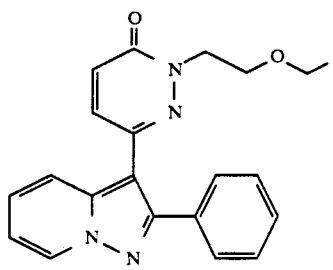

3-[2-(2-Ethoxyethyl)-3-oxo-2,3-dihydropyridazin-6-yl]-2-phenylpyrazolo[1,5-a]pyridine mp: 117°-118° C.

IR (Nujol): 1665, 1630, 1590, 1530 cm⁻¹

NMR (CDCl₃, δ): 1.23 (3H, t, J=7 Hz), 3.59 (2H, q, J=7 Hz), 3.92 (2H, t, J=6 Hz), 4.49 (2H, t, J=6 Hz), 6.75 (1H, d, J=10 Hz), 6.94 (1H, td, J=6 Hz and 1 Hz), 7.00 (1H, d, J=10 Hz), 7.24-7.76 (6H, m), 8.12 (1H, d, J=12 Hz), 8.52 (1H, d, J=8 Hz)

MS: 360 (M⁺)

Analysis Calcd. for C₂₁H₂₀N₄O₂ (%): C 69.98, H 5.59, N 15.55; Found: C 70.57, H 5.52, N 15.82

EXAMPLE 33

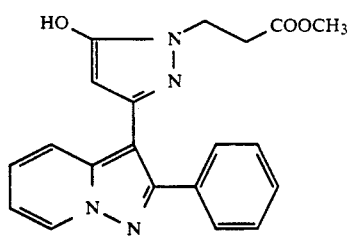

3-[1-(2-Methoxycarbonylethyl)-5-hydroxypyrazol-3-yl]-2-phenylpyrazolo[1,5-a]pyridine was obtained according to a similar manner to that of Example 5.

mp: 194°-196° C.

IR (Nujol): 2630, 1730, 1635, 1585 cm⁻¹

NMR (DMSO-d₆, δ): 2.49-2.53 (2H, m), 3.38 (3H, s), 5.63 (1H, s), 3.67 (2H, broad s), 7.03 (1H, td, J=7.0 Hz and 1.5 Hz), 7.31-7.62 (7H, m), 8.81 (1H, d, J=7.0 Hz), 9.84 (1H, s)

Analysis Calcd. for C₂₀H₁₈N₄O₃·½H₂O (%): C 64.69, H 5.12, N 15.04; Found: C 64.99, H 5.29, N 14.77

EXAMPLE 34

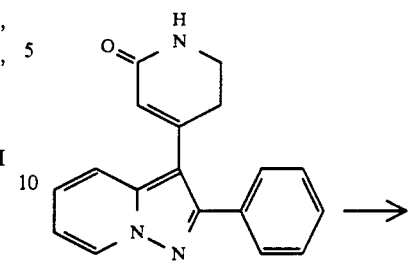

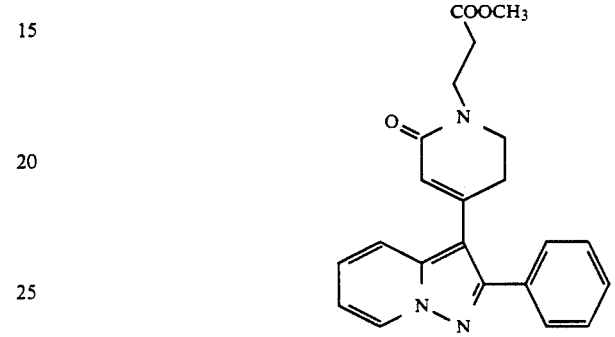

Sodium hydride (60%, 43.6 mg) was added to a mixture of 3-(2-oxo-1,2,5,6-tetrahydropyridin-4-yl)-2-phenylpyrazolo[1,5-a]pyridine (210 mg), methyl acrylate (93.8 mg) and tetrahydrofuran (2.1 ml) under ice-cooling. The reaction mixture was stirred at room temperature for 1.5 hours. A saturated solution of sodium chloride (20 ml) was added to the reaction mixture and extracted with ethyl acetate (20 ml×2). The combined extract was washed with a saturated solution of sodium chloride (20 ml), dried over magnesium sulfate and evaporated in vacuo. The residue was purified by column chromatography on silica gel using a mixture of chloroform and ethyl acetate (10:1) to give 3-[1-(2-methoxycarbonylethyl)-2-oxo-1,2,5,6-tetrahydropyridin-4-yl]-2-phenylpyrazolo[1,5-a]pyridine (210.7 mg) as an oil.

IR (film): 1730, 1640, 1600, 1515 cm⁻¹

NMR (CDCl₃, δ): 2.41 (2H, t, J=6.5 Hz), 2.69 (2H, t, J=6.5 Hz), 3.47 (2H, t, J=6.5 Hz), 3.69 (3H, s), 3.72 (2H, t, J=6.5 Hz), 6.20 (1H, s), 6.85 (1H, td, J=7.0 Hz and 1.0 Hz), 7.19-7.74 (7H, m), 8.48 (1H, d, J=7.0 Hz)

MS: 375 (M⁺)

EXAMPLE 35

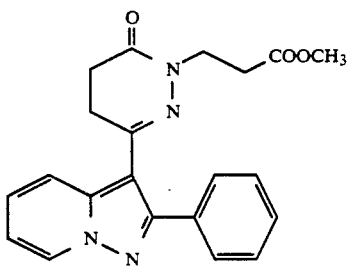

3-[2-(2-Methoxycarbonylethyl)-3-oxo-2,3,4,5-tetrahydropyridazin-6-yl]-2-phenylpyrazolo[1,5-a]pyridine was obtained according to a similar manner to that of Example 34.

IR (film): 1730, 1670 cm⁻¹

EXAMPLE 36

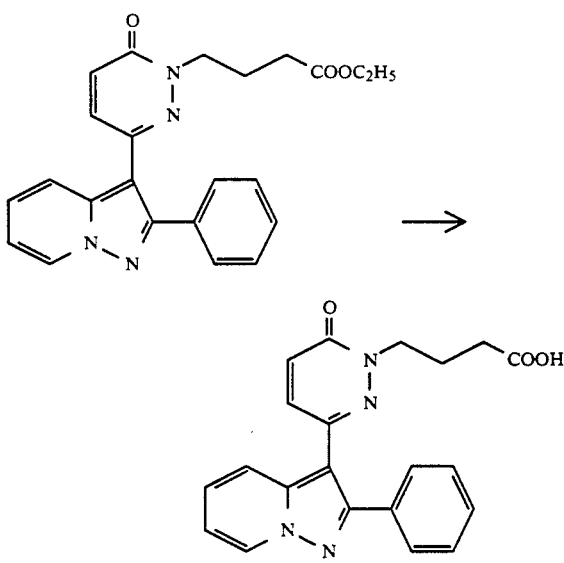

A mixture of 3-[2-(3-ethoxycarbonylpropyl)-3-oxo-2,3-dihydropyridazin-6-yl]-2-phenylpyrazolo[1,5-a]pyridine (13.7 g) and sodium hydroxide (2.73 g) in a mixture of water (8.6 ml) and methanol (96 ml) was refluxed for 2 hours and then the solvent was evaporated in vacuo. The residue was dissolved in water, and the aqueous solution was acidified with hydrochloric acid, and extracted with chloroform. The extract was dried over magnesium sulfate and the solvent was evaporated in vacuo. The residue was recrystallized from a mixture of ethanol and n-hexane to give 3-[2-(3-carboxypropyl)-3-oxo-2,3-dihydropyridazin-6-yl]-2-phenylpyrazolo[1,5-a]pyridine (9.48 g).

mp: 240°-240.5° C. (EtOH)
IR (Nujol): 1710, 1635, 1560, 1530, 1500 cm$^{-1}$
NMR (DMSO-d$_6$, δ): 1.97 (2H, q, J=7 Hz), 2.26 (2H, t, J=7 Hz), 3.23 (1H, broad), 4.13 (2H, t, J=7 Hz), 6.77 (1H, d, J=10 Hz), 7.00 (1H, td, J=7 Hz and 1 Hz), 7.03 (1H, d, J=10 Hz), 7.90 (1H, d, J=9 Hz), 7.75 (1H, d, J=7 Hz)
MS (M+): 374
Analysis Calcd. for C$_{21}$H$_{18}$N$_4$O$_3$ (%): C 67.37, H 4.85, N 14.96; Found: C 67.10, H 4.91, N 14.94

EXAMPLE 37

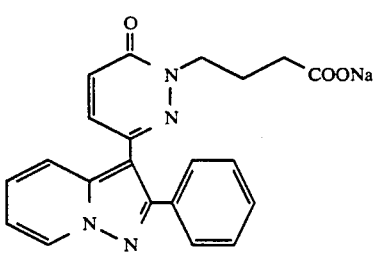

Sodium salt of 3-[2-(3-carboxypropyl)-3-oxo-2,3-dihydropyridazin-6-yl]-2-phenylpyrazolo[1,5-a]pyridine was prepared from the corresponding free compound (Example 36) according to a conventional manner.

mp: 114°-116° C.
IR (Nujol): 1660, 1585 cm$^{-1}$

NMR (DMSO-d$_6$, δ): 2.01 (4H, m), 4.15 (2H, t), 6.84 (1H, d, J=9 Hz), 7.00-7.09 (2H, m), 7.39-7.62 (6H, m), 7.97 (1H, d, J=8 Hz), 8.79 (1H, d, J=7 Hz)

EXAMPLE 38

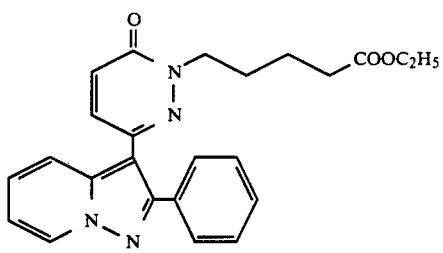

3-[2-(4-Ethoxycarbonylbutyl)-3-oxo-2,3-dihydropyridazin-6-yl]-2-phenylpyrazolo[1,5-a]pyridine was prepared according to a similar manner to that of Example 26.

IR (film): 1725, 1655, 1590 cm$^{-1}$
NMR (CDCl$_3$, δ): 1.25 (3H, t, J=7 Hz), 1.74-2.02 (4H, m), 2.41 (2H, t, J=7 Hz), 4.13 (2H, q, J=7 Hz), 4.32 (2H, t, J=7 Hz), 6.87 (1H, d, J=8 Hz), 7.02-7.07 (2H, m), 7.40-7.65 (6H, m), 8.05 (1H, d, J=9 Hz), 8.74 (1H, d, J=7 Hz)

EXAMPLE 39

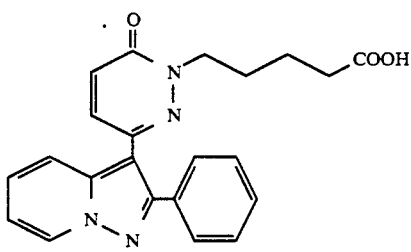

3-[2-(4-Carboxybutyl)-3-oxo-2,3-dihydropyridazin-6-yl]-2-phenylpyrazolo[1,5-a]pyridine was prepared according to a similar manner to that of Example 36.

mp: 182°-183° C.
IR (Nujol): 1710, 1640, 1570, 1530, 1500 cm$^{-1}$
NMR (CDCl$_3$, δ): 1.74-2.04 (4H, m), 2.47 (2H, t, J=6 Hz), 4.31 (2H, t, J=6 Hz), 6.79 (1H, d, J=10 Hz), 6.91 (1H, t, J=6 Hz), 7.01 (1H, d, J=10 Hz), 7.26-7.63 (6H, m), 7.97 (1H, d, J=9 Hz), 8.54 (1H, d, J=7 Hz)

EXAMPLE 40

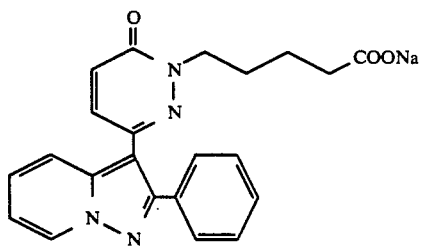

Sodium salt of 3-[2-(4-carboxybutyl)-3-oxo-2,3-dihydropyridazin-6-yl]-2-phenylpyrazolo[1,5-a]pyridine was prepared from the corresponding free compound (Example 39) according to a conventional manner.

mp: 244°-245° C.
IR (Nujol): 1660, 1650, 1570 cm$^{-1}$

NMR (DMSO-d₆, δ): 1.38–1.60 (2H, m), 1.62–1.83 (2H, m), 1.92 (2H, t, J=7 Hz), 4.11 (2H, t, J=7 Hz), 6.85 (1H, d, J=10 Hz), 7.04–7.09 (2H, m), 7.42–7.61 (6H, m), 7.95 (1H, d, J=8 Hz), 8.81 (1H, d, J=7 Hz)

EXAMPLE 41

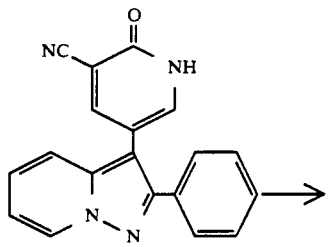

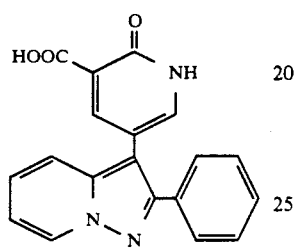

A mixture of 3-(3-cyano-2-oxo-1,2-dihydropyridin-5-yl)-2-phenylpyrazolo]1,5-a]pyridine (0.60 g) and 85% potassium hydroxide (0.38 g) in 67% aqueous ethanol (6 ml) was refluxed for 4 hours. After cooling, the reaction mixture was added onto ice (12 g) and acidified with 5% hydrochloric acid. Precipitates were collected and recrystallized from a mixture of N,N-dimethylformamide and water twice to give 3-(3-carboxy-2-oxo-1,2-dihydropyridin-5-yl)-2-phenylpyrazolo[1,5-a]pyridine (0.36 g).

mp: 335°–336° C. (dec.)
IR (Nujol): 1700, 1630, 1585, 1535 cm⁻¹
NMR (DMSO-d₆, δ): 6.98 (1H, t, J=7.0 Hz), 7.18–7.72 (7H, m), 7.97 (1H, d, J=3.0 Hz), 8.17 (1H, d, J=3.0 Hz), 8.77 (1H, d, J=7.0 Hz), 12.3–13.8 (2H, br)
MS: 331 (M+), 287
Analysis Calcd. for C₁₉H₁₃N₃O₃ (%): C 68.88, H 3.95, N 12.68; Found: C 68.58, H 3.99, N 12.63

EXAMPLE 42

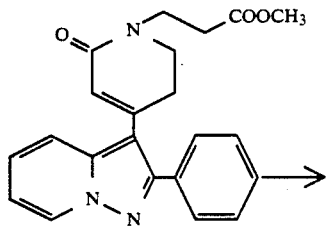

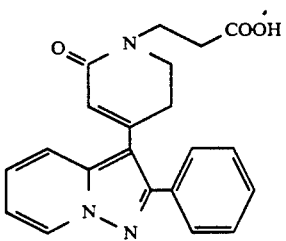

A mixture of 3-[1-(2-methoxycarbonylethyl)-2-oxo-1,2,5,6-tetrahydropyridin-4-yl]-2-phenylpyrazolo[1,5-a]pyridine (440 mg), 1N sodium hydroxide aqueous solution (3 ml) and methanol (4 ml) was heated under reflux for 1.5 hours. Methanol was evaporated in vacuo and water (20 ml) was added to the residue. The aqueous solution was acidified with 5% hydrochloric acid and precipitates were collected by filtration, washed with water, and then with petroleum ether (5 ml). The precipitates were recrystallized from 95% ethanol to give crystals of 3-[1-(2-carboxyethyl)-2-oxo-1,2,5,6-tetrahydropyridin-4-yl]-2-phenylpyrazolo[1,5-a]pyridine (220 mg).

mp: 182°–184° C.
IR (Nujol): 1735, 1640, 1585 cm⁻¹
NMR (CDCl₃, δ): 2.42 (2H, t, J=6.5 Hz), 2.74 (2H, t, J=6.5 Hz), 3.49 (2H, t, J=6.5 Hz), 3.73 (2H, t, J=6.5 Hz), 6.22 (1H, s), 7.20–7.74 (8H, m), 8.49 (1H, d, J=7.0 Hz)

EXAMPLE 43

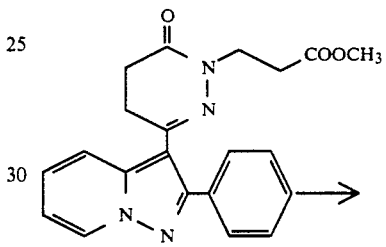

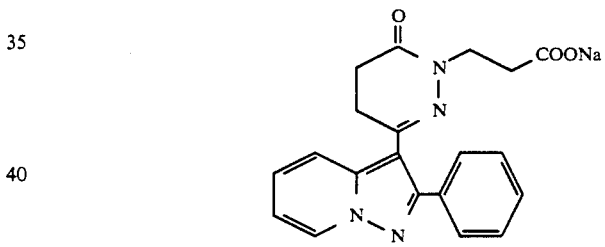

A mixture of 3-[2-(2-methoxycarbonylethyl)-3-oxo-2,3,4,5-tetrahydropyridazin-6-yl]-2-phenylpyrazolo[1,5-a]pyridine (484 mg), 1N sodium hydroxide aqueous solution (2.1 ml) and methanol (5 ml) was stirred at room temperature for 1 hour. Methanol was evaporated in vacuo. To the residue, water (10 ml) was added and the solution was acidified with 5% hydrochloric acid and extracted with chloroform (20 ml×2). The combined extracts was washed with a saturated aqueous solution of sodium chloride (20 ml), dried over magnesium sulfate and evaporated in vacuo. The residue was purified by column chromatography on silica gel using a mixture of chloroform and methanol (30:1) as an eluent to give 3-[2-(2-carboxyethyl)-3-oxo-2,3,4,5-tetrahydropyridazin-6-yl]-2-phenylpyrazolo[1,5-a]pyridine (198 mg) as an oil. This free acid was dissolved in a mixture of 1N sodium hydroxide aqueous solution (0.547 mg) and ethanol (3 ml), and the solvent was evaporated in vacuo. The residue was triturated with 95% ethanol, collected by filtration, washed with acetone and dried to give powder of sodium salt of 3-[2-(2-carboxyethyl)-3-oxo-2,3,4,5-tetrahydropyridazin-6-yl]-2-phenylpyrazolo[1,5-a]pyridine (129 mg).

IR (Nujol): 1640, 1560, 1510 cm⁻¹

NMR (D₂O, δ): 2.04 (4H, s), 2.25 (2H, t, J=7.5 Hz), 3.71 (2H, t, J=7.5 Hz), 6.71 (1H, t, J=7.0 Hz), 7.08-7.23 (6H, m), 7.63 (1H, d, J=9.0 Hz), 8.06 (1H, d, J=7.0 Hz)

Analysis Calcd. for $C_{20}H_{17}NaN_4O_3 \cdot 3H_2O$ (%): C 54.79, H 5.25, N 12.99; Found: C 55.46, H 4.71, N 12.71

EXAMPLE 44

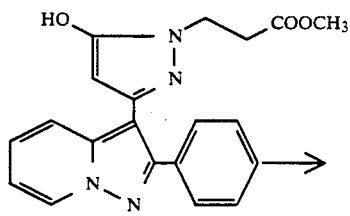

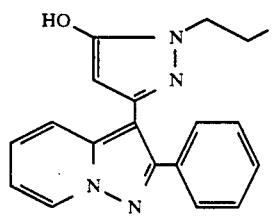

A mixture of 3-[1-(2-methoxycarbonylethyl)-5-hydroxypyrazol-3-yl]-2-phenylpyrazolo[1,5-a]pyridine (0.50 g), 1N sodium hydroxide aqueous solution (3 ml) and ethanol (5 ml) was heated under reflux for 2.5 hours. Ethanol was evaporated in vacuo. The residue was acidified with 5% hydrochloric acid and extracted with chloroform (25 ml×2). Combined extract was washed with a saturated aqueous solution of sodium chloride (25 ml), dried over magnesium sulfate and evaporated in vacuo. The residue was purified by column chromatography on silica gel using a mixture of chloroform and methanol (30:1) as an eluent and recrystallized from ethanol to give crystal of 3-[1-(2-carboxyethyl)-5-hydroxypyrazol-3-yl]-2-phenylpyrazolo[1,5-a]pyridine (141 mg).

mp: 211° to 213° C.

IR (Nujol): 1705, 1610 cm⁻¹

NMR (CDCl₃, δ): 2.11 (2H, broad s), 3.89 (2H, broad s), 5.83 (1H, s), 6.91 (1H, t, J=6.0 Hz), 7.23-7.71 (7H, m), 8.54 (1H, d, J=6.0 Hz)

Analysis Calcd. for $C_{19}H_{16}N_4O_3$ (%): C 65.51, H 4.63, N 16.08; Found: C 65.10, H 4.60, N 16.16

EXAMPLE 45

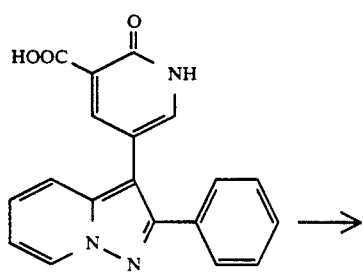

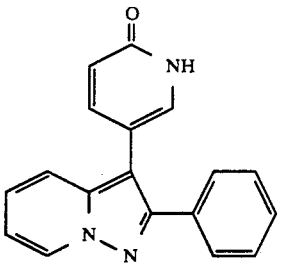

3-(3-Carboxy-2-oxo-1,2-dihydropyridin-5-yl)-2-phenylpyrazolo[1,5-a]pyridine (120 mg) was melted by an electric hot plate at 370° C. This was dissolved in a mixture of chloroform (26 ml) and methanol (13 ml), and silica gel (1 g) and charcoal (0.2 g) were added thereto and then this mixture was filtered. The solvent of the filtrate was removed and chromatographed on silica gel (3 g) with a mixture of chloroform, methanol and triethylamine (200:10:1). The fractions containing the object compound were combined and evaporated in vacuo and recrystallized from ethyl acetate to give 3-(2-oxo-1,2-dihydropyridin-5-yl)-2-phenylpyrazolo[1,5-a]pyridine (30 mg).

mp: 222°-224° C.

IR (Nujol): 1665, 1630 cm⁻¹

NMR (DMSO-d₆, δ): 6.39 (1H, d, J=9.2 Hz), 6.96 (1H, t, J=6.0 Hz), 7.23-7.65 (9H, m), 8.73 (1H, d, J=7.0 Hz), 11.75 (1H, broad s)

MS: 287 (M⁺), 258, 231

Analysis Calcd. for $C_{18}H_{13}N_3O \cdot \frac{1}{3}H_2O$ (%): C 73.70, H 4.70, N 14.34; Found: C 73.88, H 4.53, N 14.16

EXAMPLE 46

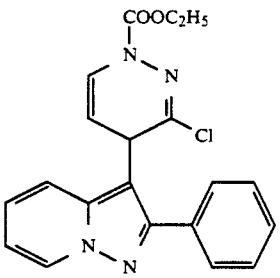

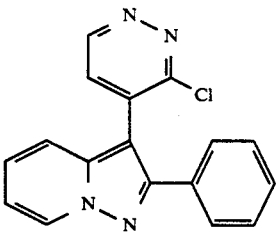

A mixture of 3-(3-chloro-1-ethoxycarbonyl-1,4-dihydropyridazin-4-yl)-2-phenylpyrazolo[1,5-a]pyridine (1.26 g), manganese (IV) oxide (12.6 g) and chloroform (12.6 ml) was refluxed for 10 hours. After filtration, organic layer was dried over magnesium sulfate. The solvent was removed and chromatographed on silica gel (12.6 g) with a mixture of hexane and ethyl acetate as an eluent. The fractions containing the objective compound were combined and evaporated in vacuo and recrystallized from a mixture of ethyl acetate and n-hexane to give 3-(3-chloropyridazin-4-yl)-2-phenyl-pyrazolo[1,5-a]pyridine (0.78 g).

mp: 208°–210° C.

IR (Nujol): 1635, 1570 cm$^{-1}$

NMR (CDCl$_3$, δ): 6.94 (1H, dt, J=1.6 Hz and 6.7 Hz), 7.25–7.49 (8H, m), 8.58 (1H, ddd, J=0.96 Hz, 0.96 Hz, and 7.0 Hz), 9.06 (1H, d, J=4.9 Hz)

MS: 306 (M+), 271, 242, 216

Analysis Calcd. for C$_{17}$H$_{11}$ClN$_4$ (%): C 66.56, H 3.61, N 18.26; Found: C 66.96, H 3.63, N 18.31

EXAMPLE 47

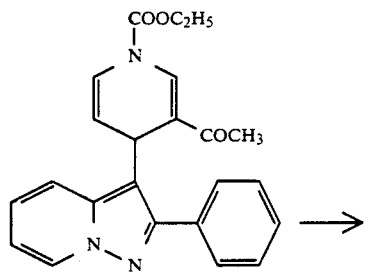

→

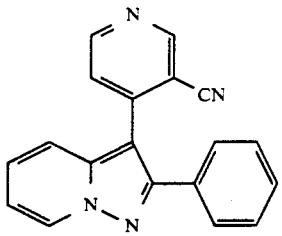

A mixture of 3-1-ethoxycarbonyl-3-acetyl-1,4-dihydropyridin-4-yl)-2-phenylpyrazolo[1,5-a]pyridine (2.20 g), potassium tert-butoxide (3.19 g) and tert-butanol (22 ml) was refluxed for an hour and 30 minutes. The solvent was removed and the residue was extracted with methylene chloride. Combined extract was washed with water and a saturated aqueous solution of sodium chloride, and dried over magnesium sulfate. The solvent was evaporated in vacuo. The residue was chromatographed on silica gel (12 g) with a mixture of n-hexane and ethyl acetate (4:1) as an eluent. The fractions containing the object compound was combined and the solvent was evaporated in vacuo. Recrystallization from a mixture of ethyl acetate and n-hexane gave 3-(3-acetylpyridin-4-yl)-2-phenylpyrazolo[1,5-a]pyridine (0.52 g).

mp: 159°–161° C.

IR (Nujol): 1690, 1630 cm$^{-1}$

NMR (CDCl$_3$, δ): 1.94 (3H, s), 6.83 (1H, t, J=7.5 Hz), 7.17 (1H, t, J=7.5 Hz), 7.20–7.53 (7H, m), 8.50 (1H, d, J=7.5 Hz), 8.65 (1H, d, J=5.0 Hz), 8.80 (1H, s)

MS: 313 (M+), 298, 242, 210

Analysis Calcd. for C$_{20}$H$_{15}$N$_3$O (%): C 76.66, H 4.82, N 13.41; Found: C 76.34, H 5.48, N 13.17

EXAMPLE 48

3-(3-Cyanopyridin-4-yl)-2-phenylpyrazolo[1,5-a]pyridine was obtained according to a similar manner to that of Example 47.

mp: 208°–210° C.

IR (Nujol): 2220, 1630, 1585 cm$^{-1}$

NMR (CDCl$_3$, δ): 6.80 (1H, t, J=7.5 Hz), 7.07–7.43 (8H, m), 8.43 (1H, d, J=7.5 Hz), 8.53 (1H, d, J=5.0 Hz), 8.77 (1H, s)

MS: 296 (M+), 270

Analysis Calcd. for C$_{19}$H$_{12}$N$_4$ (%): C 77.01, H 4.08, N 18.91; Found: C 77.30, H 4.17, N 19.02

EXAMPLE 49

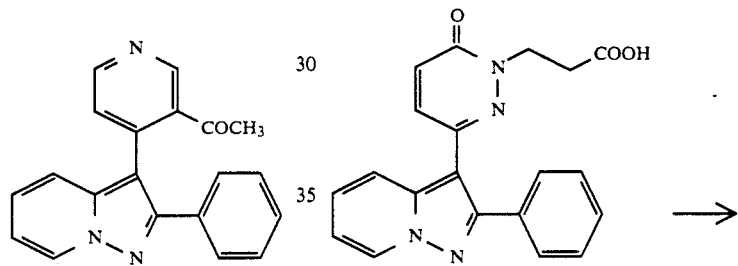

A mixture of 3-[2-(2-carboxyethyl)-3-oxo-2,3-dihydropyridazin-6-yl]-2-phenylpyrazolo[1,5-a]pyridine (0.36 g), methylene chloride (4 ml) and thionyl chloride (0.08 ml) was stirred for 30 minutes under room temperature, then thionyl chloride (0.08 ml) was added again and stirred for 60 minutes under room temperature. The reaction mixture was evaporated. The residue was dissolved in acetone (3 ml). This was added slowly to aqueous ammonia solution (6 ml) stirring at room temperature. After 20 minutes, the reaction mixture was evaporated, and thereto water (3 ml) was added. Precipitates were collected by filtration and recrystallized from ethanol to give 3-[2-(2-carbamoylethyl)-3-oxo-2,3-dihydropyridazin-6-yl]-2-phenylpyrazolo[1,5-a]pyridine (0.24 g).

mp: 215°–215.5° C.

IR (Nujol): 3450, 3330, 3210, 1660, 1595, 1535 cm$^{-1}$

NMR (CDCl$_3$, δ): 2.89 (2H, t, J=7 Hz), 4.58 (2H, t, J=7 Hz), 5.20–5.60 (1H, s), 6.00–6.50 (1H, s), 6.70 (1H, d, J=10 Hz), 7.89 (1H, t, J=7 Hz), 7.00 (1H, d, J=10 Hz), 7.20-7.68 (6H, m), 8.03 (1H, d, J=9 Hz), 8.50 (1H, d, J=7 Hz)

MS (M+): 359

Analysis Calcd. for C20H17N5O2 (%): C 66.84, H 4.77, N 19.49; Found: C 67.11, H 5.01, N 19.65

The following compounds (Examples 50 and 51) were obtained according to a similar manner to that of Example 49.

EXAMPLE 50

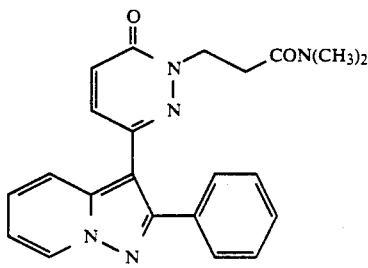

3-[2-(2-N,N-Dimethylcarbamoylethyl)-3-oxo-2,3-dihydropyridazin-6-yl]-2-phenylpyrazolo[1,5-a]pyridine mp: 144°-145° C.

IR (Nujol): 1665, 1640, 1590, 1530 cm$^{-1}$

NMR (CDCl3, δ): 2.97 (2H, t, J=8 Hz), 2.98 (3H, s), 3.03 (3H, s), 4.61 (2H, t, J=8 Hz), 6.75 (1H, d, J=10 Hz), 6.93 (1H, td, J=6 Hz and 1 Hz), 7.02 (1H, d, J=10 Hz), 7.26-8.64 (6H, m), 8.08 (1H, d, J=8 Hz), 8.52 (1H, d, J=7 Hz)

MS (M+): 387

Analysis Calcd. for C22H21N5O2: C 68.20, H 5.46, N 18.08; Found: C 68.60, H 5.67, N 18.04

EXAMPLE 51

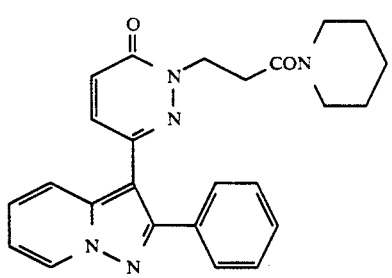

1-[3-{6-(2-Phenylpyrazolo[1,5-a]pyridin-3-yl)-3-oxo-2,3-dihydropyridazin-2-yl}propionyl]piperidine mp: 65°-70° C.

IR (Nujol): 1660, 1630, 1585, 1520 cm$^{-1}$

NMR (CDCl3, δ): 1.58-1.76 (6H, m), 2.96 (2H, t, J=8 Hz), 3.49 (4H, d, J=32 Hz), 4.61 (2H, t, J=8 Hz), 6.75 (1H, d, J=10 Hz), 6.94 (1H, td, J=7 Hz and 1 Hz), 7.02 (1H, d, J=10 Hz), 7.26-7.63 (6H, m), 7.68 (1H, d, J=8 Hz), 8.53 (1H, d, J=7 Hz)

MS: 427 (M+)

Analysis Calcd. for C25H25N5O2 (%): C 70.28, H 5.89, N 16.38; Found: C 69.15, H 6.01, N 16.18

EXAMPLE 52

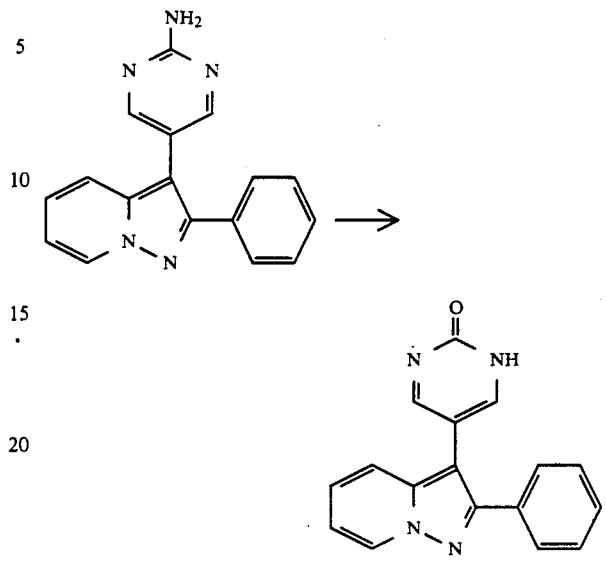

To a mixture of 3-(2-aminopyrimidin-5-yl)-2-phenyl-pyrazolo[1,5-a]pyridine (0.70 g) and 50% sulfuric acid (5.6 ml) was gradually added aqueous solution (5.6 ml) of sodium nitrite (1.68 g) at 5° to 10° C., and the resultant mixture was stirred for 3 hours at the same temperature and then for 2 hours at room temperature. To the reaction mixture was added water (14 ml). The precipitates were collected by filtration subjected to a column chromatography on silica gel (14 g) with a mixture of chloroform and methanol (10:1) as an eluent. The fractions containing the objective compound were combined and the solvent was evaporated in vacuo to give 3-(2-oxo-1,2-dihydropyrimidin-5-yl)-2-phenyl-pyrazolo[1,5-a]pyridine (0.44 g).

mp: 324°-326° C. (dec.)

IR (Nujol): 3200-2300, 1720, 1700, 1645, 1625 cm$^{-1}$

NMR (DMSO-d6, δ): 6.93 (1H, t, J=7.5 Hz), 7.27 (1H, t, J=7.5 Hz), 7.33-7.70 (6H, m), 8.15 (2H, s), 8.75 (1H, d, J=7.5 Hz)

MS: 288 (M+), 260, 246, 218

EXAMPLE 53

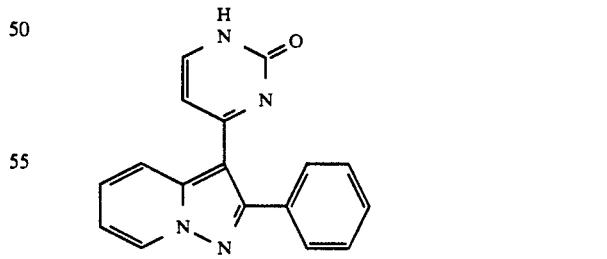

3-[2-Oxo-1,2-dihydropyrimidin-4-yl)-2-phenyl-pyrazolo[1,5-a]pyridine was obtained according to a similar manner to that of Example 52.

mp: 287°-289° C.

IR (Nujol): 1640, 1610 cm$^{-1}$

NMR (DMSO-d6, δ): 5.91 (1H, d, J=6.6 Hz), 7.18 (1H, t, J=6.4 Hz), 7.51-7.69 (7H, m), 8.55 (1H, d, J=8.9 Hz), 8.86 (1H, d, J=6.8 Hz), 11.1-11.9 (1H, broad s)

MS: 287 (M+-1), 259, 244

EXAMPLE 54

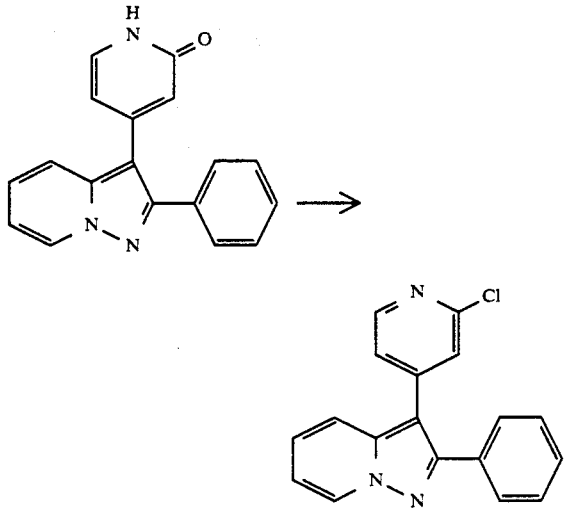

A mixture of 3-(2-oxo-1,2-dihydropyridin-4-yl)-2-phenylpyrazolo[1,5-a]pyridine (0.6 g) and phosphorus oxychloride (1.8 ml) was stirred for 6 hours at 70° C. After cooling, the reaction mixture was poured onto ice (30 g) and made alkaline with 24% aqueous solution of sodium hydroxide (pH=10) and extracted with chloroform (18 ml). The combined extract was washed with water and sodium chloride aqueous solution and dried over magnesium sulfate. The solvent was removed in vacuo and the residue was chromatographed on silica gel (12 g) with chloroform as an eluent. The fractions containing the object compound were combined and evaporated in vacuo and recrystallized from a mixture of ethyl acetate and diisopropyl ether to give 3-(2-chloropyridin-4-yl)-2-phenylpyrazolo[1,5-a]pyridine (0.21 g).

mp: 167°–168° C.
IR (Nujol): 1630, 1590, 1530 cm$^{-1}$
NMR (CDCl$_3$, δ): 6.91 (3H, t, J=6.8 Hz), 7.15 (1H, dd, J=1.5 Hz and 5.2 Hz), 7.25–7.69 (6H, m), 8.32 (1H, dd, J=0.5 Hz and 5.2 Hz), 8.54 (1H, dd, J=1.0 Hz and 6.0 Hz)
MS: 305 (M+), 270, 243
Analysis Calcd. for C$_{18}$H$_{12}$ClN$_3$(%): C 70.71, H 3.96, N 13.74; Found: C 70.51, H 3.95, N 13.62

EXAMPLE 55

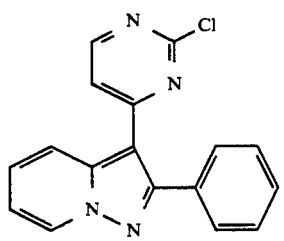

3-(2-Chloropyrimidin-4-yl)-2-phenylpyrazolo[1,5-a]pyridine was obtained according to a similar manner to that of Example 54.

mp: 181°–182° C.
IR (Nujol): 1630, 1570, 1530 cm$^{-1}$

NMR (CDCl$_3$, δ): 6.92 (1H, d, J=5.5 Hz), 7.02 (1H, dt, J=1.3 Hz and 6.9 Hz), 7.43–7.62 (6H, m), 8.23 (1H, d, J=5.4 Hz), 8.55 (1H, d, J=6.9 Hz), 8.64 (1H, d, J=9.0 Hz)
MS: 306 (M+), 271, 244, 217
Analysis Calcd. for C$_{17}$H$_{11}$ClN$_4$(%): C 66.56, H 3.61, N 18.26; Found: C 66.30, H 3.52, N 18.59

EXAMPLE 56

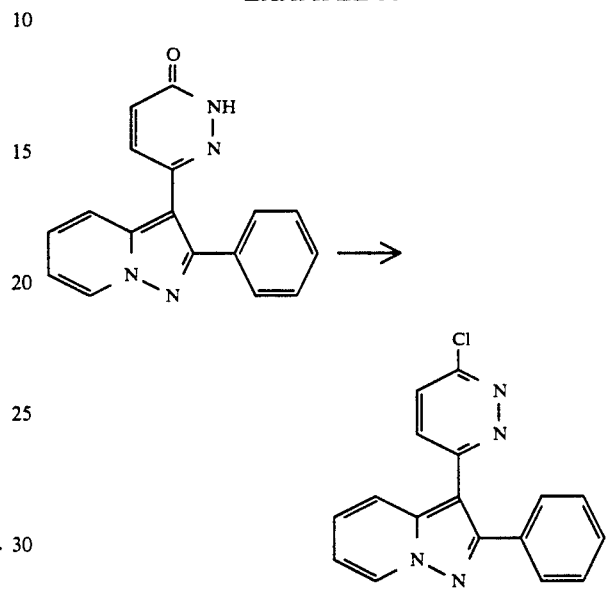

A mixture of 3-(3-oxo-2,3-dihydropyridazin-6-yl)-2-phenylpyrazolo[1,5-a]pyridine (2.91 g) and phosphorus oxychloride (10 ml) was heated under reflux for 1 hour. Phosphorus oxychloride was evaporated in vacuo. The residue was neutralized by saturated aqueous solution of sodium hydrogen carbonate and extracted with chloroform (30 ml×3). The combined extract was washed with a saturated aqueous solution of sodium chloride (20 ml) and dried over magnesium sulfate. The solvent was evaporated in vacuo and the residue was triturated with ethanol, collected by filtration, washed with ethanol and dried to give crystals of 3-(3-chloropyridazin-6-yl)-2-phenylpyrazolo[1,5-a]pyridine (2.42 g).

mp: 208°–211° C.
IR (Nujol): 1630, 1575, 1530 cm$^{-1}$
NMR (DMSO-d$_6$, δ): 7.14 (1H, td, J=7.0 Hz and 1.0 Hz), 7.36 (1H, d, J=9.0 Hz), 7.47–7.60 (6H, m), 7.78 (1H, d, J=9.0 Hz), 8.16 (1H, d, J=9.0 Hz), 8.87 (1H, d, J=7.0 Hz)
Analysis Calcd. for C$_{17}$H$_{11}$ClN$_4$(%): C 63.65, H 3.53, N 17.22; Found: C 63.14, H 3.48, N 17.29

EXAMPLE 57

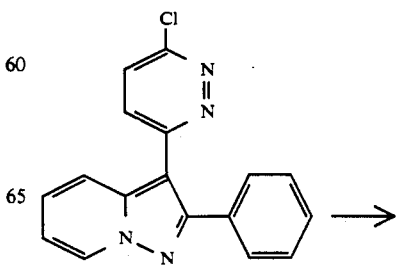

-continued

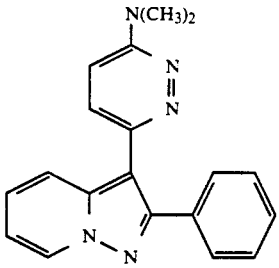

A mixture of 3-(3-cloropyridazin-6-yl)-2-phenyl-pyrazolo[1,5-a]pyridine (1.00 g) and a solution of dimethylamine in methanol (30 ml) was heated under reflux for 8.5 hours. Methanol was evaporated in vacuo and the residue was dissolved in chloroform (50 ml). The chloroform solution was extracted with 10% hydrochloric acid (50 ml×2). The aqueous layer was neutralized with potassium carbonate and extracted with chloroform (30 ml×2). The combined extract was washed with a saturated aqueous solution of sodium chloride (30 ml), dried over magnesium sulfate and evaporated in vacuo. The residue was recrystallized from ethanol to give crystal of 3-(3-N,N-dimethylaminopyridazin-6-yl)-2-phenylpyrazolo[1,5-a]pyridine (421 mg).

mp: 190°–194° C.

IR (Nujol): 1630, 1605, 1550, 1530 cm$^{-1}$

NMR (DMSO-d$_6$, δ): 3.13 (6H, s), 6.99–7.07 (3H, m), 7.31–7.59 (6H, m), 7.96 (1H, d, J=9.0 Hz), 8.79 (1H, d, J=6.0 Hz)

Analysis Calcd. for C$_{19}$H$_{17}$N$_5$ (%): C 72.36, H 5.43, N 22.21; Found: C 72.50, H 5.33, N 22.16

EXAMPLE 58

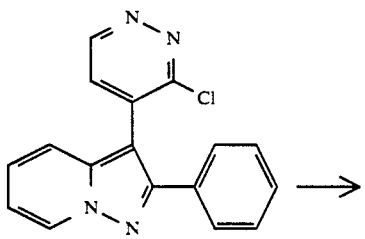

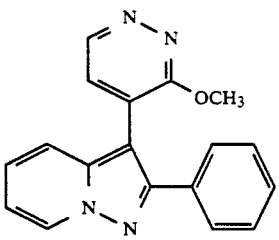

To a 28% methanolic solution of sodium methoxide (3 ml) was added 3-(3-chloropyridazin-4-yl)-2-phenyl-pyrazolo[1,5-a]pyridine (0.61 g). The mixture was refluxed for an hour and evaporated in vacuo. The residue was dissolved in chloroform (20 ml). The chloroform solution was washed with water (5 ml) and a saturated aqueous solution of sodium chloride (5 ml) and dried over magnesium sulfate. The solvent was removed and chromatographed on silica gel (10 g) with n-hexane-ethyl acetate as an eluent. The fractions containing the object compound were combined, evaporated in vacuo, and then recrystallized from a mixture of ethyl acetate and n-hexane to give 3-(3-methoxypyridin-4-yl)-2-phenylpyrazolo[1,5-a]pyridine (0.30 g).

mp: 180°–182° C.

IR (Nujol): 1630, 1580, 1510 cm$^{-1}$

NMR (CDCl$_3$, δ): 3.97 (3H, s), 6.89 (1H, dt, J=1.4 Hz and 6.4 Hz), 7.20–7.52 (8H, m), 8.55 (1H, d, J=6.9 Hz), 8.79 (1H, d, J=4.8 Hz)

MS: 302 (M+), 279

Analysis Calcd. for C$_{18}$H$_{14}$N$_4$O (%): C 71.51, H 4.67, N 18.53; Found: C 71.45, H 4.68, N 18.63

The following compounds (Examples 59 and 60) were obtained according to a similar manner to that of Example 58.

EXAMPLE 59

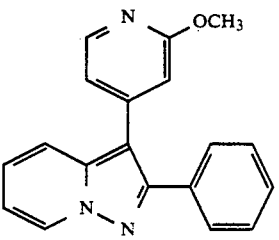

3-(2-Methoxypyridin-4-yl)-2-phenylpyrazolo[1,5-a]pyridine mp: 130°–132° C.

IR (Nujol): 1600, 1530 cm$^{-1}$

NMR (CDCl$_3$, δ): 3.96 (3H, s), 6.80–6.88 (2H, m), 7.19 (1H, dt, J=1.0 Hz and 6.8 Hz), 7.36–7.39 (3H, m), 7.57–7.67 (3H, m), 8.12 (1H, dd, J=1.2 Hz and 4.9 Hz), 8.52 (1H, dd, J=0.9 Hz and 7.0 Hz)

MS: 301 (M+), 270

Analysis Calcd. for C$_{19}$H$_{15}$N$_3$O (%): C 75.73, H 5.02, N 13.94; Found: C 75.72, H 4.97, N 13.78

EXAMPLE 60

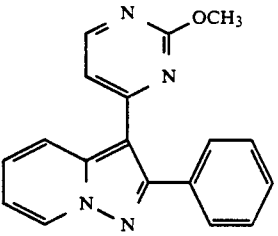

3-(2-Methoxypyrimidin-4-yl)-2-phenylpyrazolo[1,5-a]pyridine mp: 156.5°–157° C.

IR (Nujol): 1620, 1570 cm$^{-1}$

NMR (CDCl$_3$, δ): 4.08 (3H, s), 6.70 (1H, d, J=5.4 Hz), 6.96 (1H, dt, J=1.4 Hz and 6.8 Hz), 7.34–7.64 (6H, m), 8.22 (1H, d, J=5.4 Hz), 8.55 (2H, m)

MS: 301 (M+-1), 271, 243

Analysis Calcd. for C$_{18}$H$_{14}$N$_4$O (%): C 71.51, H 4.67, N 18.53; Found: C 71.44, H 4.68, N 18.47

EXAMPLE 61

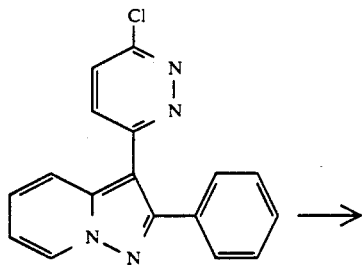

↓

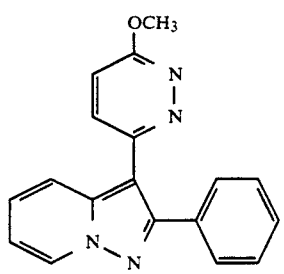

A solution of sodium methoxide in methanol (28%, 411 mg) was added to a mixture of 3-(3-chloropyridazin-6-yl)-2-phenylpyrazolo[1,5-a]pyridine (436 mg) and methanol (4 ml) at room temperature. The reaction mixture was heated under reflux for 3 hours. After evaporating the solvent in vacuo, a saturated aqueous solution of sodium chloride (20 ml) was added to the residue and extracted with chloroform (20 ml×3). The combined extract was washed with a saturated aqueous solution of sodium chloride (20 ml), dried over magnesium sulfate and evaporated in vacuo. The residue was purified by column chromatography on silica gel (10 g) using chloroform as an eluent and recrystallized from 95% EtOH to give 3-(3-methoxypyridazin-6-yl)-2-phenylpyrazolo[1,5-a]pyridine (165 mg).

mp: 203°–205° C.

IR (Nujol): 1625, 1600 cm$^{-1}$

NMR (CDCl$_3$, δ): 4.18 (3H, s), 6.78 (1H, d, J=9.0 Hz), 6.90 (1H, td, J=8.0 Hz and 2.0 Hz), 7.15 (1H, d, J=9.0 Hz), 7.25–7.62 (6H, m), 8.36 (1H, dd, J=9.0 Hz and 1.0 Hz), 8.53 (1H, dd, J=7.0 Hz and 1.0 Hz)

Analysis Calcd. for C$_{18}$H$_{14}$N$_4$O (%): C 71.51, H 4.67, N 18.53; Found: C 71.13, H 4.65, N 18.48

EXAMPLE 62

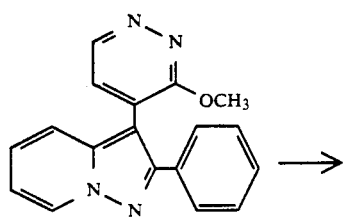

↓

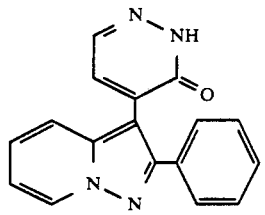

A concentrated hydrochloric acid (5 ml) was added to 3-(3-methoxypyridazin-4-yl)-2-phenylpyrazolo[1,5-a]pyridine (0.50 g) and refluxed for 2 hours and 30 minutes. After cooling, to the reaction mixture was added water (10 ml). The precipitates were collected by filtration to give 3-(3-oxo-2,3-dihydropyridazin-4-yl)-2-phenylpyrazolo[1,5-a]pyridine (0.41 g).

IR (Nujol): 1640, 1600, 1530 cm$^{-1}$

NMR (DMSO$_6$, δ): 7.01 (1H, t, J=6.8 Hz), 7.22 (1H, d, J=4.1 Hz), 7.28–7.61 (7H, m), 7.84 (1H, d, J=4.1 Hz), 8.78 (1H, d, J=6.9 Hz), 13.18 (1H, broad s)

MS: 288 (M+), 261, 231

Analysis Calcd. for C$_{17}$H$_{12}$N$_4$O (%): C 70.82, H 4.20, N 19.43; Found: C 70.87, H 4.15, N 19.88

EXAMPLE 63

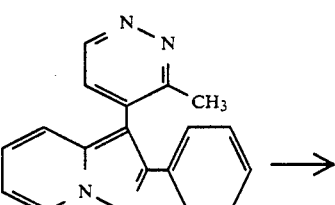

↓

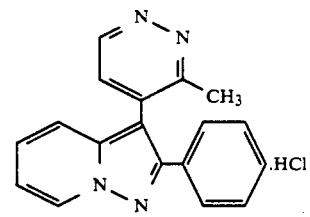

To a ethanol (21 ml) solution of 3-(3-methylpyridazin-4-yl)-2-phenylpyrazolo[1,5-a]pyridine (0.42 g) was added 20 W/V % ethanolic hydrogen chloride solution at room temperature, and stirred for an hour. The precipitates were collected by filtration to give 3-(3-methylpyridazin-4-yl)-2-phenylpyrazolo[1,5-a]pyridine hydrochloride (0.23 g).

mp: 197°–201° C. (dec.)

IR (Nujol): 2700–2150, 2080–1980, 1625, 1605 cm$^{-1}$

NMR (DMSO$_6$/D$_2$O, δ): 2.30 (3H, s), 7.10 (1H, t, J=7.5 Hz), 7.37 (1H, t, J=7.5 Hz), 7.40–7.67 (6H, m), 8.10 (1H, d, J=5.0 Hz), 8.82 (1H, d, J=7.5 Hz), 9.30 (1H, d, J=5.0 Hz)

MS: 286 (M+-HCl), 257, 242, 218

Analysis Calcd. for C$_{18}$H$_{14}$N$_4$.HCl (%): C 66.98, H 4.68, N 17.36; Found: C 66.26, H 5.09, N 16.82

EXAMPLE 64

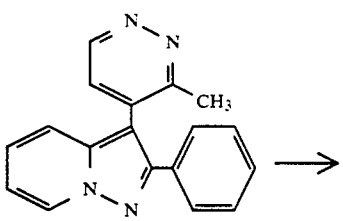

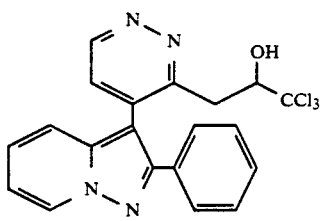

A mixture of 3-(3-methylpyridazin-4-yl)-2-phenylpyrazolo[1,5-a]pyridine (0.40 g), chloral hydrate (0.70 g) and pyridine (4 ml) was stirred for 20 hours at 90°-100° C. After cooling, to the reaction mixture was added methylene chloride (4 ml) and water (4 ml) at room temperature, and stirred for 3 hours. The precipitates were collected by filtration to give 3-[3-(2-hydroxy-3,3,3-trichoropropyl)pyridazin-4-yl]-2-phenylpyrazolo[1,5-a]pyridine (0.26 g).

mp: 206°-207° C.

IR (Nujol): 3400-2900, 1625 cm$^{-1}$

NMR (CDCl$_3$, δ): 2.70-3.60 (2H, m), 4.50-5.30 (1H, m), 6.80 (1H, t, J=7.5 Hz), 7.13-7.40 (8H, m), 7.45 (1H, d, J=7.5 Hz), 9.02 (1H, d, J=6.0 Hz)

MS: 434 (M+), 397, 361, 326, 286

EXAMPLE 65

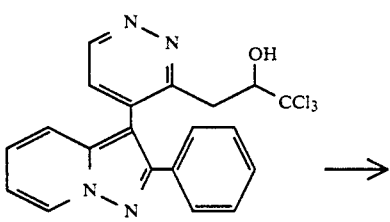

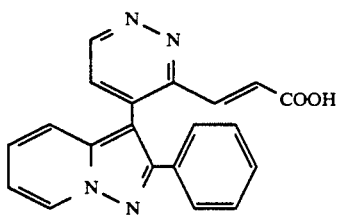

To an ethanol (12 ml) solution of 3-[3-(2-hydroxy-3,3,3-trichloropropyl)pyridazin-4-yl]-2-phenylpyrazolo[1,5-a]pyridine (1.20 g) was added 24% aqueous sodium hydroxide solution (4.8 ml), and refluxed for 5 hours. The reaction mixture was evaporated in vacuo and added 10% hydrochloric acid (12 ml). The precipitates were collected by filtration to give 3-[3-{(E)-2-carboxyvinyl}pyridazin-4-yl]-2-phenylpyrazolo[1,5-a]pyridine (0.64 g).

mp: 227°-229° C. (dec.)

IR (Nujol): 3100, 2550, 1930, 1700, 1630 cm$^{-1}$

MS: 342 (M+), 297, 257, 195

NMR (DMSO-d$_6$, δ): 6.77 (1H, d, J=16.5 Hz), 7.06 (1H, t, J=7.5 Hz), 7.22 (1H, d, J=16.5 Hz), 7.34-7.55 (7H, m), 7.70 (1H, d, J=6.0 Hz), 8.33 (1H, d, J=8.5 Hz), 9.25 (1H, d, J=6.0 Hz), 11.8-12.8 (1H, broad s)

The following compounds (Examples 66 to 74) were prepared according to similar manners to those of Example 1 and Example 2.

EXAMPLE 66

3-(3-Chloropyridazin-4-yl)-2-phenylpyrazolo[1,5-a]pyridine mp: 208°-210° C.

IR (Nujol): 1635, 1570 cm$^{-1}$

EXAMPLE 67

3-(3-Acetylpyridin-4-yl)-2-phenylpyrazolo[1,5-a]pyridine mp: 159°-161° C.

IR (Nujol): 1690, 1630 cm$^{-1}$

EXAMPLE 68

3-(3-Cyanopyridin-4-yl)-2-phenylpyrazolo[1,5-a]pyridine mp: 208°-210° C.

IR (Nujol): 2220, 1630, 1585 cm$^{-1}$

EXAMPLE 69

3-(2-Chloropyridin-4-yl)-2-phenylpyrazolo[1,5-a]pyridine mp: 167°-168° C.

IR (Nujol): 1630, 1590, 1530 cm$^{-1}$

EXAMPLE 70

3-(3-Chloropyridazin-6-yl)-2-phenylpyrazolo[1,5-a]pyridine mp: 208°-211° C.

IR (Nujol): 1630, 1575, 1530 cm$^{-1}$

EXAMPLE 71

3-(3-Methoxypyridazin-4-yl)-2-phenylpyrazolo[1,5-a]pyridine mp: 180°-182° C.

IR (Nujol): 1630, 1580, 1510 cm$^{-1}$

EXAMPLE 72

3-(2-Methoxypyridin-4-yl)-2-phenylpyrazolo[1,5-a]pyridine

EXAMPLE 73

3-(3-Methoxypyridazin-6-yl)-2-phenylpyrazolo[1,5-a]pyridine mp: 203°-205° C.

IR (Nujol): 1625, 1600 cm$^{-1}$

EXAMPLE 74

3-(3-Methylpyridazin-4-yl)-2-phenylpyrazolo[1,5-a]pyridine hydrochloride mp: 197°-201° C. (dec.)

IR (Nujol): 2700-2150, 2080-1980, 1625, 1605 cm$^{-1}$

The following compounds (Example 75 to 89) were prepared according to a similar manner to that of Example 5.

EXAMPLE 75

3-[2-(2-Carboxyethyl)-3-oxo-2,3-dihydropyridazin-6-yl]-2-phenylpyrazolo[1,5-a]pyridine mp: 155.5°-156° C.

IR (Nujol): 1835, 1640, 1570, 1520, 1490 cm$^{-1}$

EXAMPLE 76

3-(1-Methylpyrazol-4-yl)-2-phenylpyrazolo[1,5-a]pyridine
mp: 100°–103° C.
IR (Nujol): 1630 cm$^{-1}$

EXAMPLE 77

3-[2-(3-Carboxypropyl)-3-oxo-2,3-dihydropyridazin-6-yl]-2-phenylpyrazolo[1,5-a]pyridine
mp: 240°–240.5° C.
IR (Nujol): 1710, 1635, 1560, 1530, 1500 cm$^{-1}$

EXAMPLE 78

3-[2-(4-Carboxybutyl)-3-oxo-2,3-dihydropyridazin-6-yl]-2-phenylpyrazolo[1,5-a]pyridine
mp: 182°–183° C.
IR (Nujol): 1710, 1640, 1570, 1530, 1500 cm$^{-1}$

EXAMPLE 79

3-[1-(2-Carboxyethyl)-2-oxo-1,2,5,6-tetrahydropyridin-4-yl]-2-phenylpyrazolo[1,5-a]pyridine
mp: 182°–184° C.
IR (Nujol): 1735, 1640, 1585 cm$^{-1}$

EXAMPLE 80

Sodium salt of 3-[2-(2-carboxyethyl)-3-oxo-2,3,4,5-tetrahydropyridazin-6-yl]-2-phenylpyrazolo[1,5-a]pyridine
IR (Nujol): 1640, 1560, 1510 cm$^{-1}$

EXAMPLE 81

3-[1-(2-Carboxyethyl)-5-hydroxypyrazol-3-yl]-2-phenylpyrazolo[1,5-a]pyridine
mp: 211°–213° C.
IR (Nujol): 1705, 1610 cm$^{-1}$

EXAMPLE 82

3-[2-(2-Carbamoylethyl)-3-oxo-2,3-dihydropyridazin-6-yl]-2-phenylpyrazolo[1,5-a]pyridine
mp: 215°–215.5° C.
IR (Nujol): 3450, 3330, 3210, 1660, 1595, 1535 cm$^{-1}$

EXAMPLE 83

3-[2-(2-N,N-Dimethylcarbamoylethyl)-3-oxo-2,3-dihydropyridazin-6-yl]-2-phenylpyrazolo[1,5-a]pyridine
mp: 144°–145° C.
IR (Nujol): 1665, 1640, 1590, 1530 cm$^{-1}$

EXAMPLE 84

1-[3-(6-(2-Phenylpyrazolo[1,5-a]pyridin-3-yl)-3-oxo-2,3-dihydropyridazin-2-yl}propionyl]piperidine
mp: 65°–70° C.
IR (Nujol): 1660, 1630, 1585, 1520 cm$^{-1}$

EXAMPLE 85

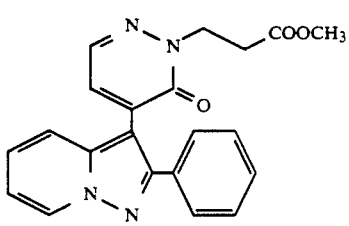

3-[2-(2-Methoxycarbonylethyl)-3-oxo-2,3-dihydropyridazin-4-yl]-2-phenylpyrazolo[1,5-a]pyridine
mp: 136°–138° C.
IR (Nujol): 1730, 1640, 1600 cm$^{-1}$
NMR (CDCl$_3$, δ): 2.92 (2H, t, J=6.0 Hz), 3.72 (3H, s), 4.57 (2H, t, J=6.0 Hz), 6.82 (1H, t, J=7.0 Hz), 6.91 (1H, d, J=4.5 Hz), 7.1–7.7 (8H, m), 8.55 (1H, d, J=7.0 Hz)
MS: 374 (M$^+$), 315, 287

EXAMPLE 86

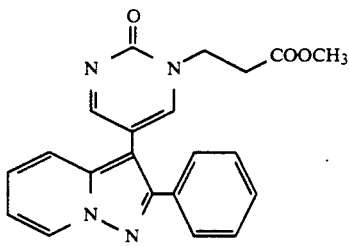

3-[1-(2-Methoxycarbonylethyl)-2-oxo-1,2-dihydropyrimidin-5-yl]-2-phenylpyrazolo[1,5-a]pyridine
mp: 115°–118° C.
IR (Nujol): 1730, 1660 cm$^{-1}$
NMR (CDCl$_3$, δ): 2.97 (2H, t, J=6.0 Hz), 3.66 (3H, s), 4.16 (2H, t, J=6.0 Hz), 6.82 (1H, t, J=7.5 Hz), 7.21 (1H, t, J=7.5 Hz), 7.33–7.73 (6H, m), 7.91 (1H, d, J=4.0 Hz), 8.49 (1H, d, J=4.0 Hz), 8.52 (1H, s)
MS: 374 (M$^+$), 332, 288, 272

EXAMPLE 87

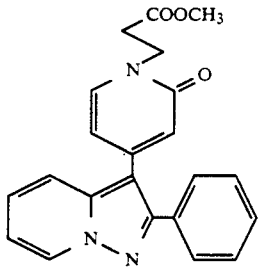

3-[1-(2-Methoxycarbonylethyl)-2-oxo-1,2-dihydropyridin-4-yl]-2-phenylpyrazolo[1,5-a]pyridine
mp: 173°–174° C.
IR (Nujol): 1740, 1660, 1590 cm$^{-1}$
NMR (CDCl$_3$, δ): 2.91 (2H, t, J=6.3 Hz), 3.69 (3H, s), 4.21 (2H, t, J=6.3 Hz), 5.98 (1H, dd, J=1.9 Hz and 7.1 Hz), 6.72 (1H, d, J=1.8 Hz), 6.86 (1H, dt, J=14 Hz and 6.9 Hz), 7.2–7.4 (1H, m, J=7 Hz), 7.6–7.7 (2H, m), 7.74 (1H, d, J=9.0 Hz), 8.51 (1H, d, J=7.0 Hz)
MS: 373 (M$^+$), 314, 286

EXAMPLE 88

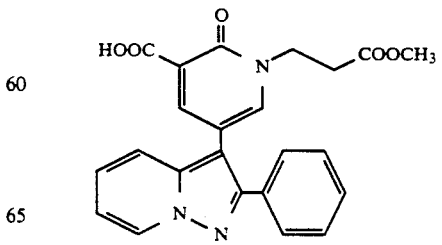

3-[1-(2-Methoxycarbonylethyl)-3-carboxy-2-oxo-1,2-dihydropyridin-5-yl]-2-phenylpyrazolo[1,5-a]pyridine mp: 185°–186° C.

IR (Nujol): 1725, 1630, 1560 cm$^{-1}$

NMR (CDCl$_3$, δ): 2.92 (2H, t, J=6.0 Hz), 3.68 (3H, s), 4.31 (2H, t, J=6.0 Hz), 6.89 (1H, t, J=7.5 Hz), 7.1–7.7 (7H, m), 7.80 (1H, d, J=3.0 Hz), 8.50 (1H, d, J=7.5 Hz), 8.57 (1H, d, J=3.0 Hz)

MS: 373, 314, 287

EXAMPLE 89

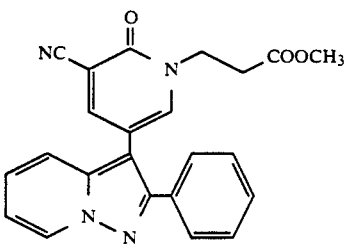

3-[1-(2-Methoxycarbonylethyl)-3-cyano-2-oxo-1,2-dihydropyridin-5-yl]-2-phenylpyrazolo[1,5-a]pyridine mp: 155°–157° C.

IR (Nujol): 2225, 1725, 1660, 1620 cm$^{-1}$

NMR (CDCl$_3$, δ): 2.90 (2H, t, J=6.0 Hz), 2.63 (3H, s), 4.20 (2H, t, J=6.0 Hz), 6.81 (1H, t, J=7.5 Hz), 7.20 (1H, t, J=7.5 Hz), 7.4–7.7 (7H, m), 7.78 (1H, d, J=3.0 Hz), 7.49 (1H, d, J=7.5 Hz)

MS: 398 (M$^+$), 312

The following compounds (Examples 90 to 92) were obtained according to a similar manner to that of Example 6.

EXAMPLE 90

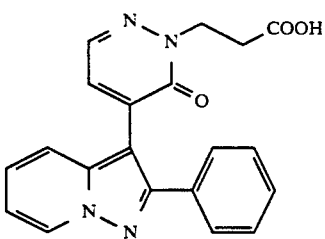

3-[2-(2-Carboxyethyl)-3-oxo-2,3-dihydropyridazin-4-yl]-2-phenylpyrazolo[1,5-a]pyridine mp: 150°–152° C.

IR (Nujol): 1710, 1630, 1590 cm$^{-1}$

NMR (CDCl$_3$, δ): 2.97 (2H, t, J=7.0 Hz), 4.58 (2H, t, J=7.0 Hz), 6.87 (1H, dt, J=1.3 Hz and 6.9 Hz), 6.95 (1H, d, J=4.2 Hz), 7.2–7.7 (8H, m), 8.53 (1H, d, J=6.9 Hz)

MS: 360 (M$^+$), 288

EXAMPLE 91

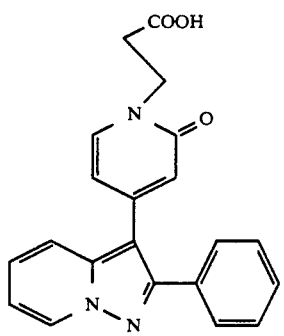

3-[1-(2-Carboxyethyl)-2-oxo-1,2-dihydropyridin-4-yl]-2-phenylpyrazolo[1,5-a]pyridine mp: 238°–241° C.

IR (Nujol): 1700, 1640 cm$^{-1}$

IR (DMSO-d$_6$, δ): 2.70 (2H, t, J=7.5 Hz), 4.06 (2H, t, J=7.5 Hz), 6.04 (1H, dd, J=1.9 Hz and 7.0 Hz), 6.37 (1H, d, J=1.9 Hz), 7.04 (1H, dt, J=1.3 Hz and 6.9 Hz), 7.3–7.7 (7H, m), 7.74 (1H, d, J=8.8 Hz), 8.80 (1H, d, J=6.9 Hz), 12.2–12.6 (1H, broad)

MS: 358 (M$^+$), 314, 286

EXAMPLE 92

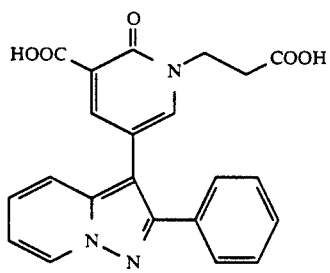

3-[1-(2-Carboxyethyl)-3-carboxy-2-oxo-1,2-dihydropyridin-5-yl]-2-phenylpyrazolo[1,5-a]pyridine mp: 209°–211° C.

IR (Nujol): 1730, 1690, 1630 cm$^{-1}$

NMR (DMSO-d$_6$, δ): 2.83 (2H, t, J=6.0 Hz), 4.35 (2H, t, J=6.0 Hz), 6.98 (1H, t, J=7.5 Hz), 7.2–7.8 (7H, m), 8.03 (1H, d, J=3.0 Hz), 8.44 (1H, d, J=3.0 Hz), 8.75 (1H, dd, J=7.5 Hz)

MS: 403 (M$^+$), 331, 287

EXAMPLE 93

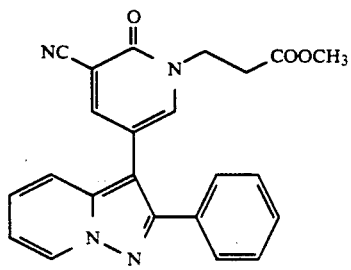

→

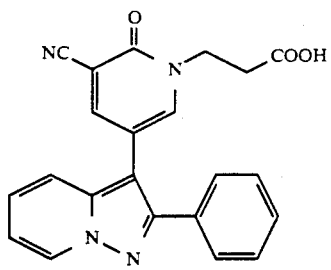

A mixture of 3-[1-(2-methoxycarbonylethyl)-3-cyano-2-oxo-1,2-dihydropyridin-5-yl]-2-phenylpyrazolo[1,5-a]pyridine (0.46 g) and potassium carbonate (0.92 g) in 80% aqueous ethanol (4.6 ml) was stirred for 6 hours at 80° C. The mixture was acidified with 5% hydrochloric acid (pH≈2). The resultant precipitates were collected by filtration, washed with water (10 ml), and subjected to a column chromatography on silica gel (10 g) with a mixture of chloroform, methanol and acetic acid (40:4:1). The fractions containing the object compound were combined and evaporated in vacuo to give 3-[1-(2-carboxyethyl)-3-cyano-2-oxo-1,2-dihydropyridin-5-yl]-2-phenylpyrazolo[1,5-a]pyridine (0.40 g).

mp: 196°–200° C.

IR (Nujol): 3400, 2230, 1720, 1660, 1600 cm$^{-1}$

NMR (DMSO-d$_6$, δ): 2.69 (2H, t, J=6.0 Hz), 4.18 (2H, t, J=6.0 Hz), 6.99 (1H, t, J=7.8 Hz), 7.31 (1H, t, J=7.8 Hz), 7.4–7.7 (5H, m), 7.77 (1H, d, J=9.0 Hz), 7.92 (1H, d, J=3.0 Hz), 8.30 (1H, d, J=3.0 Hz), 8.76 (1H, d, J=7.8 Hz)

MS: 384 (M$^+$), 312

The following compounds (Example 94 to 97) were obtained according to a similar manner to that of Example 5.

EXAMPLE 94

3-[2-(2-Carboxyethyl)-3-oxo-2,3-dihydropyridazin-4-yl]-2-phenylpyrazolo[1,5-a]pyridine IR (Nujol): 1710, 1630, 1590 cm$^{-1}$

EXAMPLE 95

3-[1-(2-Carboxyethyl)-2-oxo-1,2-dihydropyridin-4-yl]-2-phenylpyrazolo[1,5-a]pyridine IR (Nujol): 1700, 1640 cm$^{-1}$

EXAMPLE 96

3-[1-(2-Carboxyethyl)-3-carboxy-2-oxo-1,2-dihydropyridin-5-yl]-2-phenylpyrazolo[1,5-a]pyridine IR (Nujol): 1730, 1690, 1630 cm$^{-1}$

EXAMPLE 97

3-[1-(2-Carboxyethyl)-3-cyano-2-oxo-1,2-dihydropyridin-5-yl]-2-phenylpyrazolo[1,5-a]pyridine IR (Nujol): 3400, 2230, 1720, 1660, 1600 cm$^{-1}$

EXAMPLE 98

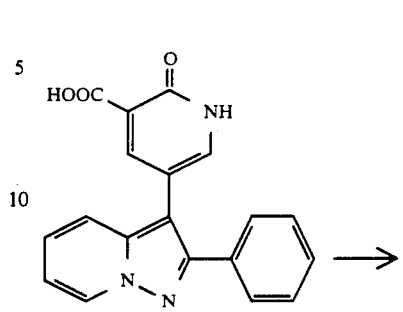

To a mixture of 3-(3-carboxy-2-oxo-1,2-dihydropyridin-5-yl)-2-phenylpyrazolo[1,5-a]pyridine (0.92 g) and potassium hydroxide powder (0.54 g) in N,N-dimethylformamide (9 ml) was added 93% methyl iodide (0.64 ml) under ice-cooling (0°–5° C.). The mixture was stirred for 3 hours under ice-cooling, and then at room temperature for 1 hour and diluted with water. The resultant precipitates were filtered off and the filtrate was acidified with 5% hydrochloric acid and extracted with ethyl acetate (20 ml). The extract was washed with water (5 ml) and sodium chloride aqueous solution (5 ml), then dried over magnesium sulfate. The solvent was removed and the residue was chromatographed on silica gel (12 g) with a mixture of chloroform and methanol (100:1) as an eluent. The fractions containing the object compound were combined and evaporated in vacuo to give 3-(1-methyl-3-methoxycarbonyl-2-oxo-1,2-dihydropyridin-5-yl)-2-phenylpyrazolo[1,5-a]pyridine (0.34 g).

mp: 268°–270° C.

IR (Nujol): 1690, 1670, 1620 cm$^{-1}$

NMR (CDCl$_3$, δ): 3.54 (3H, s), 3.86 (3H, s), 6.82 (1H, t, J=2.5 Hz), 7.18 (1H, t, J=7.5 Hz), 7.2–7.8 (9H, m), 8.18 (1H, s), 8.50 (1H, d, J=7.5 Hz)

MS: 359 (M$^+$)

EXAMPLE 99

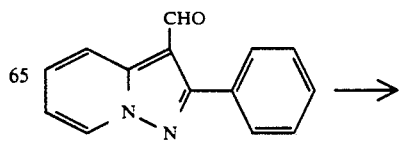

-continued

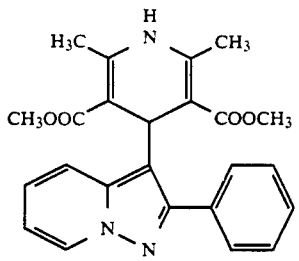

A mixture of 2-phenylpyrazolo[1,5-a]pyridine-3-carbaldehyde (1.00 g), methyl acetoacetate (1.10 g), and 14% methanolic ammonia (18 ml) in a mixture of methanol (20 ml) and chloroform (10 ml) was stirred for 246 hours at room temperature. The solvent was removed in vacuo and the residue was dissolved in methylene chloride (30 ml). The solution was washed with water (10 ml) and sodium chloride aqueous solution (10 ml), dried over magnesium sulfate and evaporated in vacuo. The residue was chromatographed on silica gel (15 g) with a mixture of n-hexane and ethyl acetate (2:1). The fractions containing the object compound were combined and evaporated in vacuo to give 3-[2,6-dimethyl-3,5-bis(methoxycarbonyl)-1,4-dihydropyridin-4-yl]-2-phenylpyrazolo[1,5-a]pyridine. This compound was purified from a mixture of ethyl acetate and n-hexane.
mp: 183°–186° C.
IR (Nujol): 3330, 3250, 3120, 1690 cm$^{-1}$
NMR (CDCl$_3$, δ): 2.13 (6H, s), 3.37 (6H, s), 5.19 (1H, broad), 5.51 (1H, s), 6.69 (1H, t, J=6.8 Hz), 7.06 (1H, t, J=6.8 Hz), 7.3–7.7 (6H, m), 8.36 (1H, d, J=6.8 Hz)
MS: 417 (M$^+$), 358

What we claim is:

1. A method for the prevention and/or the treatment of renal toxicity, nephrosis, or nephritis, which comprises administering an effective amount of a pyrazolopyridine compound of the formula:

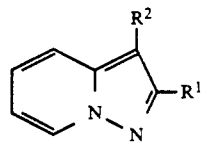

wherein
R$^1$ is aryl, and
R$^2$ is an unsaturated heterocyclic group which contains at least one heteroatom selected from the group consisting of N, O and S, which may have one or more suitable substituent(s), or a pharmaceutically acceptable salt thereof to a human being or an animal.

* * * * *

UNITED STATES PATENT AND TRADEMARK OFFICE
CERTIFICATE OF CORRECTION

PATENT NO. : 5,155,114

DATED : October 13, 1992

INVENTOR(S) : Youichi Shiokawa et al.

It is certified that error appears in the above-identified patent and that said Letters Patent is hereby corrected as shown below:

On Title page, Item[63], Related U.S. Application Data, please correct to read as follows:

--Continuation-in-part of Ser. No. 626,009, Dec. 12, 1990, abandoned, which is a Continuation of Ser. No. 466,929, Jan. 18, 1990, Pat. No. 4,985,444--

Signed and Sealed this

Twenty-eighth Day of September, 1993

Attest:

BRUCE LEHMAN

Attesting Officer

Commissioner of Patents and Trademarks